United States Patent
Buskiewicz et al.

(10) Patent No.: US 10,967,047 B2
(45) Date of Patent: Apr. 6, 2021

(54) MITOCHONDRIAL ANTIVIRAL-SIGNALING (MAVS) POLYPEPTIDES AND DETECTION AND USE THEREOF

(71) Applicant: University of Vermont and State Agricultural College, Burlington, VT (US)

(72) Inventors: Iwona A. Buskiewicz, Biurlington, VT (US); Andreas Koenig, Biurlington, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 16/095,093

(22) PCT Filed: Apr. 21, 2017

(86) PCT No.: PCT/US2017/028922
§ 371 (c)(1),
(2) Date: Oct. 19, 2018

(87) PCT Pub. No.: WO2017/185022
PCT Pub. Date: Oct. 26, 2017

(65) Prior Publication Data
US 2019/0099470 A1 Apr. 4, 2019

Related U.S. Application Data
(60) Provisional application No. 62/325,618, filed on Apr. 21, 2016.

(51) Int. Cl.
*G01N 33/50* (2006.01)
*G01N 33/53* (2006.01)
*G01N 33/537* (2006.01)
*A61K 38/17* (2006.01)
*A61K 38/07* (2006.01)
*G01N 33/564* (2006.01)
*G01N 33/536* (2006.01)
*A61K 31/66* (2006.01)
*C07K 14/00* (2006.01)
*C07K 16/00* (2006.01)

(52) U.S. Cl.
CPC .............. *A61K 38/17* (2013.01); *A61K 31/66* (2013.01); *A61K 38/07* (2013.01); *C07K 14/00* (2013.01); *C07K 16/00* (2013.01); *G01N 33/50* (2013.01); *G01N 33/536* (2013.01); *G01N 33/564* (2013.01); *G01N 2800/24* (2013.01); *G01N 2800/52* (2013.01)

(58) Field of Classification Search
None
See application file for complete search history.

(56) References Cited

FOREIGN PATENT DOCUMENTS
WO 2012037232 A2 3/2012

OTHER PUBLICATIONS

Jacob et al. Regulation of Mitochondrial Antiviral Signaling (MAVS) Expression and Signaling by the Mitochondria-associated Endoplasmic Reticulum Membrane (MAM) Protein Gp78. The Journal of Biological Chemistry vol. 289, No. 3, pp. 1604-1616, Jan. 17, 2014.*

Zurawek et al. MAVS is not a Likely Susceptibility Locus for Addison's Disease and Type 1 Diabetes. Arch. Immunol. Ther. Exp. (2017) 65:271-274.*

Su et al. Investigation of the caspase-dependent mitochondrial apoptotic pathway in mononuclear cells of patients with systemic lupus erythematosus. Journal of Translational Medicine 2014, 12:303.*

Alberti et al., "A Systematic Survey Identifies Prions and Illuminates Sequence Features of Prionogenic Proteins." Cell (2009), vol. 137, pp. 146-158.

Ardail et al., "Mitochondrial Contact Sites, Lipid Composition and Dynamics." The Journal of Biological Chemistry (1990), vol. 265, No. 31, pp. 18797-18802.

Bombardier et al., "Derivation of the Sledai, A Disease Activity Index for Lupus Patients." Arthritis and Rheumatism (1992), vol. 35, No. 6, pp. 630-640.

Buskiewicz et al., "Reactive oxygen species induce virus-independent MAVS oligomerization in systemic lupus erythematosus." Sci Signal. Nov. 29, 2016; 9(456): ra115.

Bustillo-Zabalbeitia et al., "Specific Interaction with Cardiolipin Triggers Functional Activation of Dynamin-Related Protein 1." PlOs One (2014), vol. 9, No. 7, p. e102738.

Callahan et al., "Free radicals alter maximal diaphragmatic mitochondrial oxygen consumption in endotoxin-induced sepsis." Free Radical Biology and Medicine (2001), vol. 30, Issue 1, pp. 129-138.

Chen et al., "Identification and Characterization of MAVS, a Mitochondrial Antiviral Signaling Protein that Activates NF-kB and IRF3." Cell (2005) 122: 669-682.

Chong et al., "Midazolam protects B35 neuroblastoma cells through Akt-Aktphosphorylation in reactive oxygen species derived cellular injury." Korean Journal Anesthesiol, Feb. 2012, vol. 62(2), pp. 166-171.

Dauer et al., "Mature Dendritic Cells Derived from Human Monocytes Within 48 Hours: A Novel Strategy for Dendritic Cell Differentiation from Blood Precursors." The Journal of Immunology (2003), vol. 170, No. 8, pp. 4069-4076.

De Moura et al., "Bioenergetic Analysis of Intact Mammalian Cells Using the Seahorse XF24 Extracellular Flux Analyzer and Luciferase ATP Assay." Methods in Molecular Biology (2014), 1105, pp. 589-602.

(Continued)

*Primary Examiner* — Nianxiang Zou
(74) *Attorney, Agent, or Firm* — Pierce Atwood LLP

(57) ABSTRACT

The invention relates, in part, to compounds, compositions, and methods to assess characteristics of mitochondrial antiviral-signaling (MAVS) polypeptides and also to methods of modulating MAVS polypeptide characteristics. In addition, the invention relates, in part, to assays to assess characteristics of polypeptides.

11 Claims, 17 Drawing Sheets
Specification includes a Sequence Listing.

(56) References Cited

OTHER PUBLICATIONS

Gibson et al., "Kinetics and Mechanism of Action of Glucose Oxidase." The Journal of Biological Chemistry (1964), vol. 239, No. 11, pp. 3927-3934.
Hanson et al., "Investigating Mitochondrial Redox Potential with Redox-sensitive Green Fluorescent Protein Indicators." The Journal of Biological Chemistry (2004), vol. 279, No. 13, pp. 13044-13053.
Hornung et al., "5'-Triphosphate RNA Is the Ligand for RIG-1." Science (2006), 314, pp. 994-997.
Hou et al., "MAVS Forms Functional Prion-like Aggregates to Activate and Propagate Antiviral Innate Immune Response." Cell, vol. 146, Issue 3, Aug. 5, 2011, pp. 448-461.
Inaba et al., "Generation of Large Numbers of Dendritic Cells from Mouse Bone Marrow Cultures Supplemented with Granulocyte/Macrophage Colony-stimulating Factor." J. Exp. Med. (1992), vol. 176, pp. 1693-1702.
International Preliminary Report on Patentability and the Written Opinion of the International Searching Authority dated Oct. 23, 2018 from corresponding PCT/US2017/028922 filed on Apr. 21, 2017.
International Search Report dated Sep. 8, 2017 from corresponding PCT/US2017/028922 filed on Apr. 21, 2017.
James et al., "Interactions of Mitochondria-targeted and Untargeted Ubiquinones with the Mitochondrial Respiratory Chain and Reactive Oxygen Species." The Journal of Biological Chemistry (2005), vol. 280, No. 22: 21295-21312.
Kelso et al., "Selective Targeting of a Redox-active Ubiqinone to Mitochondria within Cells." The Journal of Biological Chemistry (2001), vol. 276, No. 7, pp. 4588-4596.
Knowlton et al., "A Mutation in the Puff Region of VP2 Attenuates the Myocarditic Phenotype of an Infectious cDNA of the Woodruff Variant of Coxsackievirus B3." Journal of Virology (1996), vol. 70, No. 11, pp. 7811-7818.
Koenig et al., "Spontaneous MAVS-Oligomerization in Systemic Lupus Erythematosus." World Mitochondria Society Abstracts (2014).
Mallone et al., "Isolation and preservation of peripheral blood mononuclear cells for analysis of islet antigen-reactive T cell responses: position statement of the T-Cell Workshop Committee of the Immunology of Diabetes Society." Clinical and Experimental Immunology (2010), vol. 163, pp. 33-49.
Monteiro et al., "Echinococcus granulosus Antigen B Structure: Subunit Composition and Oligomeric States." PLOS Neglected Tropical Diseases (2012), 6(3), e551: 10 pages.
Mukherjee et al., "The Coxsackievirus B 3Cpro Protease Cleaves MAVS and TRIF to Attenuate Host Type I Interferon and Apoptotic Signaling." PLOS Pathogens (2011), 7(3), e1001311: 14 pages.
Nobre et al., "Modulation of Innate Immune Signalling by Lipid-Mediated MAVS Transmembrane Domain Oligomerization." PLoS One (2015), vol. 10, No. 8, p. e0136883.
Nulton-Persson et al., "Modulation of Mitochondrial Function by Hydrogen Peroxide." The Journal of Biological Chemistry (2001), vol. 276, No. 26, pp. 23357-23361.
Otera et al., "New insights into the functoin and regulation of mitochondrial fission." Biochimica et Biophysica Acta 1833 (2013), p. 1256-1268.
Perl et al., "Mitochondrial Dysfunction in T Cells of Patients with Systemic Lupus Erythematosus." International Reviews of Immunology (2004), 23:1-21.
Pothlichet et al., "A loss-of-function variant of the antiviral molecule MAVS is associated with a subset of systemic lupus patients." EMBO Molecular Medicine (2011), vol. 3, pp. 142-152.
Robb et al., "Selective superoxide generation within mitochondria by the targeted redox cycler MitoParaquat." Free Radical Biology and Medicine (2015), vol. 89, pp. 883-894.
Rohnstock et al., "Evaluation of the probe dihydrocalcein acetoxymethylester as an indicator of reactive oxygen species formation and comparison with oxidative DNA base modification determined by modified alkaline elution technique." Toxicology in Vitro 21 (2007) 1552-1562.
Russell et al., "Sindbis Virus Mutations Which Coordinately Affect Glycoprotein Processing, Penetration, and Virulence in Mice." Journal of Virology (1989), vol. 63, No. 4, pp. 1619-1629.
Scaduto et al., "Measurement of Mitochondrial Membrane Potential Using Fluorescent Rhodamine Derivatives." Biophysical Journal (1999), vol. 76, pp. 469-477.
Schmidt et al., "Plaque Assay and Improved Yield of Human Coronaviruses in a Human Rhabdomyosarcoma Cell Line." Journal of Clinical Microbiology (1979), vol. 9, No. 6, pp. 722-728.
Schmitt et al., "A semi-automated method for isolating functionally intact mitochondria from cultured cells and tissue biopsies." Analytical Biochemistry 443 (2013) 66-74.
Szeto, H.H., "Cell-permeable, Mitochondrial-targeted, Peptide Antioxidants." The AAPS Journal 2006; 8(2) Article 32: E277-E283.
Szeto, H.H., "First-in-class cardiolipin-protective compound as a therapeutic agent to restore mitochondrial bioenergetics." Br. J. Pharmacol. (2014), vol. 171, No. 8, pp. 2029-2050.
Tan et al., "The 1982 Revised Criteria for The Classification of Systemic Lupus Erythematosus." Arthritis and Rheumatism (1982), vol. 25, No. 11, pp. 1271-1277.
Wu et al., "Multiparameter metabolic analysis reveals a close link between attenuated mitochondrial bioenergetic function and enhanced glycolysis dependency in human tumor cells." American Journal of Physiology (2007), Cell Physiology 292, C125-136.
Xu et al., "Structural basis for the prion-like MAVS filaments in antiviral innate immunity." eLIFE (2014); 3:e01489, 25 pages.
Ronnblom et al., "The interferon signature in autoimmune diseases." Current Opinion, vol. 25, No. 2, Mar. 2013, pp. 248-253.

* cited by examiner

Fig. 11

| Patient | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| C79F | - | - | - | - | - | - | - | nd | nd | - | - | nd | nd | - | - | - | - |
| Q93E | + | - | - | - | + | + | - | nd | nd | - | - | nd | nd | - | - | + | - |
| MAVS | + | + | +++ | + | ++++ | + | +++ | ++ | +++ | ++ | +++ | ++ | - | ++ | - | - | ++ |
| IFN-1 | + | + | ++++ | + | ++++ | + | +++ | +++ | ++++ | +++ | +++ | +++ | + | ++ | - | ++ | ++ |
| SLEDAI | 4 | 6 | 10 | 0 | 4 | 0 | 4 | 7 | 12 | 9 | 6 | 8 | 6 | 4 | 4 | 0 | 0 |

MAVS oligomerization and IFN-1 change were normalized among all 17 patients, where the highest patient value was defined as 1. MAVS oligomerization and IFN-1 per patient were scored with +, ++, +++, ++++, when the absolute mean value after normalization was falling between 0 and 0.25, 0.25 and 0.5, 0.5 and 0.75 or 0.75 and 1.00 respectively. (nd = not determined)

MITOCHONDRIAL ANTIVIRAL-SIGNALING (MAVS) POLYPEPTIDES AND DETECTION AND USE THEREOF

RELATED APPLICATIONS

This application is a National Stage Filing under U.S.C. § 371 of PCT International Application PCT/US17/28922, filed Apr. 21, 2017, which was published under PCT Article 21(2) in English, which claims the benefit under 35 U.S.C. § 119(e) of U.S. Provisional application Ser. No. 62/325,618 filed Apr. 21, 2016, the content of each of which is incorporated by reference herein in its entirety.

GOVERNMENT INTEREST

This invention was made with government support under grants 5P20 GM103496 and 5R01 HL086549 awarded by the National Institutes of Health. The Government has certain rights in the invention.

FIELD OF THE INVENTION

The invention relates, in part, to compounds, compositions, and methods to assess characteristics of mitochondrial antiviral-signaling (MAVS) polypeptide and also to methods of modulating characteristics of oligomerized MAVS polypeptide complexes, such as structure and function. In addition, the invention relates, in part, to assays to assess characteristics of oligomerized MAVS polypeptides and complexes.

BACKGROUND OF THE INVENTION

Mitochondrial antiviral-signaling protein (MAVS), also known as VISA (virus-induced signaling adapter), IPS-1 (interferon-beta promoter stimulator 1), is a 54 kDa protein that is tethered via a simple transmembrane domain to the outer mitochondrial membrane of virtually all mammalian organisms. MAVS has been reported to form oligomers in a prion-like manner (F. Hou et al., (2011) Cell 146, 448-461; H. Xu et al., (2014) eLife 3, e01489) and have been identified as involved with the early immune response to viral infections.

SUMMARY OF THE INVENTION

According to an aspect of the invention, methods of selecting an autoimmune disease treatment for a subject are provided. The methods include: (a) identifying a subject at risk for an autoimmune disease; (b) obtaining a serum sample from the subject; (c) contacting the serum sample with a MAVS-binding agent under suitable conditions for the MAVS-binding agent to form a bound complex comprising the MAVS-binding agent and an oligomerized MAVS polypeptide complex, (d) determining a characteristic of the bound complex; and (e) selecting a treatment for the autoimmune disease based at least in part on the determined characteristic of the bound complex. In some embodiments, the characteristic of the bound complex is one or more of the level of the bound complex and a physical property of the oligomerized MAVS polypeptide complex in the bound complex. In certain embodiments, the physical property of the oligomerized MAVS polypeptide complex comprises the molecular weight of the oligomerized MAVS polypeptide complex. In some embodiments, the molecular weight of the oligomerized MAVS polypeptide complex is determined to be at least 200 kDa. In some embodiments, the molecular weight of the oligomerized MAVS polypeptide complex is determined to be between 250 kDa-1500 kDa. In certain embodiments, the oligomerized MAVS polypeptide complex comprises aggregates of N-terminal caspase activation and recruitment domain (CARD) of MAVS. In some embodiments, the oligomerized MAVS polypeptide complex comprises the oligomerized MAVS polypeptide and a phospholipid. In certain embodiments, the phospholipid is cardiolipin. In some embodiments, the physical characteristic of the oligomerized MAVS polypeptide complex is the presence of the cardiolipin. In some embodiments, the autoimmune disease is Systemic Lupus Erythematosus (SLE), atherosclerosis, Sjögren's syndrome, rheumatoid arthritis, asthma that is positive for type I IFN signature, dilated cardiomyopathy, cardiomyopathy, systemic sclerosis, Aicardi-Goutieres syndrome, type I diabetes, autoimmune thyroid disease, or neuromyelitis optica. In some embodiments, the MAVS-binding agent is an antibody or functional fragment thereof that specifically binds the oligomerized MAVS polypeptide complex. In some embodiments, the MAVS-binding agent specifically binds an N-terminal caspase activation and recruitment domain (CARD) of MAVS. In some embodiments, the MAVS-binding agent is an indirect MAVS-binding agent that binds the additional component of the bound complex. In certain embodiments, the indirect MAVs-binding agent specifically binds one or more of: cardiolipin and an oligomerized MAVS polypeptide complex comprising cardiolipin. In certain embodiments, the subject is a mammal, optionally a human. In some embodiments, the treatment comprises administering to the subject one or more of: a therapeutic agent, a behavioral modification, a diet modification, a surgical procedure, and physical therapy procedure. In certain embodiments, the specific binding of the MAVS-binding agent to the N-terminal caspase activation and recruitment domain (CARD) of MAVS aids in selecting administration of an anti-oxidative agent as a treatment for the subject. In some embodiments, the specific binding of the MAVS-binding agent to the N-terminal caspase activation and recruitment domain (CARD) of MAVS aids in selecting administration of at least one anti-oxidative agent as a treatment for the subject. In some embodiments, the anti-oxidative agent is MitoQ. In some embodiments, the anti-oxidative agent is a Szeto-Schiller (SS) peptide antioxidant. In some embodiments, the SS peptide is mitochondria-targeted tetra peptide (MTP) SS-31. In some embodiments, a means of determining the characteristic of the bound complex comprises measuring the level of the oligomerized MAVS polypeptide complex using any aspect of an h-FRET assay described herein. In some embodiments, a means of determining the characteristic of the bound complex comprises measuring a level of the cardiolipin (CL), wherein measuring the level of the CL comprises one or more of: determining presence of absence of CL and determining an amount of the CL.

According to another aspect of the invention, methods of assessing a characteristic of a bound complex comprising a serum mitochondrial antiviral-signaling (MAVS) oligomerized polypeptide complex and a MAVS-binding agent are provided. The methods including: (a) contacting a serum sample with a MAVS-binding agent under suitable conditions for the MAV-binding agent to bind an oligomerized MAVS polypeptide complex; and (b) determining a characteristic of a bound complex comprising the serum oligomerized MAVS polypeptide complex and the MAVS-binding agent in the sample. In some embodiments, the characteristic of the bound complex is one or more of: the presence or absence of the bound complex, a level of the bound complex, and a physical property of the oligomerized MAVS polypeptide complex in the bound complex. In certain embodiments, a level greater than zero of the bound complex determines the presence of the bound complex and a level of zero determines the absence of the oligomerized MAVS polypeptide complex. In some embodiments, the physical property of the oligomerized MAVS polypeptide complex comprises the molecular weight of the oligomerized MAVS polypeptide complex. In some embodiments, the molecular weight of the oligomerized MAVS polypeptide complex is determined to be at least 200 kDa. In certain embodiments, the molecular weight of the oligomerized MAVS polypeptide complex is determined to be between 250 kDa-1500 kDa. In some embodiments, the MAVS-binding agent is an antibody or functional fragment thereof that specifically binds the oligomerized MAVS polypeptide complex. In some embodiments, the MAVS-binding agent specifically binds an N-terminal caspase activation and recruitment domain (CARD) of MAVS. In some embodiments, the oligomerized MAVS polypeptide complex comprises the oligomerized MAVS polypeptide and a phospholipid. In some embodiments, the phospholipid is cardiolipin. In some embodiments, the physical characteristic of the oligomerized MAVS polypeptide complex is the presence of the cardiolipin. In some embodiments, the MAVS-binding agent is an indirect MAVS-binding agent that binds the additional component of the bound complex. In some embodiments, the indirect MAVs-binding agent specifically binds one or more of: cardiolipin and an oligomerized MAVS polypeptide complex comprising cardiolipin. In certain embodiments, the serum sample is a sample obtained from a subject. In some embodiments, the subject is a mammal, optionally a human. In certain embodiments, the method also includes using the determined presence of the bound complex to assist in identifying the presence of an autoimmune disease in the subject. In some embodiments, the autoimmune disease is Systemic Lupus Erythematosus (SLE), atherosclerosis, Sjögren's syndrome, rheumatoid arthritis, asthma that is positive for type I IFN signature, dilated cardiomyopathy, cardiomyopathy, systemic sclerosis, Aicardi-Goutieres syndrome, type I diabetes, autoimmune thyroid disease, or neuromyelitis optica. In some embodiments, the method also includes using the determined presence of the bound complex to assist in one or more of: selecting a treatment for the subject and treating the subject. In certain embodiments, the treatment comprises one or more of administering to the mammal: a pharmaceutical agent, a behavioral modification protocol, a diet modification protocol, a surgical procedure, and a physical therapy procedure. In some embodiments, the specific binding of the MAVS-binding agent to the N-terminal caspase activation and recruitment domain (CARD) of MAVS aids in selecting administration of an anti-oxidative agent as a treatment for the subject. In some embodiments, the specific binding of the MAVS-binding agent to the N-terminal caspase activation and recruitment domain (CARD) of MAVS aids in selecting administration of at least one anti-oxidative agent as a treatment for the subject. In some embodiments, the anti-oxidative agent is MitoQ. In some embodiments, the anti-oxidative agent is a Szeto-Schiller (SS) peptide antioxidant. In some embodiments, the SS peptide is mitochondria-targeted tetra peptide (MTP) SS-31. In some embodiments, a means of determining the characteristic of the bound complex comprises measuring the level of the oligomerized MAVS polypeptide complex using any aspect of an h-FRET assay of the invention. In certain embodiments, a means of determining the characteristic of the bound complex comprises measuring a level of the cardiolipin (CL), wherein measuring the level of the CL comprises one or more of: determining presence of absence of CL and determining an amount of the CL.

According to another aspect of the invention, methods of preparing a bound complex comprising a serum mitochondrial antiviral-signaling (MAVS) oligomerized polypeptide complex and a MAVS-binding agent are provided. The methods including: contacting a MAVS-binding agent with a serum sample believed to be at risk of containing an oligomerized MAVS polypeptide complex, wherein the contact is under conditions suitable for the MAV-binding agent to form a bound complex with the oligomerized MAVS polypeptide complex. In certain embodiments, the method also includes determining a characteristic of the bound complex in the contacted serum sample. In some embodiments, the characteristic of the bound complex is one or more of the level of the bound complex and a physical property of the oligomerized MAVS polypeptide complex in the bound complex. In some embodiments, the physical property of the oligomerized MAVS polypeptide complex comprises the molecular weight of the oligomerized MAVS polypeptide complex. In certain embodiments, the molecular weight of the oligomerized MAVS polypeptide complex is determined to be one or more of: at least 200 kDa and between 250 kDa-1500 kDa. In some embodiments, the MAVS-binding agent is an antibody or functional fragment thereof that specifically binds the oligomerized MAVS polypeptide complex. In certain embodiments, the MAVS-binding agent specifically binds an N-terminal caspase activation and recruitment domain (CARD) of MAVS. In some embodiments, the oligomerized MAVS polypeptide complex comprises the oligomerized MAVS polypeptide and a phospholipid. In some embodiments, the phospholipid is cardiolipin. In some embodiments, the physical characteristic of the oligomerized MAVS polypeptide complex is the presence of the cardiolipin. In some embodiments, the MAVS-binding agent is an indirect MAVS-binding agent that binds the additional component of the bound complex. In some embodiments, the indirect MAVs-binding agent specifically binds one or more of: cardiolipin and an oligomerized MAVS polypeptide complex comprising cardiolipin. In some embodiments, the serum sample is a mammalian serum sample, optionally a human serum sample. In some embodiments, the method also includes using the determined characteristic to assist in identifying the presence of an autoimmune disease in the subject. In certain embodiments, the autoimmune disease is Systemic Lupus Erythematosus (SLE), atherosclerosis, Sjögren's syndrome, rheumatoid arthritis, asthma that is positive for type I IFN signature, dilated cardiomyopathy, cardiomyopathy, systemic sclerosis, Aicardi-Goutieres syndrome, type I diabetes, autoimmune thyroid disease, or neuromyelitis optica. In some embodiments, the method also includes using the determined characteristic to assist in one or more of: selecting a treatment for the subject and treating the subject. In some embodiments, the treatment comprises one or more of administering to the mammal: a pharmaceutical agent, a behavioral modification protocol, a diet modification protocol, a surgical procedure, and a physical therapy procedure. In some embodiments, the sample is from a subject and the specific binding of the MAVS-binding agent to the N-terminal caspase activation and recruitment domain (CARD) of MAVS aids in selecting administration of an anti-oxidative agent as a treatment for the subject. In some embodiments, the sample is from a subject and the specific binding of the MAVS-binding agent to the N-terminal caspase activation and recruitment domain (CARD) of MAVS aids in selecting administration of at least one anti-oxidative agent as a treatment for the subject. In certain embodiments, the anti-oxidative agent is MitoQ. In some embodiments, the anti-oxidative agent is a Szeto-Schiller (SS) peptide antioxidant. In some embodiments, the SS peptide is mitochondria-targeted tetra peptide (MTP) SS-31. In some embodiments, a means of determining the characteristic of the bound complex comprises measuring the level of the oligomerized MAVS polypeptide complex using the method of any aspect of an h-FRET assay method set forth herein. In some embodiments, a means of determining the characteristic of the bound complex comprises measuring a level of the cardiolipin (CL), wherein measuring the level of CL comprises one or more of determining presence of absence of CL and determining an amount of the CL.

According to yet another aspect of the invention, kits are provided. The kits including: a MAVS-binding agent that specifically binds an oligomerized MAVS polypeptide complex, and instructions for contacting the MAVS-binding agent with the oligomerized MAVS polypeptide complex under suitable conditions for the MAVS-binding agent and the oligomerized MAVS polypeptide complex to form a bound complex, and optionally instructions for determining a characteristic of the bound complex. In some embodiments, the MAVS-binding agent specifically binds an N-terminal caspase activation and recruitment domain (CARD) of MAVS. In certain embodiments, the characteristic of the bound complex is one or more of the level of the bound complex and a physical property of the oligomerized MAVS polypeptide complex in the bound complex. In some embodiments, the physical property of the oligomerized MAVS polypeptide complex comprises the molecular weight of the oligomerized MAVS polypeptide complex. In some embodiments, the oligomerized MAVS polypeptide complex comprises the oligomerized MAVS polypeptide and a phospholipid. In some embodiments, the phospholipid is cardiolipin. In some embodiments, wherein the physical characteristic of the oligomerized MAVS polypeptide complex is the presence of the cardiolipin. In some embodiments, the MAVS-binding agent is an indirect MAVS-binding agent that binds the additional component of the bound complex. In some embodiments, the indirect MAVS-binding agent specifically binds one or more of: cardiolipin and an oligomerized MAVS polypeptide complex comprising cardiolipin. In certain embodiments, a means of determining the characteristic of the bound complex comprises measuring the level of the oligomerized MAVS polypeptide complex using any aspect of an h-FRET assay method set forth herein. In some embodiments, the kit also includes one or more of a bead, a detectable label, a testing plate, a binding buffer, and an incubation solution. In some embodiments, the MAVS-binding agent comprises an antibody or functional fragment thereof the specifically binds an oligomerized MAVS polypeptide complex. In certain embodiments, the MAVS-binding agent specifically binds an N-terminal caspase activation and recruitment domain (CARD) of MAVS. In certain embodiments, a means of determining the characteristic of the bound complex comprises measuring a level of the cardiolipin (CL), wherein measuring the level of CL comprises one or more of determining presence of absence of CL and determining an amount of the CL.

According to another aspect of the invention, methods of treating an autoimmune disease in a subject are provided. The methods including: administering to a subject in need of such treatment an effective amount of a modulating compound that inhibits oligomerization of a mitochondrial antiviral-signaling (MAVS) polypeptide to reduce oligomerization of the MAVS polypeptide in the subject. In some embodiments, the modulating compound comprises a modulating agent. In certain embodiments, the means by which the modulating agent inhibits the MAVS polypeptide oligomerization comprises a direct interaction between the modulating agent and a MAVS polypeptide. In some embodiments, the modulating agent directly interacts with amino acid corresponding to residue C79 in the MAVS polypeptide sequence set forth as SEQ ID NO: 1. In some embodiments, the modulating agent inhibits formation of a disulfide bond in a polypeptide at one or more of (1) an amino acid that corresponds to residue C79 in the MAVS polypeptide sequence set forth as SEQ ID NO: 1 and (2) an amino acid that corresponds to residue C33 in the MAVS polypeptide sequence set forth as SEQ ID NO: 1. In some embodiments, the modulating agent comprises a polypeptide comprising an amino acid sequence set forth as one of SEQ ID Nos: 3-11, or a functional variant thereof. In certain embodiments, the functional variant has 95% or more sequence identity to at least one of SEQ ID NO: 3-11. In some embodiments, the modulating agent further comprises one or more of a delivery agent and a detectable label. In some embodiments, the modulating agent comprises a polypeptide comprising an amino sequence set forth as SEQ ID NO: 12-20, or a functional variant thereof. In certain embodiments, the functional variant has 85%, 86%, 87%, 88%, 89%, 90%, 91%, 92%, 93%, 94%, 95%, 96%, 97%, 98%, 99%, or 100% sequence identity to at least one of SEQ ID NO: 1-20. In some embodiments, the modulating agent comprises a MAVS polypeptide comprising one or more sequence modifications, wherein at least one sequence modification inhibits oligomerization of one or more MAVS polypeptides in the subject. In some embodiments, the method includes administering an effective amount of two or more modulating compounds to the subject. In some embodiments, the modulating agent comprises an antioxidant. In some embodiments, the modulating agent comprises: MitoQ or an SS peptide. In some embodiments, the SS peptide is SS-31. In some embodiments, the autoimmune disease is Systemic Lupus Erythematosus (SLE), atherosclerosis, Sjögren's syndrome, rheumatoid arthritis, asthma that is positive for type I IFN signature, dilated cardiomyopathy, cardiomyopathy, systemic sclerosis, Aicardi-Goutieres syndrome, type I diabetes, autoimmune thyroid disease, or neuromyelitis optica.

According to yet another aspect of the invention, methods of identifying a characteristic of a polypeptide in a test sample are provided. The methods including: (a) determining a level of a detectable label in an assay sample comprising a first binding compound comprising: a binding agent that specifically binds a polypeptide of interest, a bead, and a detectable label, wherein the binding agent is attached to the bead and to the detectable label, (b) contacting the assay sample of (a) with a test sample under conditions suitable for the first binding compound and the polypeptide of interest to form a bound complex; (c) determining a level of the detectable label in the contacted assay sample of (b); (d) contacting the contacted assay sample of (b) with a second binding compound, comprising a binding agent that specifically binds the polypeptide of interest and the detectable label, wherein the agent is attached to the detectable label; (e) determining a level of the detectable label of the contacted assay sample of (c); and (f) comparing the levels of the detectable label determined in steps (a), (c), and (e), wherein one or more differences between the levels of the detectable label determined in steps (a), (c) and (e) identify at least one characteristic of the polypeptide of interest in the test sample. In certain embodiments, the polypeptide of interest is an oligomerized polypeptide. In some embodiments, the characteristic of the polypeptide is the presence or absence of the polypeptide. In some embodiments, the characteristic of the polypeptide is one or more of: the molecular weight of the polypeptide and a level of oligomerization of the polypeptide. In certain embodiments, the binding agent comprises an antibody or functional fragment thereof that specifically binds the polypeptide of interest. In some embodiments, the bead is a metal bead. In certain embodiments, the bead is a silver bead and/or a gold bead. In some embodiments, the bead is a magnetic bead. In some embodiments, the first binding compound is attached to a surface. In certain embodiments, the attachment is between the bead and the surface. In some embodiments, the detectable label comprises a fluorescent molecule. In some embodiments, a lower level of fluorescence of the detectable label determined in step (c) compared to the level of fluorescence of the detectable label determined in step (a), indicates the presence of the polypeptide of interest in the test sample. In certain embodiments, the level of fluorescence of the detectable label determined in step (e) compared to the level of fluorescence of the detectable label determined in step (c), indicates a level of oligomerization of the polypeptide of interest in the test sample. In some embodiments, the test sample is a sample obtained from a subject. In certain embodiments, the polypeptide of interest is a MAVS polypeptide of interest. In some embodiments, the binding agent comprises an antibody or functional fragment thereof the specifically binds an oligomerized MAVS polypeptide complex. In some embodiments, the oligomerized MAVS polypeptide complex comprises at least one MAVS polypeptide having an amino acid sequence set forth as SEQ ID NO: 1 or a functional variant thereof. In certain embodiments, the binding agent specifically binds an N-terminal caspase activation and recruitment domain (CARD) of a MAVS polypeptide.

BRIEF DESCRIPTION OF CERTAIN OF THE SEQUENCES

SEQ ID NO: 1 is the amino acid sequence of the Homo sapiens mitochondrial antiviral signaling protein having GenBank Accession No.: AGF94754.1:

MPFAEDKTYKYICRNFSNFCNVDVVEILPYLPCLTARDQDRLRATCTLS

GNRDTLWHLFNTLQRRPGWVEYFIAALRGCELVDLADEVASVYQSYQPR

TSDRPPDPLEPPSLPAERPGPPTPAAAHSIPYNSCREKEPSYPMPVQET

QAPESPGENSEQALQTLSPRAIPRNPDGGPLESSSDLAALSPLTSSGHQ

EQDTELGSTHTAGATSSLTPSRGPVSPSVSFQPLARSTPRASRLPGPTG

SVVSTGTSFSSSSPGLASAGAAEGKQGAESDQAEPIICSSGAEAPANSL

PSKVPTTLMPVNTVALKVPANPASVSTVPSKLPTSSKPPGAVPSNALTN

PAPSKLPINSTRAGMVPSKVPTSMVLTKVSASTVPTDGSSRNEETPAAP

TPAGATGGSSAWLDSSSENRGLGSELSKPGVLASQVDSPFSGCFEDLAI

SASTSLGMGPCHGPEENEYKSEGTFGIHVAENPSIQLLEGNPGPPADPD

GGPRPQADRKFQEREVPCHRPSPGALWLQVAVTGVLVVTLLVVLYRRRL

H.

SEQ ID NO: 2 is amino acid sequence of Caspase activation and recruitment domain (CARD) of SEQ ID NO: 1 and includes amino acids 3 through 93 of SEQ ID NO: 1:

FAEDKTYKYICRNFSNFCNVDVVEILPYLPCLTARDQDRLRATCTLSGN

RDTLWHLFNTLQRRPGWVEYFIAALRGCELVDLADEVASVYQ.

SEQ ID NO: 3 CRIDVVDIIPYLSECL.

SEQ ID NO: 4 CLINQDQDCDEIRQI.

SEQ ID NO: 5 CRNFSNF.

SEQ ID NO: 6 ICRNFKAFSCDLAVRISILP.

SEQ ID NO: 7 RNFSNNVDVIIVQLNESVEI.

SEQ ID NO: 8 NVEVVDEILPY.

SEQ ID NO: 9 VEILPYLPC.

SEQ ID NO: 10 DVLIEVDILPFLPC.

SEQ ID NO: 11 ARDQDRLRATCTLSGNRDT

SEQ ID NO: 21 is TAT polypeptide sequence: GRKKRR QRRRPQ.

SEQ ID NO: 22 is forward primer: ccctgggggccatatt aatcc.

SEQ ID NO: 23 is reverse primer catcaaatcgcctccga gca.

BRIEF DESCRIPTION OF THE DRAWINGS

FIG. 1A shows results when wild-type (WT, closed symbols) and MAVS-deficient (KO, open symbols) MEFs were infected with CVB3 or SINV (multiplicity of infection (MOI)=1), or transfected with 1 μg 5'-ppp-RNA, and the total quantity of ROS was measured by FACS after 24 h using the oxidation-sensitive probe DHC (5 μM). FIGS. 1M & N shows measurements of basal respiration, maximal respiration, and spare respiratory capacity in MAVS-WT (closed bars) and MAVS-KO (open bars) MEFs.

FIG. 2A illustrates MAVS oligomerization in MAVS-WT or MAVS-KO MEFs after glucose oxidase (GOx) treatment (1 U/ml) or SINV infection for 6 h that was detected using semi-denaturing agarose gel electrophoresis. Data are representative of three experiments. FIG. 2B shows results when immunoprecipitation of MAVS was used to detect its association with TRAF2, TANK, TRADD, and RIPK1 following GOx treatment. FIG. 2C shows MAVS oligomerization in RIG-I-KO or RIG-I-KO/MDAS-knockdown (KD) MEFs in the absence or presence of GOx. FIG. 2D shows $\Delta\Psi_m$ using TMRE in response to GOx treatment or SINV infection as measured in MAVS-WT (black bars) and MAVS-KO (white bars) MEFs. The ionophore FCCP (10 nM) served as a control in WT and MAVS-deficient cells (bars overlap). Data are representative of at least three experiments. IFN-I (FIG. 2E) and IL-6 (FIG. 2F) cytokine secretion in response to GOx treatment was determined by ELISA in supernatants of MAVS-WT (black bars) and MAVS-KO (white bars) MEFs. In this study, ELISA assays were performed using cell culture supernatants (from MEFs) or serum from SLE patients and healthy controls. Because ELISAs are generally species-specific, data are presented as fold-changes rather than absolute concentrations to enable comparability. The fold change was calculated by comparison of mock and treated cells. At least three independent experiments are included in each graph. FIG. 2G shows results when the generation of total ROS in response to 10 nM MitoPQ was measured by FACS using DHC, and FIG. 2H shows corresponding MAVS-oligomerization that was detected by immunoblotting. FIG. 2I shows results of studies in which cell death induction by increasing concentrations of MitoPQ was determined by FACS using live-dead stain. IFN-I (FIG. 2J) and IL-6 (FIG. 2K) cytokine secretion by MAVS-WT (black bars) and MAVS-KO (white bars) MEFs induced by MitoPQ was measured by ELISA. Data are shown as mean±SEM, and are representative of three experiments. Statistical analyses performed were one-way ANOVA (D, I, J), followed by Sidak's Multiple Comparison Test to examine pair-wise differences, or Repeated Measures ANOVA (E), followed by Tukey's Multiple Comparisons Test to examine specific comparisons. (*$p<0.05$, **$p<0.005$)

FIG. 3A shows results when MAVS-WT MEFs were pre-treated with 100 μM MitoQ before treatment with GOx or SINV infection, and semi-denaturing gel electrophoresis was used to detect MAVS monomers and oligomers. dTTP (100 μM) which lacks the anti-oxidant quinol residue served as a negative control. FIG. 3B is a graph showing the ratio of MAVS oligomers to monomers after GOx treatment or SINV infection, with or without MitoQ pre-treatment, was determined by densitometric measurement of immunoblots. FIG. 3C shows results when $\Delta\Psi_m$ in MEF after GOx+/−MitoQ and SINV+/−MitoQ treatment was measured by FACS using TMRE. FIG. 3D shows IFN-I secretion of MEF with or without MitoQ and GOx treatment or SINV infection as measured in cell culture supernatants using ELISA. Data shown are representative of three experiments, and bar graphs are mean±SEM. Statistical analyses performed were two-way ANOVA (FIGS. 3B & D), followed by Tukey's Multiple Comparisons Test to examine specific comparisons or one-way ANOVA (FIG. 3C), followed by Sidak's Multiple Comparison Test to examine pair-wise differences. (*$p<0.05$, **$p<0.005$).

FIG. 4A shows results of study in which freshly isolated human PBMCs were treated with GOx for the times indicated, and semi-denaturing agarose gel electrophoresis was used to detect MAVS oligomerization. Cells (MitoQ) or cell lysates (β-Me) were pretreated as indicated. Findings are representative of three experiments. FIG. 4L-N shows OCR measurements from whole PBMC (FIG. 4L), B cells (FIG. 4M), or T cells (FIG. 4N) of SLE patient (black bars) or healthy control (white bars). Findings are representative of three patients and three controls. Statistical analyses performed were Independent t-tests (FIG. 4D, E, G-J), two-way ANOVA (FIG. 4L-N) and Pearson's Correlation Coefficient (F). (*$p<0.05$, $p<0.005$, *$p<0.0005$, ****$p<0.00005$).

FIG. 5A shows results of a study in which MAVS-WT MEFs, or MAVS-KO MEFs expressing either human MAVS-WT or the MAVS-C79F SNP or combination of both, were infected with SINV, or exposed to GOx. MAVS aggregation was determined using 5% semi-denaturing TGX gels in sample buffer in presence or absence of 0.1% of β-Me, allowing detection of oligomers and intermediate lower molecular weight MAVS oligomers following immunoblotting. Data represent one of at least three experiments. FIG. 5B-E show quantitation of MAVS oligomers (FIG. 5B), IFN-I production (FIG. 5C), ROS (FIG. 5D), and mitochondrial membrane potential (FIG. 5E) from the same samples as in (FIG. 5A). FIGS. 5F & G show results of semi-denaturating, 1.5% agarose gel analysis (FIG. 5F) and densitometry (FIG. 5G) of MAVS oligomers from plasma of healthy controls, SLE MAVS-C79F and SLE MAVS-WT patients that were taken and frozen at the same time; the total of high weight oligomers (above 1000 kDa) were analyzed in 4 independent experiments and normalized to the level of detectable albumin in plasma. Statistical analyses performed were two-way ANOVA (FIG. C-E), including interaction terms, followed by Tukey's Multiple Comparisons Test to examine specific comparisons or one-way ANOVA (FIG. 5G), followed by Sidak's Multiple Comparison Test to examine pair-wise differences. (*$p<0.05$, **$p<0.005$).

FIG. 6A is a diagram of an experimental design for the purification of MAVS oligomers from the plasma of SLE patients, and for the de novo reconstitution of SLE-MAVS oligomers with purified mitochondria from MAVS-WT MEFs, MAVS-KO MEFS, and MAVS-KO MEFs reconstituted with WT and/or C79F MAVS. MAVS antibody was covalently linked by Disuccinimidyl suberate (DSS) to protein G magnetic beads to precipitate MAVS oligomers. Similarly, mitochondria from MAVS-WT, MAVS-KO, and MAVS-C79F MEFs were isolated with Tom22 antibody-conjugated magnetic beads. FIG. 6B shows quality and purity of MAVS oligomers precipitated from SLE patient plasma (samples P1-P4) and assessed using gel electrophoresis. Plasma from a healthy individual (C1) served as a control. FIG. 6C shows results when mitochondria from MAVS-WT and MAVS-KO MEFs were untreated or treated with GOx or MitoQ, and exposed to patient-derived MAVS oligomers. Mitochondrial lysates were then separated during gel electrophoresis and subsequent immunoblots were probed for the presence of MAVS oligomers. FIG. 6D shows results when purified mitochondria harboring the MAVS-C79F variant or a mix of MAVS-WT and MAVS-C79F were also exposed to purified MAVS from an SLE patient (P2).

FIG. 7A shows results when SLE patient plasma-derived MAVS oligomers were labeled with Alx546 or Alx488 fluorophores. Gel electrophoresis confirmed labeling efficiency by direct excitation of the in-gel fluorescence of control (C1-C4) and patient (P1-P4) samples (upper panels). FIG. 7B shows results when murine BMDCs or human monocyte-derive DCs (hDC) were cultivated with either SLE patient-derived fluorescent MAVS oligomers (P3) or plasma from a healthy control subject (C1). Shown are confocal microscopic images analyzing the localization of internalized Alx546-labeled MAVS oligomers. MitoTracker green (50 nM) and Hoechst 33342 (10 μg/ml) were used to define mitochondria and nuclei, respectively. FIG. 7C are results obtained when MAVS internalization kinetics was calculated by measuring increase in intracellular Alx546 fluorescence intensity over time as a ratio (P3/C1) following exposure to either SLE patient (P3) or healthy control (C1) labeled MAVS. Data are expressed as mean±SEM. FIG. 7D provides correlation coefficients for mitochondria (MitoTracker green) and Alx546-labeled MAVS oligomers that were calculated to determine the co-localization of mitochondria and MAVS oligomers. For data collection, 200 individual cells were examined. FIG. 7E shows results when IFN-I secretion in response to MAVS internalization from SLE patients (P2-P4) or healthy controls (C1, C2) using BMDC from WT or MAVS-KO mice was measured by ELISA. FIG. 7F shows MAVS oligomerization in the mitochondrial fraction of BMDCs, which were exposed to SLE patient-derived and fluorescently labeled MAVS (top panel). Total mitochondrial MAVS was detected following treatment with reducing agent β-Me. The interaction of the patient-derived MAVS-oligomers with mitochondria was confirmed by the detection of the fluorophore using an anti-Alx488 antibody or direct in-gel fluorescence (middle panel). Mitochondrial BMDC fractions from mice lacking MAVS served as controls (lower panels). FIG. 7G shows results of a study to verify that neither MAVS expression nor MAVS oligomerization could be induced by the fluorophore alone, in which BMDCs were treated with increasing concentrations of free Alx488 dye and the mitochondrial fraction was probed for the amount of MAVS at mitochondria, and Alx488 was detected by anti-Alx488 antibody. FIG. 7H provides results of a study in which the mitochondrial fraction of BMDCs exposed to SLE patient (P2-P4) and control (C1) plasma-derived MAVS oligomers was immunoblotted to determine recruitment of signaling molecules downstream of MAVS activation. Shown immunoblots are representative of three experiments. Statistical analyses performed were two-way ANOVA (FIG. 7C-E), followed by Tukey's Multiple Comparisons Test to examine specific comparisons. (**$p<0.005$).

FIG. 8A shows the generation of mROS in WT, MAVS-deficient, reconstituted, or minimal-MAVS (truncated at position Gln148) expressing MEF in response to infection with CVB3 or SINV, or transfection with 5'-ppp-RNA, as quantified by FACS using 50 nM MitoSox Red. FIG. 8B shows flow cytometric quantification of total mitochondrial mass in these cells that was achieved by MitoTracker DeepRed. FIG.

8C illustrates result when the basal extracellular acidification rate (ECAR), a readout of lactate production by glycolysis, was measured by Seahorse Flux Analyzer. FIG. 8D shows the ultrastructural morphology of mitochondria in WT and MAVS-deficient MEFs following infection as observed by transmission electron microscopy. FIG. 8E shows results when the dimensions of WT and MAVS-deficient mitochondria were calculated from representative electron microscopic images, and the percentage of elongated mitochondria was calculated from 5 micrographs.

FIG. 9A shows results when freshly prepared PBMC were treated with GOx or infected with SINV, and subsequently homogenized in buffer containing 100 µM iodoacetamide. FIG. 9B shows results when PBMC of SLE patients (n=9) and healthy, sex- and age matched control donors (n=9) were isolated by Ficoll gradient centrifugation as described, and cells and corresponding plasma samples were supplemented with 100 µM iodoacetamide before analysis.

FIG. 11 is a table that provides genotype and activity of SLE patients. MAVS oligomerization and IFN-I change were normalized among all 17 patients, where the highest patient value was defined as 1. MAVS oligomerization and IFN-I per patient were scored with +, ++, +++, ++++, when the absolute mean value after normalization was falling between 0 and 0.25, 0.25 and 0.5, 0.5 and 0.75 or 0.75 and 1.00 respectively. (nd—not determined)

FIG. 14A is a blot showing that MAVS oligomerization either induced by 5'-ppp-RNA or induced with treatment with GOx resulted in lower levels of phosphorylated Drp1 at mitochondria, in contrast to higher levels in the same cells pre-treated with MitoQ. FIG. 14B shows densitometry results that indicated changes in the level of Drp1$^{616p}$ at mitochondria. Densitometry values normalized to the level of Cox IV.

FIG. 15A shows the higher level of CL-MAVS binding in the SLE sample. FIG. 15B is a blot showing results of studies performed to test MAVS oligomers interaction with various peptides. The results show the MAVS oligomer and CL interaction. The peptides tested were: TAG, triacylglycerol; DAG, diacylglycerol; PA, phosphatidic acid; PS, phosphatidylserine; PE phosphatidylethanolamine; PC, phosphatidylcholine; PG, phosphatidylglycerol; CL, cardiolipin, PI, phosphatidylinositol; PIP, phosphatidylinositol phosphate; PIP2, phosphatidylinositol biphosphate; PIP3, phosphatidylinositol triphosphate; CHO, cholesterol; SM, sphingomyelin; CER, ceramide.

DETAILED DESCRIPTION

Figure 1A:
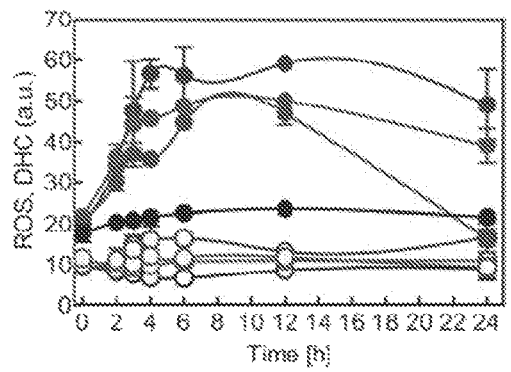
FIG. 1A-P shows provides graphs, gel images, and photomicroscopic images demonstrating that MAVS oligomerization induces ROS generation and regulates cellular metabolism.
Figure 1B:
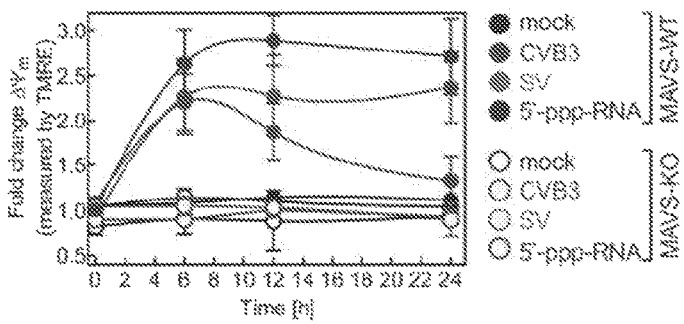
FIG. 1B in parallel, shows results when the mitochondrial transmembrane potential ($\Delta\Psi_m$) was monitored using TMRE (25 nM). FACS data are mean (+/−SEM) of triplicate samples and are representative of three separate experiments.
Figure 1C:
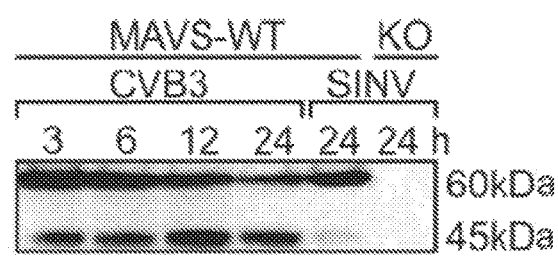
FIG. 1C indicates results when the kinetics of MAVS cleavage in CVB3-infected MEFs was determined by immunoblotting. SINV-infected and MAVS-KO MEF served as controls. Data are representative of three independent experiments.

Systemic lupus erythematosus (SLE) is a complex autoimmune disease associated with multiple immunologic abnormalities, among which upregulation of type I interferon (IFN-I) genes correlates strongly with disease activity. It has now been identified that mitochondrial antiviral signaling protein (MAVS), which normally forms a complex with retinoic acid gene I (RIG-I)-like helicases during viral infection, can be activated by oxidative stress alone. It is now known that MAVS oligomerization on the surface of the mitochondrial outer membrane by oxidative stress leads to mitochondrial hyperpolarization, decreased ATP production, and increased spare respiratory capacity. This virus-independent oligomerization of MAVS also leads to the secretion of IFN-I and proinflammatory cytokines. Consistent with this, inhibition of mitochondrial reactive oxygen species (ROS) by the mitochondria-targeted antioxidant MitoQ prevents oligomerization of MAVS. It has now been shown that MAVS is spontaneously oligomerized in peripheral blood mononuclear cells of SLE patients, but not in sex- and age-matched healthy control individuals. In addition, ROS-mediated MAVS oligomerization and IFN-I production has now been identified as greatly reduced in cells expressing a MAVS-C79F variant that occurs in 30% of healthy sub-Saharan Africans and has been linked with reduced expression of IFN-I and milder SLE. Methods and compounds of the invention are based, in part of the discovery that spontaneous MAVS oligomerization due to mitochondrial oxidative stress in SLE and other autoimmune diseases contributes to the IFN-I signature characteristic of this syndrome.

The invention is based, in part, on the discovery that MAVS oligomerization leads to decreased mitochondrial biogenesis and a higher mitochondrial membrane potential, resembling the mitochondrial phenotype observed in T cells of SLE patients. It is now been shown that oxidative stress, either in the presence or absence of viral infection, induces MAVS oligomerization, leading to significant IFN-I production and that the spontaneous MAVS oligomerization can be inhibited, for example though not intended to be limiting, by the mitochondria-targeted antioxidant MitoQ and other inhibitory agents and compounds.

The invention, in part, relates to compounds and methods that can be used to identify autoimmune diseases in cells and/or subjects. The role of mitochondrial antiviral signaling (MAVS) polypeptides has been examined and it has now been identified that information about one or more characteristics of an oligomerized MAVS polypeptide complex in a cell and/or subject can aid in identifying the presence of an autoimmune disease in a cell and/or subject and selecting a treatment for an autoimmune disease in a cell and/or subject. In addition, certain aspects of the invention include compounds for treating autoimmune diseases and methods of their use in such treatments in cells and/or subjects.

Characteristics of an oligomerized MAVS polypeptide complex that may be determined using methods of the invention include but are not limited to: (1) the presence or absence of an oligomerized MAVS polypeptide complex; (2) an amount or level of an oligomerized MAVS polypeptide complex; (3) a degree or level of oligomerization of MAVS polypeptides in an oligomerized MAVS polypeptide complex, (4) a molecular weight of an oligomerized MAVS polypeptide complex, (5) a size of an oligomerized MAVS polypeptide complex, and (6) other identified physical features of an oligomerized MAVS polypeptide complex. In certain aspects of the invention, a physical feature of an oligomerized MAVS polypeptide complex is it being bound to a phospholipid or to a polypeptide that is not a MAVS polypeptide. A non-limiting example of a phospholipid that in some aspects of the invention is bound to and thus considered as part of an oligomerized MAVS polypeptide complex is a cardiolipin (CL) phospholipid. As used herein the term "characteristics of an oligomerized MAVS polypeptide" means one or more of characteristics (1)-(6) listed above herein.

As used herein, the term "oligomerized MAVS polypeptide complex" means a multimer of a MAVS polypeptide that may include from 2-10, 2-20, 2-50, 2-100, 5-10, 5-20, 5-50, 5-100, 10-50, or 10-100, or more MAVS polypeptides that are physically associated with each other, thereby forming a complex of physically associated MAVS polypeptides. The number of MAVS polypeptides in an oligomerized MAVS polypeptide complex may also be referred to herein as a degree or level of oligomerization or polymerization of an oligomerized MAVS polypeptide complex.

Another characteristic of an oligomerized MAVS polypeptide complex that may be determined using methods of the invention is the molecular weight (MW) of an oligomerized MAVS polypeptide complex. The MW of an oligomerized MAVS polypeptide complex may be at least 200 kDa, 250 kDa, 300 kDa, 350 kDa, 400 kDa, 450 kDa, 500 kDa, 550 kDa, 600 kDa, 650 kDa, 700 kDa, 750 kDa, 800 kDa, 850 kDa, 900 kDa, 950 kDa, 1000 kDa, 1200 kDa, 1300 kDa, 1400 kDa, 1500 kDa, or more.

As used herein, the terms "oligomerized MAVS polypeptide complex" and "MAVS oligomers" are used interchangeably and mean a complex of physically associated MAVS polypeptides. The term "physically associated" used herein in context of an oligomerized MAVS polypeptide complex means individual MAVS polypeptides, for example MAVS polypeptides having the amino acid sequence set forth as SEQ ID NO: 1, or functional variants thereof, that oligomerize or polymerize with other MAVS polypeptides or functional variants thereof, thereby forming a complex of the MAVS polypeptides. It will be understood that in some embodiments of the invention, an oligomerized MAVS polypeptide complex may be one or more of: bound to, attached to, and associated with a phospholipid or a polypeptide that is not a MAVS polypeptide.

Oligomerized MAVS Polypeptide Assays and Assessment

Methods of the invention, in some aspects, permit assessment of characteristics of a mitochondrial antiviral-signaling (MAVS) oligomerized polypeptide complex in a sample from a cell and/or subject. Certain aspects of the invention include methods of assessing samples for oligomerized MAVS polypeptide complexes. Such methods may include contacting a sample with a MAVS-binding agent under conditions suitable for the MAVS-binding agent to bind to an oligomerized MAVS polypeptide complex present in the sample. Under such conditions the MAVS-binding agent and the oligomerized MAVS polypeptide complex form what is referred to herein as a "bound complex", which can be detected, permitting assessment of one or more characteristics of the oligomerized MAVS polypeptide complex of the sample. It will be understood that characteristics of an oligomerized MAVS polypeptide in a sample will correspond to and can be extrapolated to identify characteristics of the oligomerized MAVS polypeptide complex in the source from which the sample was obtained.

In certain aspects of the invention, methods of determining a characteristic of a oligomerized MAVS polypeptide complex comprises determining the presence or absence of another molecule, such as a phospholipid that is bound to or associated with the oligomerized MAVS polypeptide complex, but that is not a MAVS polypeptide. For example, though not intended to be limiting, an oligomerized MAVS polypeptide complex may be bound to a cardiolipin (CL) phospholipid and determining a characteristic of the oligomerized MAVS polypeptide complex may comprise determining the presence, absence, level or other measure of a CL phospholipid in a sample, such as a serum sample. Such methods may include contacting a sample with a MAVS-binding agent under conditions suitable for the MAVS-binding agent to bind to an oligomerized MAVS polypeptide complex present in the sample. In some aspects an agent that binds to CL is considered to be a MAVS-binding agent because it binds indirectly with the oligomerized MAVS. Under such conditions the MAVS-binding agent that indirectly binds the oligomerized MAVS and the oligomerized MAVS polypeptide complex form what is referred to herein as a "bound complex", which can be detected, permitting assessment of one or more characteristics of the oligomerized MAVS polypeptide complex of the sample. Further the CL in complex with MAVS or any other phospholipid in the complex—bound with MAVS can be oxidized.

With respect to characteristics of an oligomerized MAVS polypeptide complex, an assessment method of the invention that results in no detection (for example a zero amount or level) of a bound complex that normally would be formed by contacting an oligomerized MAVS polypeptide complex with the MAVS-binding agent under suitable (also referred to herein as "appropriate") conditions indicates the absence of the oligomerized MAVS polypeptide complex in the sample. Any detected bound complex that would be formed by an oligomerized MAVS polypeptide complex and a MAVS-binding agent under appropriate conditions, indicates the presence of the oligomerized MAVS polypeptide complex in the sample. Additional methods of the invention may be used to determine the amount or level of an oligomerized MAVS polypeptide complex by detecting a level of the bound complex formed following contact of the sample with a MAVS-binding agent.

Methods and compounds of the invention that can be used to determine (also referred to herein as "to identify") a characteristic an oligomerized MAVS polypeptide complex in a sample, cell, tissue, and/or subject, may be used to identify the presence/absence or status of an autoimmune disease in the cell, tissue, or subject. Such methods of the invention may be used in identifying an autoimmune disease or risk of an autoimmune disease. For example, though not intended to be limiting, in certain embodiments of the invention an autoimmune disease may be identified, in part, by the presence of an abnormal (e.g., increased) level of oligomerized MAVS polypeptide complexes in a sample, cell, and/or subject. With respect to an oligomerized MAVS polypeptide complex level in a sample, as used herein a "normal" level may be no detected oligomerized MAVS polypeptide complex as determined using a method of the invention. An "abnormal" level is defined as a level of detected oligomerized MAVS polypeptide complex that is higher than a normal level of the oligomerized MAVS polypeptide complex as determined using a method of the invention. As used herein, with respect to a level of an oligomerized MAVS polypeptide complex, a MAVS polypeptide or encoding polynucleotide, an inhibitory agent or compound, or other molecule described herein, the terms: "increased", "elevated", and "higher" are used interchangeably, and the terms "decrease", "reduced", and "lower" are used interchangeably.

Methods and assays set forth in certain embodiments of the invention can be used to identify the status of, and to evaluate and compare one or more characteristics of an oligomerized MAVS polypeptide complex in a sample, or in some embodiments of the invention, in a cell and/or subject. Methods in some aspects of the invention may include detecting in a sample one or more characteristics of an oligomerized MAVS polypeptide complex. Information obtained using methods of the invention can be used to identify the status of an autoimmune disease in a sample, cell, and/or subject and may be used to aid in selecting a treatment for a cell and/or a subject found to have or to be at risk of having an autoimmune disease.

As used herein the term "status" with respect to an oligomerized MAVS polypeptide complex in a sample, may be used in reference of one or more characteristics of the oligomerized MAVS polypeptide complex in the sample. In certain embodiments of the invention the status of an oligomerized MAVS polypeptide complex in a sample is binary, and is determined to be either present or absent using a method of the invention. In certain embodiments of the invention, a status may be a level or amount of an oligomerized MAVS polypeptide complex in a sample, and may be a difference between the levels in two or more samples, and or between a sample and a control. In some aspects of the invention, a determination of a level of an oligomerized MAVS polypeptide complex that is greater than zero in a sample indicates the presence of an autoimmune disease in the sample and in the source from which the sample was obtained. In some embodiments the source from which a sample is obtained is a cell, a cell culture, and/or a subject. In certain aspects of the invention, a status of an oligomerized MAVS polypeptide complex in a sample may be used to determine a status of an oligomerized MAVS polypeptide complex and associated autoimmune disease a subject from whom the sample was obtained. In certain aspects of the invention, methods of identifying an oligomerized MAVS polypeptide complex that comprises an additional molecule, such as a phospholipid (for example CL, or another phospholipid) or a polypeptide bound to the oligomerized MAVS polypeptide can be used to assess a status of a disease or condition, non-limiting examples of which are: SLE, atherosclerosis, Sjörgen syndrome, and asthma that is positive for type I IFN signature, dilated cardiomyopathy, cardiomyopathy, systemic sclerosis, Aicardi-Goutieres syndrome, type I diabetes, autoimmune thyroid disease, and neuromyelitis optica. In a non-limiting example, an antibody or other agent that specifically binds CL and/or an oligomerized MAVS polypeptide complex comprising CL can be used to detect and determine a characteristic of the oligomerized MAVS polypeptide complex. The presence of an oligomerized MAVS polypeptide complex comprising CL may indicate the presence of a disease or condition and/or can be used in methods to assess severity, prognosis, etc. of a disease or condition. In some aspects of the invention, a determination of a level of an oligomerized MAVS polypeptide complex comprising a CL phospholipid that is greater than zero in a sample indicates the presence of an autoimmune disease in the sample and in the source from which the sample was obtained. In certain aspects of the invention, a determination of a level of an oligomerized MAVS polypeptide complex comprising a CL phospholipid that is greater in a sample than a control level indicates the presence of an autoimmune disease in the sample and in the source from which the sample was obtained.

In certain aspects of the invention, methods are provided that can be used to distinguish between high-level I IFN signature diseases and conditions such as, but not limited to: Neuromyelitis optica and CNS Sjögren's disease and low-level I IFN signature type multiple sclerosis. For example, a control value for a level of oligomerized MAVS polypeptide complex in a high-level I IFN signature disease or condition and a control value for a level of oligomerized MAVS polypeptide complex in a low-level I IFN signature disease or condition can be compared to a level of oligomerized MAVS polypeptide complex in a sample obtained from a subject. The comparison permits identification of a level in the sample as indicating the presence of the high-level I IFN signature disease or condition or the presence of the low-level I IFN signature disease or condition in the subject.

As used herein the term "status" with respect to an autoimmune disease may mean presence, absence, onset, end, recurrence, progression, regression, increase, decrease, or other indication of the state of the autoimmune disease associated with the presence of an oligomerized MAVS polypeptide complex. For example, in certain embodiments of the invention, a status may be the state of progression of an autoimmune disease, which can be determined by testing a first sample obtained from a subject and testing a second sample obtained from the subject, wherein the second sample is obtained from the subject at a later point in time. An increase or other change in one or more characteristics of an oligomerized MAVS polypeptide complex determined in the second sample compared to the characteristic determined in the first sample may indicate the status of progression or increase of the autoimmune disease of the subject. A determination of a level of zero of an oligomerized MAVS polypeptide complex in a first sample obtained from a subject followed by a determination of a level greater than zero of the oligomerized MAVS polypeptide complex in a sample subsequently obtained from the subject may indicate a status of onset of the autoimmune disease in the subject. Similarly, a decrease in the level of an oligomerized MAVS polypeptide complex determined in a sample obtained from a subject at a later time point compared to that determined in a sample obtained from the subject at an earlier time point would indicate a status of regression or decrease of the autoimmune disease—which in some aspects of the invention, may result from administering a treatment method of the invention to subject.

Methods of the invention, in some embodiments, may include detecting characteristic of an oligomerized MAVS polypeptide complex in a sample and comparing the detected level to one or more of: a level of zero, a control level, and a prior level in a sample from obtained the same source. A determination of a level of an oligomerized MAVS polypeptide complex that is greater than zero in a first sample obtained from a cell and/or subject followed by determination of a lower level of the oligomerized MAVS polypeptide complex in a sample subsequently obtained from the cell and/or subject, respectively, indicates a status of the autoimmune disease of the cell and/or subject, respectively, as ended or resolved. In some embodiments of the invention detection in a sample of an amount of an oligomerized MAVS polypeptide complex greater than zero identifies the status of the source (for example, the subject) of the sample as having an autoimmune disease. In certain embodiments of the invention, any detected level of an oligomerized MAVS polypeptide complex that is greater than zero in a sample need not be compared to a control because a level greater than zero confirms the presence of the oligomerized MAVS polypeptide complex, and the autoimmune disease in the source of the sample.

In certain aspects of the invention, a characteristic of an oligomerized MAVS polypeptide complex in a cell, cell culture, and/or a subject can be detected using methods of the invention to measure the oligomerized MAVS polypeptide complex for example, using one or more detectably labeled MAVS-binding agents in an in vitro assay of a sample obtained from the cell, cell culture, and/or subject, respectively. As used herein, the term "measure" used in reference to measuring a characteristic of an oligomerized MAVS polypeptide complex means: (a) determining a quantitative value, such as an amount, weight, concentration, relative amount, relative concentration, etc., of an oligomerized MAVS polypeptide complex; or (b) determining the "presence" or "absence" of an oligomerized MAVS polypeptide complex. Means for measuring a characteristic of oligomerized polypeptides are known in the art. Non-limiting examples of measuring means are provided herein.

Detection methods suitable for use in certain embodiments of methods of the present invention can be used to identify and measure a characteristic of an oligomerized MAVS polypeptide complex in samples in vitro as well as in vivo. For example, in certain embodiments of the invention in vitro techniques for detecting, identifying, and/or measuring a characteristic of an oligomerized MAVS polypeptide complex include but are not limited to: antibody binding and detection, microscopy, protein separation methods, visualization methods, etc. In certain aspects of the invention in vitro techniques for detecting, identifying, and/or measuring a characteristic of an oligomerized MAVS polypeptide complex may include detection of a detectably labeled antibody or fragment thereof that selectively binds an oligomerized MAVS polypeptide complex. In vitro techniques for detecting, identifying, and/or measuring a characteristic of an oligomerized MAVS polypeptide complex in certain embodiments of the invention include, but are not limited to: homo-FRET assays of the invention, enzyme linked immunosorbent assays (ELISAs), Western blots, immunoprecipitations, immunofluorescence, and other suitable techniques.

Controls

In some embodiments of the invention, methods may include comparing a characteristic of an oligomerized MAVS polypeptide complex in a sample to a control value of the characteristic of an oligomerized MAVS polypeptide complex. As used herein a "control" may be a normal control or an autoimmune disease control. Selection and use of appropriate controls in comparative, diagnostic, treatment, and assay methods are well known in the art. In some embodiments of the invention, a normal control level may zero and represent the amount in a subject and/or cell that is free of an oligomerized MAVS polypeptide complex. A control level of a characteristic of an oligomerized MAVS polypeptide complex can readily be determined by measuring level or oligomerization, an amount or level, size, molecular weight or other physical characteristic of an oligomerized MAVS polypeptide complex using a method of the invention, as described herein. In some embodiments of the invention, an autoimmune disease control level may be obtained from a sample from a subject or cell known have the autoimmune disease. In some embodiments, a disease control level, size, molecular weight or other physical characteristic of an oligomerized MAVS polypeptide complex may be based on levels obtained from one or more subjects and/or cells known to have the autoimmune disease. In certain embodiments of the invention, the disease control may be a sample from a subject diagnosed with an autoimmune disease and the subject's disease control may be compared to another sample obtained from the subject at a different time. In certain embodiments of the invention, a disease control level of a characteristic of an oligomerized MAVS polypeptide complex can readily be determined by measuring the characteristic of an oligomerized MAVS polypeptide complex in a sample obtained from a subject known to have an autoimmune disease. As a non-limiting example, a control may be a level or range of levels of an oligomerized MAVS polypeptide complex determined in a sample or samples obtained from a subject or subjects known to have a high-level I IFN signature disease such as, but not limited to: Neuromyelitis optica and CNS Sjögren's and another control may be a level or range of levels of an oligomerized MAVS polypeptide complex determined in a sample or samples obtained from a subject or subjects known to have a low-level I IFN signature type disease, for example, multiple sclerosis.

In some embodiments of the invention, a control characteristic of an oligomerized MAVS polypeptide complex is the characteristic of an oligomerized MAVS polypeptide complex determined from samples, cells, and/or subjects that do not have the autoimmune disease that is being tested for in the sample. For example, in some embodiments, a control characteristic of an oligomerized MAVS polypeptide complex is a level of the characteristic determined in a normal sample that does not have an autoimmune disease that is suspected to be in the sample obtained from the subject and/or cell. In such a case, the presence of the autoimmune disease can be determined based on an increase in the level of an oligomerized MAVS polypeptide complex in the subject and/or cell sample as compared to the control that is free of the oligomerized MAVS polypeptide complex. In another embodiment of the invention, the control is from a normal subject or cell and the test sample is from a subject or cell that is suspected of having the autoimmune disease associated with an oligomerized MAVS polypeptide complex.

Subject, Diseases, and Cells

As used herein, a subject shall mean a vertebrate animal including but not limited to a human, mouse, rat, guinea pig, rabbit, cow, dog, cat, horse, goat, and primate, e.g., monkey. In certain aspects of the invention, a subject may be a domesticated animal, a wild animal, or an agricultural animal. Thus, the invention can be used to treat diseases or conditions in human and non-human subjects. For instance, methods and compositions of the invention can be used in veterinary applications as well as in human prevention and treatment regimens. In some embodiments of the invention, the subject is a human. In some embodiments of the invention, a subject has one or more autoimmune diseases.

Autoimmune diseases associated with abnormal oligomerized MAVS polypeptide complexes that may be identified and treated with methods and compounds of the invention include, but are not limited to: Systemic Lupus Erythematosus (SLE), atherosclerosis, Sjögren's syndrome, rheumatoid arthritis, asthma that is positive for type I IFN signature, dilated cardiomyopathy, cardiomyopathy, systemic sclerosis, Aicardi-Goutieres syndrome, type I diabetes, autoimmune thyroid disease, and neuromyelitis optica.

Cells that may be assayed and/or treated using methods and compounds of the invention include but are not limited to mammalian cells, human cells, non-human mammalian cells, cultured cells, connective tissue cells, epidermal cells, kidney cells, cardiac cells, respiratory system cells, circulatory system cells, and nervous system cells, immune system cells, dendritic cells, T cells, macrophages, B cells, neutrophils, monocytes, platelets, and blood plasma and serum.

A cell that is assayed or treated using a method, compound, or composition of the invention may be in vitro or in vivo. An in vivo cell may be in a subject. As used herein the term "one or more" when used in reference to a cell means a single cell or a plurality of cells. A plurality of cells includes at least 2, 3, 4, 5, 6, 7, 8, 9, 10, 20, 50, 100, 500, 1,000, 5,000, 10,000, 50,000, 100,000, 500,000, 1,000,000, or more cells, including all integers in between. In some aspects of the invention a cell or plurality of cells may be in cell culture or may be in a subject. A plurality of cells may be a homogeneous or heterogeneous set of cells. As used herein, a homogeneous plurality of cells means a plurality of cells in which one or more cell characteristics of interest are the same for all of the cells in the plurality. It will be understood that a homogeneous plurality of cells may be considered to be homogeneous on the basis that each of the cells has the one or more characteristics of interest that are the same, but the cells need not be entirely identical and features or characteristics other than the characteristics of interest may differ in different cells of the plurality. For example, a plurality of cells may be referred to as homogeneous if (1) all of the cells naturally express a MAVS molecule or (2) none of the cells naturally express a MAVS molecule, irrespective of other similarities or differences between the cells in the plurality. As used herein a heterogeneous plurality of cells means a plurality of cells in which one or more cell characteristics of interest are different in different cells. For example, a plurality of cells may be referred to as heterogeneous if one or more of the cells in the plurality naturally express a MAVS molecule and one or more of the cells do not naturally express a MAVS molecule, irrespective of other similarities or differences between the cells in the plurality. In certain aspects of the invention, a plurality of cells is in a subject. It will be understood that a cell may naturally express different amounts of MAVS molecules at different stages and times. For example, an endogenous MAVS polypeptide or its encoding polynucleotide may not be expressed in a cell at certain stages of the cell's life and may be expressed at other stages in the cell's life. Thus, a plurality of cells may include cells that currently have an endogenous MAVS molecule and other cells that do not have an endogenous MAVS molecule and the composition of the plurality of cells with respect to the presence of one or more endogenous MAVS molecules and/or oligomerized MAVS polypeptide complexes may change at different stages of an autoimmune disease. In some aspects of the invention, plurality of cells may be a homogenous plurality or a heterogeneous plurality with respect to expression of one or more MAVS molecules and the plurality of cells may change between being homogeneous and heterogeneous at different stages of an autoimmune disease the cells in the plurality.

Treatment Methods and Compounds

Certain aspects of the invention include methods and compounds to treat an autoimmune disease in a subject. Embodiments of treatment methods of the invention may include administration to a subject in need of such treatment, an effective amount of a modulating compound that inhibits oligomerization of a mitochondrial antiviral-signaling (MAVS) polypeptide to reduce oligomerization of the MAVS polypeptide in the subject. A subject in need of such treatment may be a subject known to have, or believed to be at risk of having, an autoimmune disease that is associated with abnormal oligomerized MAVS polypeptide complexes. A modulating compound useful in methods of the invention may be compound that comprises an agent that modulates the amount or level of oligomerization of a MAVS polypeptide or another characteristic of an oligomerized MAVS polypeptide complex. A modulating agent that reduces oligomerization of a MAVS polypeptide may be a useful modulating agent in certain aspects of the invention. A modulating agent that reduces a characteristic of abnormal oligomerization of a MAVS polypeptide complex may be a useful modulating agent in certain aspects of the invention.

Non-limiting examples of subjects to which methods and compounds of the present invention can be applied are subjects who are diagnosed with, suspected of having, or at risk of having one or more autoimmune diseases, such as an autoimmune disease associated with an abnormal MAVS oligomerization. Methods of the invention may be applied to a subject who, at the time of treatment using a method and/or MAVS modulating compound of the invention, has been diagnosed with an autoimmune disease and is (1) undergoing treatment for one or more autoimmune diseases, (2) has undergone treatment for one or more autoimmune diseases, and/or (3) will be administered a treatment for one or more autoimmune diseases.

In some aspects of the invention, a subject is at risk of having or developing one or more autoimmune diseases. A subject at risk of developing an autoimmune disease has an increased probability of developing the autoimmune disease, compared to a control risk of developing the autoimmune disease. In some embodiments of the invention, a level of risk may be statistically significant compared to a control level of risk. A subject at risk may include, for instance, a subject having a genetic abnormality, the presence of which has been demonstrated to have a correlative relation to a higher likelihood of developing an autoimmune disease; a subject who has undergone a treatment for an autoimmune disease but who considered to be at risk for a second autoimmune disease; a subject undergoing an autoimmune disease treatment other than an autoimmune disease treatment of the invention; a subject having a family and/or personal medical history of one or more autoimmune diseases; a subject exposed to an agent believed to trigger an autoimmune disease, or has not been exposed to an agent believed to prevent or reduce a risk of an autoimmune disease; and/or a subject who has previously been treated for the autoimmune disease and is in apparent remission.

In certain aspects of the invention methods are provide that can be used to distinguish between a high-level I IFN signature disease versus a low-level I IFN signature disease in a subject, thereby aiding in selecting an appropriate treatment for the subject. In a non-limiting example, if, in a sample from a subject, a level or characteristic of an oligomerized MAVS polypeptide complex is determined that correspond to that of a high-level I IFN signature disease such as, Neuromyelitis optica or Sjögren's syndrome, a treatment strategy appropriate for the high-level I IFN signature disease can be selected and if in the sample, a level or characteristic of an oligomerized MAVS polypeptide complex corresponds to that of a low-level I IFN signature disease such as multiple sclerosis, an treatment appropriate for the low-level I IFN signature disease can be selected for the subject.

In some aspects of the invention, increasing a level of a modulating agent of the invention in a cell or subject, for example increasing a level of a polypeptide comprising the sequence of one of SEQ ID NOs: 3-20, or its encoding polynucleotide, or an antibody that inhibits oligomerization of a MAVS polypeptide; may treat an autoimmune disease in the cell or subject. Thus, some embodiments of the invention include methods of administering a modulating agent that inhibits MAVS oligomerization to a cell, tissue, or subject in an amount effective to decrease a level, size, molecular weight, or other physical characteristic of an oligomerized MAVS polypeptide complex in the cell, tissue, or subject as a treatment for the autoimmune disease.

A level, size, molecular weight, or other physical characteristic of an oligomerized MAVS polypeptide complex can be determined and compared to control values of the a level, size, molecular weight, or other physical characteristic of an oligomerized MAVS polypeptide complex, respectively, according to the invention. A control value may be a predetermined value, which can take a variety of forms. It can be a single cut-off value, such as a median or mean. It can be established based upon comparative groups, such as in groups of cells or individuals having normal levels, sizes, molecular weights, or other physical characteristics of an oligomerized MAVS polypeptide complex (which in certain instances may be zero or may be a higher number) and groups of cells or individuals having abnormal levels, sizes, molecular weights, or other physical characteristics of an oligomerized MAVS polypeptide complex. Another example of comparative groups may be groups of cells or subjects having one or more symptoms of or a diagnosis of an autoimmune disease and groups of cells or subjects without one or more symptoms of or a diagnosis of the autoimmune disease. Another comparative group may be a group of subjects with a history of an autoimmune disease and a group of subjects without such a history. The predetermined value, of course, will depend upon the particular population selected. For example, an apparently healthy population of cells may have a different "normal" range than a population of cells from a source that has an autoimmune disease. Accordingly, the predetermined value selected may take into account the category in which an individual or cell falls. Appropriate ranges and categories can be selected with no more than routine experimentation by those of ordinary skill in the art. As used herein, "abnormal" means significantly different as compared to a normal control. By abnormal a level, size, molecular weight, or other physical characteristic of an oligomerized MAVS polypeptide complex it is meant higher level, size, or molecular weight relative to a selected control, and may include an increase in the level, size, or molecular weight of at least 0.1%, 0.5%, 1%, 5%, 10%, 20%, 30%, 40%, 50%, 60%, 70%, 80%, 90%, 100%, 200%, 500%, or more in a subject or cell as compared to the level in a normal control. It will be understood that if a normal control level of an oligomerized MAVS polypeptide complex is zero, an abnormal level is anything greater than zero.

It will be understood that controls according to the invention may be, in addition to predetermined values, samples of materials tested in parallel with the experimental materials. Examples include samples from control populations or control samples generated through manufacture to be tested in parallel with the experimental samples; and also a control may be a sample from a subject prior to, during, or after an autoimmune disease treatment, including but not limited to a treatment of the invention.

In certain aspects of the invention, one or more modulating agents of the invention are administered to one or more cells and/or subjects in a manner to contact one or more cells with the modulating agent and to decrease a level, size, molecular weight, or other physical characteristic of an oligomerized MAVS polypeptide complex in the one or more cells. A decrease may be, in some aspects of the invention, from an abnormal a level, size, molecular weight, or other physical characteristic of an oligomerized MAVS polypeptide complex, to a lower level that is closer to or the same as the a level, size, molecular weight, or other physical characteristic of an oligomerized MAVS polypeptide complex in a normal cell and/or subject.

A modulating agent useful in methods of the invention may inhibit oligomerization of a MAVS polypeptide by a direct or an indirection interaction with the MAVS polypeptide. For example, though not intended to be limiting, a modulating agent may be an antibody that binds to and sterically inhibits oligomerization between MAVS polypeptides, or may be a small molecule, polypeptide, or other modulating agent that directly interacts with one or more amino acid residues in a MAVS polypeptide sequence and thereby inhibits oligomerization of the MAVS polypeptide. A non-limiting example of a modulating agent that inhibits MAVS polypeptide oligomerization is an agent that sterically blocks or directly contacts interferes with an action at amino acid corresponding to residue C79 and/or residue C33 in the MAVS polypeptide sequence set forth as SEQ ID NO: 1, which is the amino acid sequence of the GenBank® entry having Accession No.: AGF94754.1. Such an inhibitory agent may be used in certain embodiments of methods of the invention to inhibit formation of a disulfide bond in a polypeptide at one or more of (1) an amino acid that corresponds to residue C79 in the MAVS polypeptide sequence set forth as SEQ ID NO: 1 and (2) an amino acid that corresponds to residue C33 in the MAVS polypeptide sequence set forth as SEQ ID NO: 1. It will be understood that the term "corresponds to" when used in reference to an amino acid sequence means that the residues can be identified in for example, a variant of SEQ ID NO:1, a fragment of SEQ ID NO:1, a sequence that is longer than SEQ ID NO:1, using routine sequence alignment methods to align the sequence of interest with SEQ ID NO: 1 to identify the corresponding amino acid.

Non-limiting examples of modulating agent that may be used in embodiments of the invention to inhibit oligomerization of a MAVS polypeptide comprise a polypeptide comprising an amino acid sequence set forth as one of SEQ ID Nos: 3-20, or a functional variant thereof.

TABLE 1

Examples of inhibitory agents useful in methods to reduce MAVS oligomerization

| | |
|---|---|
| SEQ ID NO: 3 | CRIDVVDIIPYLSECL |
| SEQ ID NO: 4 | CLINQDQDCDEIRQI |
| SEQ ID NO: 5 | CRNFSNF |
| SEQ ID NO: 6 | ICRNFKAFSCDLAVRISILP |
| SEQ ID NO: 7 | RNFSNNVDVIIVQLNESVEI |
| SEQ ID NO: 8 | NVEVVDEILPY |

TABLE 1-continued

Examples of inhibitory agents useful in
methods to reduce MAVS oligomerization

SEQ ID NO: 9   VEILPYLPC

SEQ ID NO: 10  DVLIEVDILPFLPC

SEQ ID NO: 11  ARDQDRLRATCTLSGNRDT

SEQ ID NO: 12  CRIDVVDIIPYLSECL attached to a TAT
               sequence

SEQ ID NO: 13  CLINQDQDCDEIRQI attached to a TAT
               sequence

SEQ ID NO: 14  CRNFSNF attached to a TAT sequence

SEQ ID NO: 15  ICRNFKAFSCDLAVRISILP attached to a
               TAT sequence

SEQ ID NO: 16  RNFSNNVDVIIVQLNESVEI attached to a
               TAT sequence

SEQ ID NO: 17  NVEVVDEILPY attached to a TAT
               sequence

SEQ ID NO: 18  VEILPYLPC attached to a TAT
               sequence

SEQ ID NO: 19  DVLIEVDILPFLPC attached to a
               TAT sequence

SEQ ID NO: 20  ARDQDRLRATCTLSGNRDT attached to a
               TAT sequence

A functional variant of a polypeptide agent that inhibits MAVS oligomerization may have a sequence that is longer, shorter, or be the same length but have one or more amino acid substitutions. In certain aspects of the invention, a functional variant of a polypeptide inhibitory agent has 85%, 86%, 87%, 88%, 89%, 90%, 91%, 92%, 93%, 94%, 95%, 96%, 97%, 98%, 99%, or 100% sequence identity to at least one of SEQ ID NO: 3-20. In certain aspects of the invention an inhibitory agent may be a "null" activity MAVS polypeptide, for example, a MAVS polypeptide that comprises one or more sequence modifications, wherein at least one sequence modification inhibits MAV polypeptide oligomerization.

In addition to the inhibitory agent, an inhibitory compound that may be used in treatment methods of the invention may also include a one or more delivery agents, such as a delivery peptide, liposome, nanoparticle, targeting agent, etc. in conjunction with the inhibitory agent. Non-limiting examples of delivery agents that may be used in methods of the invention include cell-delivery agents, cell-penetrating peptides, a mitochondrial-targeting agent, a TAT sequence set forth here as SEQ ID NO: 21, HIV-1 Tat (48-60); TAT (47-57); MAP (KLAL); Penetratin-Arg; antitrypsin (358-374); TAT-HA2 Fusion Peptide; Temporin L; Maurocalcine; pVEC (Cadherin-5); Calcitonin; Neurturin; Human P1; Penetratin; and Pep-1-Cysteamine, etc. Delivery agents that can be used to deliver small molecules, polypeptides, and other therapeutic agents and methods of drug delivery using agents are well known in the art (see for example: Torchilin, V., 2008 Drug Discovery Today: Technologies Vol. 5 No. 2-3, pages e95-e103; Bruno, B J., et al. 2013 Therapeutic Delivery, Vol. 11: 1443-1467; and Ruan, R., et al. 2016 Therapeutic Delivery, Vol. 7: 89-100, the contents of which is incorporated by reference herein) and may be utilized in conjunction with inhibitory agents in some embodiments of treatment methods of the invention.

An inhibitory compound of the invention may include one or more detectable labels. Labeling agents may be used in certain embodiments of methods and compounds of the invention including, but not limited to: identifying a location of an inhibitory agent, identifying one or more characteristics of an oligomerized MAVS polypeptide complex in a cell and/or subject, preparing compounds for assays methods of the invention, performing assay methods of the invention; and assessing the cell, tissue, or organelle location of treatment compounds that have been administered. Procedures for attaching and utilizing labeling agents such as enzymatic labels, dyes, radiolabels, fluorescent labels, fluorophore molecules etc. are well known in the art. Non-limiting examples of fluorescent labels include: fluorescein, rhodamine, eosin, Texas Red, xanthene derivatives, Oregon Green, Alex Dyes, etc.

A MAVS molecule (polypeptide or encoding polynucleotide) that is administered to a subject in a treatment of the invention may be referred to herein as an exogenous MAVS molecule. A naturally expressed MAVS molecule that is present in a cell due to natural expression in that cell, and not due to administration of an exogenous MAVS molecule, is referred to herein as an "endogenous" MAVS molecule. A MAVS molecule, non-limiting examples of which are set forth herein as SEQ ID NOs: 1-11, or a molecule comprising a MAVS molecule non-limiting example of which are set forth herein as SEQ ID NOs: 12-20, may be administered to a subject either alone or as part of a compound of the invention, and in either case is considered to be an exogenous MAVS molecule. It will be understood that a MAVS molecule, a non-limiting example of which is the sequence set forth as SEQ ID NO: 1, that is present in a cell because of its natural expression in the cell may be referred to herein as an "endogenous" MAVS molecule. Thus, a molecule may be an exogenous MAVS molecule or an endogenous MAVS molecule, depending on whether the MAVS molecule was administered to a cell or subject, for example using a compound, composition, and/or method of the invention; or the MAVS molecule is expressed its presence in a cell or subject is not the result of a treatment or compound of the invention. A MAVS polypeptide that is useful as an inhibitory agent in methods of the invention may be: a natural MAVS polypeptide, derived from a human MAVS polypeptide, derived from a non-human MAVS polypeptide sequence (for example a mouse or other species), a recombinant MAVS polypeptide, an artificial sequence, a synthetic polypeptide, or other type of polypeptide.

Molecules, compounds, compositions, and methods of the invention may be used to treat a subject having, or at risk of having an autoimmune disease. Thus, methods and compounds of the invention are useful to treat autoimmune diseases in cells, tissues, and in subjects. Although not intended to be limiting, in certain aspects of the invention, contacting a cell and or subject with an exogenous MAVS molecule may decrease a level, size, molecular weight, or other physical characteristic of an oligomerized MAV polypeptide complex in the cell and/or subject. Treatment methods of the invention that inhibit oligomerization of a MAV polypeptide may reduce and/or eliminate a level, size, molecular weight, or other physical characteristic of an oligomerized MAV polypeptide complex. An abnormal level, size, molecular weight, or other physical characteristic of an oligomerized MAV polypeptide complex may be modified by a treatment of the invention and result in a more normal, or normal level, size, molecular weight, or other physical characteristic of an oligomerized MAV polypeptide complex in the treated cell and/or subject.

Methods for Detection and Treatments

An agent or compound that modulates oligomerization of a MAVS polypeptide, also referred to herein as a modulatory compound of the invention, may be administered to a cell, tissue, and/or subject to treat one or more different autoimmune diseases that are associated with abnormal oligomerized MAVS polypeptide complexes. By associated is meant that the presence of an abnormal level, size, molecular weight, or other physical characteristic of oligomerized MAVS polypeptide complexes is a feature of the autoimmune disease. Autoimmune diseases associated with abnormal oligomerized MAVS polypeptide complexes may be treated with inhibitory compounds and methods of the invention. Examples of autoimmune diseases that may be treated with inhibitory compounds and methods of the invention include, but are not limited to: Systemic Lupus Erythematosus (SLE), atherosclerosis, rheumatoid arthritis, Sjögren's syndrome, asthma that is positive for type I IFN signature, dilated cardiomyopathy, cardiomyopathy, systemic sclerosis, Aicardi-Goutieres syndrome, type I diabetes, autoimmune thyroid disease, and neuromyelitis optica.

In certain embodiments of the invention, contacting a cell or subject with an inhibitory agent of the invention decreases a level, molecular weight, size or other physical characteristic of an oligomerized MAVS polypeptide complex in the cell or subject, respectively. Examples of inhibitory agents that may be used in embodiments of methods of the invention are MAVS polypeptides or polynucleotides that encode MAVS polypeptides. Non-limiting examples of MAVS polypeptides that may be included in inhibitory compounds and used in treatments of the invention include: SEQ ID NOs: 2-20. One of ordinary skill in the art will understand how to prepare additional MAVS polypeptides that are fragments of a longer MAVS polypeptide and/or fragments of a full-length MAVS polypeptide for use in the methods of the invention. It will be understood that in some embodiments of the invention, a fragment of a full-length MAVS polypeptide may have an amino acid sequence that corresponds to the amino acid sequence set forth as SEQ ID NO:1, or a variant thereof, but without 1, 2, 3, 5, 6, up to 530, 531, 532, 533, 534, or 535 (including each integer from 1 to 535, inclusive) amino acids corresponding to the full-length MAVS polypeptide sequence set forth as SEQ ID NO: 1. Examples of fragments useful in methods of the invention include, but are not limited to polypeptides having a sequence set forth as one of: SEQ ID NOs: 3-11.

Additions of amino acids to SEQ ID NO: 1 or a functional fragment thereof can be readily envisioned by one of ordinary skill in the art. For example, though not intended to be limiting, 1, 2, 3, 4, 5, 6, 7, 8, 9, 10, 11, 12, or more amino acids may be added to the one or both ends of SEQ ID NO: 1 or a functional fragment thereof.

In certain aspects of the invention, an inhibitor agent may be an antibody or functional fragment thereof, a small molecule, a MAVS polypeptide or encoding polynucleotide and one or more targeting agent, also referred to herein as a delivery agent. A non-limiting example of a targeting agent is a cell penetrating peptide, a cell internalization agent, an HIV-derived TAT sequence, a small molecule, a polynucleotide, a liposome, a PEGylated liposome, an aquasome, a biodegradable polymer, a nanoparticle, an oligonucleotide, and a polypeptide. In certain embodiments of the invention a targeting agent assists in one or more of: directing an inhibitory agent or compound to a specific cell or tissues, internalization of an inhibitory agent or compound into a cell, etc. In certain aspects of the invention, a targeting agent is a cell internalization agent comprising a TAT polypeptide sequence, and optionally comprising a TAT polypeptide sequence set forth as GRKKRRQRRRPQ (SEQ ID NO: 21), or a variant thereof. Other cell internalization agents are known in the art and can also be including in compounds of the invention and utilized in methods of the invention using routine procedures.

In certain aspects of the invention, an inhibitory compound of the invention comprises an antibody, an siRNA molecule, a small molecule, a MAVS polypeptide, and one or more targeting polypeptides. A peptide in an inhibitory compound may in some embodiments of the invention, be a polypeptide described herein or a variant thereof. Similarly, in certain embodiments of the invention, a targeting agent may be targeting agent described herein, another art-known targeting polypeptide, or a variant thereof. In embodiments that include a polypeptide targeting agent the polypeptide may comprise an amino acid sequence such as one set forth herein, the amino acid sequence of another art-known targeting polypeptide, or a variant thereof. It will be understood that variants of targeting agents are also encompassed in some aspects of the invention. For example, an amino acid sequence of a peptide targeting agent may be modified from one described herein, or from another art-known targeting polypeptide sequence. A skilled artisan can prepare and utilize variant targeting agents using standard methods.

A variant polypeptide (also referred to herein as a "modified" polypeptide) may include deletions, point mutations, truncations, amino acid substitutions and/or additions of amino acids or non-amino acid moieties. Modifications of a polypeptide of the invention may be made by modification of the nucleic acid sequence that encodes the polypeptide or alternatively, modifications may be made directly to the polypeptide, such as by cleavage, addition of a linker molecule, addition of a detectable moiety, such as a fluorescent label, and the like. Modifications also embrace fusion proteins comprising all or part of the polypeptide's amino acid sequence.

As used herein, the terms "protein" and "polypeptide" are used interchangeably and thus the term polypeptide may be used to refer to a full-length protein and may also be used to refer to a fragment of a full-length protein. As used herein, the terms "polynucleotide" and "nucleic acid sequence" may be used interchangeably and may comprise genetic material including, but not limited to: RNA, DNA, mRNA, cDNA, etc., which may include full-length sequences and/or fragments thereof. As used herein the terms: "MAVS polypeptide" or "MAVS-encoding polynucleotide" of the invention will be understood to refer to MAVS sequences disclosed herein and variants of such sequences. As used herein with respect to polypeptides, proteins, or fragments thereof, and polynucleotides that encode such polypeptides the term "exogenous" means the compound is administered to a cell or subject and was not naturally present in the cell or subject. It will be understood that an exogenous MAVS polypeptide or MAVS polypeptide-encoding nucleic acid sequence may be identical to an endogenous MAVS polypeptide or MAVS polypeptide-encoding nucleic acid sequence, respectively, in terms of its sequence, but was administered to the cell or subject.

In certain embodiments of the invention, a polypeptide variant may be a polypeptide that is modified specifically to alter a feature of the polypeptide unrelated to its physiological activity. For example, cysteine residues can be substituted or deleted to prevent unwanted disulfide linkages. A residue may be added at the N or C-terminal end of the polypeptide. Polypeptides can be synthesized with modifications and/or modifications can be made in a polypeptide by selecting and introducing an amino acid substitution, deletion, or addition. Modified polypeptides then can be tested for one or more activities (e.g., inhibition of oligomerization of a MAVS polypeptide) to determine which modification provides a modified polypeptide with the desired properties.

The skilled artisan will also realize that conservative amino acid substitutions may be made in a polypeptide to provide functionally equivalent polypeptides, i.e., a modified inhibitory polypeptide, modified inhibitory antibody, or modified MAVS polypeptide etc. that retains a functional capability of an un-modified inhibitory polypeptide, modified inhibitory antibody, or modified MAVS polypeptide, respectively. As used herein, a "conservative amino acid substitution" refers to an amino acid substitution that does not alter the relative charge or size characteristics of the polypeptide in which the amino acid substitution is made. Conservative substitutions of amino acids may, in some embodiments of the invention, include substitutions made amongst amino acids within the following groups: (a) M, I, L, V; (b) F, Y, W; (c) K, R, H; (d) A, G; (e) S, T; (f) Q, N; and (g) E, D. Polypeptide variants can be prepared according to methods for altering polypeptide sequence and known to one of ordinary skill in the art such. Non-limiting examples of functionally equivalent polypeptide variants are inhibitory antibodies, or MAVS polypeptides with conservative amino acid substitutions of the antibody or MAVS polypeptide, respectively, and/or are fragments of an antibody or MAVS polypeptide, respectively. In certain embodiments of the invention, an inhibitory agent may be a polypeptide variant that comprises a fragment of the amino acid sequence of a MAVS polypeptide and the fragment has at least 75%, 80%, 85%, 90%, 91%, 92%, 93%, 94%, 95%, 96%, 97%, 98%, 99%, or 100% sequence identity to the region of the amino acid sequence of the MAVS polypeptide with which it aligns.

As used herein the term "modified" or "modification" in reference to a polynucleotide or polypeptide sequence refers to a change of one, two, three, four, five, six, or more nucleic acids or amino acids, respectively, in the sequence as compared to the corresponding unmodified sequence. For example, though not intended to be limiting, a modified polypeptide sequence may be identical to that of a first MAVS polypeptide sequence except that it has one, two, three, four, five, or more amino acid substitutions, deletions, insertions, or combinations thereof, and thus is a variant of the first MAVS polypeptide sequence.

The invention, in some aspects, includes polypeptides having one or more substitutions or other modifications from those described herein. For example, though not intended to be limiting, a sequence of a MAVS polypeptide can be modified with one or more substitutions, deletions, insertions, or other modifications and can be tested using methods described herein for characteristics including, but not limited to: expression; cell localization; efficacy in decreasing a level, size, molecular weight, or other physical characteristic of an oligomerized MAVS polypeptide complex; and efficacy in treating an autoimmune disease. MAVS molecules of the present invention include MAVS polypeptide and nucleic acid sequences provided herein and variants that have at least about 75%, 80%, 85%, 90%, 95%, 96%, 97%, 98%, or 99% identity to an amino acid or nucleic acid sequence, respectively, described herein. Inhibitory agents of the invention that include one or more MAVS polypeptides may, in some embodiments, include one or more MAVS polypeptide and targeting polypeptide sequences provided herein and variants that may have an amino acid sequence with at least 75%, 80%, 85%, 90%, 95%, 96%, 97%, 98%, or 99% identity to an amino acid sequence described herein. It will be understood that a polynucleotide that encodes a polypeptide inhibitory agent or compound that comprises a MAVS polypeptide may comprise a nucleic acid sequence that has least 75%, 80%, 85%, 90%, 95%, 96%, 97%, 98%, or 99% identity to a nucleic acid sequence encoding a MAVS polypeptide sequence including, but not limited to those described herein.

Sequence identity can be determined using standard techniques known in the art. To determine the percent identity (similarity) of two amino acid sequences the sequences are aligned for optimal comparison purposes (e.g., gaps may be introduced in the sequence of one protein for optimal alignment with the other protein). The amino acid residues at corresponding amino acid positions are then compared. When a position in one sequence is occupied by the same amino acid residue as the corresponding position in the other sequence, then the molecules have identity/similarity at that position. The percent identity or percent similarity between the two sequences is a function of the number of identical positions shared by the sequences (i.e., % identity or % similarity=number of identical positions/total number of positions×100). Such an alignment can be performed using any one of a number of well-known computer algorithms designed and used in the art for such a purpose. Similarly, percent identity/similarity of polynucleotide sequences encoding a polypeptide of the invention can be determined using art-known alignment and comparison methods for nucleic acids. MAVS polypeptides and/or targeting polypeptides of the invention may be shorter or longer than MAVS and/or targeting polypeptide sequences, respectively, set forth herein. In addition, polynucleotides that encode MAVS polypeptides can be used to identify and obtain additional polypeptide sequences, using techniques known in the art.

Modified sequences, (which are also referred to herein as variants) may in some embodiments be prepared by site specific mutagenesis of nucleic acids in the DNA encoding a polypeptide of the invention, using cassette or PCR mutagenesis or other techniques known in the art, to produce DNA encoding the polypeptide, and thereafter expressing the DNA in recombinant cell culture. Where amino acid substitutions are made to a small fragment of a polypeptide, the substitutions can be made by directly synthesizing the polypeptide. In certain embodiments of the invention, activity of variant or fragment of a polypeptide can be tested by cloning the gene encoding the altered polypeptide into a bacterial or mammalian expression vector, introducing the vector into an appropriate host cell, expressing the altered polypeptide, and testing for a functional capability of the polypeptide as disclosed herein.

Amino acid substitutions are typically of single residues and in certain embodiments of the invention, 1, 2, 3, 4, 5, 6, 7, 8, 9, 10, 11, 12, 13, 14, 15, 16, 17, 18, 19, 20 or more substitutions can be made in the amino acid sequence of an MAVS and/or targeting polypeptide of the invention, for example, though not intended to be limiting, in a sequence set forth here as SEQ ID NOs: 1-21. Amino acid insertions in the amino acid sequence of a MAVS and/or targeting polypeptide of the invention, for example, though not intended to be limiting, in a sequence set forth here as SEQ ID NOs: 1-21 may include insertion of 1, 2, 3, 4, 5, 6, 7, 8, 9, 10, 11, 12, 13, 14, 15, 16, 17, 18, 19, or 20 amino acids, although larger insertions may be tolerated. Amino acid deletions in the sequence of a MAVS and/or targeting polypeptide of the invention, for example, though not intended to be limiting, in a sequence set forth here as SEQ ID NOs: 1-21 may include deletions of 1, 2, 3, 4, 5, 6, 7, 8, 9, 10, 11, 12, 13, 14, or 15 amino acids, although larger deletions may be tolerated. Substitutions, deletions, insertions or any combination thereof may be used to arrive at a final modified MAVS and/or targeting polypeptide that may be components of certain inhibitory compounds of the invention. Generally these changes are done on a few amino acids to minimize the alteration of the molecule. However, larger changes may be tolerated in certain circumstances. A modified MAVS and/or targeting polypeptide of the invention may, in some embodiments, incorporate unnatural amino acids as well as natural amino acids. An unnatural amino acid can be included in an MAVS and/or targeting polypeptide of the invention to enhance a characteristic such as cell penetration, targeting, delivery, function, stability, or to lower toxicity, etc.

Inhibitory Treatment Methods

Inhibitory compounds of the invention that decrease one or more of a level, size, molecular weight, or other physical characteristic of an oligomerized MAVS polypeptide complex in a cell and/or subject may be administered in an effective amount to a subject in need of treatment of an autoimmune disease. Administering to a subject an inhibitory compound that decreases one or more of a level, size, molecular weight, or other physical characteristic of an oligomerized MAVS polypeptide complex in a cell and/or subject may reduce an autoimmune disease in a cell and/or subject. An inhibitory agent or compound useful to treat an autoimmune disease may, in some embodiments of the invention be a polynucleotide that encodes a MAVS polypeptide. Thus, a method of the invention may include administering a MAVS polypeptide or a MAVS polypeptide-encoding polynucleotide to a subject.

As used herein, the terms "treat", "treated", or "treating" when used with respect to an autoimmune disease may refer to a prophylactic treatment that decreases the likelihood of a subject developing the disease or condition, and also may refer to a treatment after the subject has developed the an autoimmune disease in order to eliminate or ameliorate the an autoimmune disease, prevent the an autoimmune disease from becoming more advanced and severe, and/or slow the progression of the an autoimmune disease compared to in the absence of the therapy.

A treatment method of the invention in some aspects includes compounds and methods for decreasing a level, size, molecular weight, or other physical characteristic of an oligomerized MAVS polypeptide complex in a cell, tissue, and/or subject. In certain aspects of the invention, decreasing the level a level, size, molecular weight, or other physical characteristic of an oligomerized MAVS polypeptide complex in a cell and/or subject may result from contacting the cell and/or administering to the subject an inhibitory compound of the invention. In some embodiments of the invention, a level, size, molecular weight, or other physical characteristic of an oligomerized MAVS polypeptide complex can be decreased by administration and/or contact with an inhibiting compound such as, but not limited to, a polypeptide set forth as SEQ ID NOs: 3-10, or a functional variant thereof, a binding agent, or a small molecule that inhibits oligomerization of a MAVS polypeptide. In certain embodiments of the invention, methods include decreasing a level, size, molecular weight, or other physical characteristic of an oligomerized MAVS polypeptide complex in a cell, tissue, or subject, by delivering an inhibitory compound of the invention into the cell, tissue or subject, to treat an autoimmune disease in the cell, tissue, or subject.

According to some aspects of the invention, one or more inhibitory agents such as an antibody, small molecule, or MAVS polypeptide or its encoding polynucleotide may be administered in methods of the invention. In some embodiments of the invention, one or more of a level, size, molecular weight, or other physical characteristic of an oligomerized MAVS polypeptide complex may be modulated by genetically introducing a MAVS polypeptide into a cell and/or subject, and reagents and methods are provided for genetically targeted expression of MAVS polypeptides. Genetic targeting can be used to deliver MAVS polypeptides to specific cell types, to specific cell subtypes, to specific spatial regions within an organism, and to sub-cellular regions within a cell. Genetic targeting also relates to the control of the amount of a MAVS polypeptide expressed, and the timing of the expression. Some embodiments of the invention include a reagent for genetically targeted expression of a MAVS polypeptide, wherein the reagent comprises a vector that contains a polynucleotide that encodes a MAVS polypeptide or encodes a functional fragment of a MAVS polypeptide.

As used herein, the term "vector" refers to a polynucleotide molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert MAVS polypeptides into dividing and non-dividing cells and can insert one or more MAVS polypeptides to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. In certain embodiments of the invention, a vector may be a lentivirus comprising a nucleic acid or gene that encodes a MAVS polypeptide of the invention or a variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a MAVS polypeptide in a wide variety of cell types—thus a promoter for a gene that is widely expressed in a variety of cell types, for example a "housekeeping gene" can be used to express a MAVS polypeptide in a variety of cell types. Non-limiting examples of general promoters are provided elsewhere herein and suitable alternative promoters are well known in the art. In certain embodiments of the invention, a promoter may be an inducible promoter, examples of which include, but are not limited to tetracycline-on or tetracycline-off, etc.

Additional inhibitory agents and compounds that may be administered in treatment methods of the invention include antibodies, small molecule that decrease one or more of a level, size, molecular weight, or other physical characteristic of an oligomerized MAVS polypeptide complex in a cell and/or subject. Methods of identifying and testing such antibodies and small molecules may include use of art-known procedures such as screening and testing procedures in conjunction with the teaching provided herein.

Inhibitory agents and compounds of the invention may be administered singly or in combination with one or more additional compounds. In some embodiments, an inhibitory agent or compound of the invention may act in a synergistic manner with one or more additional therapeutic agents or treatments and increase the effectiveness of the one or more therapeutic agents or activities. Thus, for example, administration of an inhibitory agent or compound of the invention to a cell and/or subject in conjunction with another treatment for an autoimmune disease may enhance the efficacy of the autoimmune disease treatment. Thus, an inhibitory agent or compound of the invention may increase the effectiveness of one or more other agents or treatments that are administered to treat an autoimmune disease.

It will be understood that additional inhibitory agents and compounds can be identified and used in methods of the invention. For example, assays and methods presented herein can be used to assess candidate compounds for their ability to decrease one or more of a level, size, molecular weight, or other physical characteristic of an oligomerized MAVS polypeptide complex in a cell and/or subject and assess their ability to treat an autoimmune disease when administered to a cell and/or subject. Inhibitory agents and compounds of the invention described herein can be used alone or in conjunction with other molecules such as targeting agents and labeling agents, in treatment methods of the invention.

Targeting agents useful in some aspects of the invention are targeting agents that direct or assist in directing an inhibitory compound of the invention to a specific cell type to be treated. A targeting agent of choice will depend upon the nature of the autoimmune disease and the location desirable to target for efficacious treatment of the disease. Those of ordinary skill in the art will be aware of and will be able to select and use suitable targeting agents in embodiments of the invention using routine methods. A non-limiting example of a targeting agent useful in certain embodiments of the invention is a cell-penetrating peptide, a cell internalization agent, an HIV-derived TAT sequence, a small molecule, a polynucleotide, a liposome, a PEGylated liposome, an aquasome, a biodegradable polymer, a nanoparticle, an oligonucleotide, and other targeting polypeptides. A non-limiting example of a cell targeting polypeptide that may be used to deliver an inhibitory agent or compound of the invention into a cell in certain embodiments of the invention is a TAT polypeptide comprising the sequence: GRKKRRQRRRPQ (SEQ ID NO: 21), or a variant thereof.

Compositions, compounds, and methods of the invention may be enhanced by utilization in combination with other procedures for treating an autoimmune disease. In some instances a treatment procedure may involve administration of another therapeutic agent or treatment such a medicament and/or surgery, physical therapy, diet modification, etc. Thus, in some embodiments of the invention, administration of an inhibitory agent or compound of the invention may be performed at one of more of: prior to, coincident with, or after administration of another therapy for treating the autoimmune disease. Treatment methods of the invention that include administration of an inhibitory agent or compound can be used at any stages of an autoimmune disease including in a pre-disease, active disease, relapse, etc. Methods of the invention may also be used for subjects who have previously been treated with one or more other autoimmune disease therapies that were not successful, were minimally successful, and/or are no longer successful at slowing or stopping progression of the autoimmune disease in the subject.

In certain aspects of the invention a treatment comprises administration of one or more anti-oxidant agents. Non-limiting examples of antioxidant agents are: Pan-antioxidant N-acetyl-L-cysteine (NAC), vitamin C and mitochondrion-permeable antioxidants: edaravone, idebenone, α-Lipoic acid, carotenoids, a non-limiting example of which is astaxanthin, vitamin E, coenzyme Q10, and mitochondria-targeted antioxidants MitoQ and SkQ. Mitochondrial antioxidants are known in the art, see for example: Zhong-Wei Zhang, et al. "Mitochondrion-Permeable Antioxidants to Treat ROS-Burst-Mediated Acute Diseases," in Oxidative Medicine and Cellular Longevity, vol. 2016, Article ID 6859523, 10 pages, 2016. doi:10.1155/2016/6859523, the content of which is incorporated herein by reference. Administration of one or more of such antioxidants may be used in treatment methods of the invention.

Other treatment methods of the invention comprise administering a therapeutic agent that targets a molecule that associates with oligomerized MAVS in disease. For example, though not intended to be limiting, certain aspects of the invention comprise a treatment method in which a polypeptide that binds CL is administered to a subject in an amount effective to treat an immune system disease or disorder. Such a polypeptide interferes with and reduces binding of oligomerized MAVS and CL. A non-limiting example of an agent that targets a molecule that associates with oligomerized MAVS in disease is a polypeptide that targets cardiolipin and inhibits its interaction/binding with oligomerized MAVS, for example an anti-cardiolipin antibody, or functional fragment thereof, a small molecule that binds CL, etc.

Another aspect of the invention includes treatment methods comprising administering an effective amount of a therapeutic agent such as Szeto-Schiller (SS) peptide antioxidant to a subject to treat a disease or disorder, such as, but not limited to: SLE. A non-limiting example of an SS peptide that may be used in embodiments of the invention is: mitochondria-targeted tetra peptide (MTP) SS-31, SS-01, SS-02, and SS-20.

In addition, the invention includes, in some aspects, combination therapeutic methods comprising administering an effective amount of two or more therapeutic agents to a subject. In a non-limiting example, an antioxidant agent such as MitoQ can be administered to a subject and another agent such as a Szeto-Schiller (SS) peptide antioxidant can also be administered. Non-limiting examples of SS peptides that may be used in embodiments of the invention are: mitochondria-targeted tetra peptide (MTP) also known as SS-31; SS-01; SS-02; and SS-20. In certain embodiments of methods of the invention, SS-31 and MitoQ are administered to a subject. In certain embodiments of methods of the invention, administering an effective amount of two or more agents results in a synergistic effect, in which the combination treatment results in greater therapeutic efficacy than the additive effects of the agents given singly.

Effective Amounts

Inhibitory agents and compounds of the invention are administered to a cell or subject in an effective amount for treating an autoimmune disease. An "effective amount for treating an autoimmune disease" is an amount necessary or sufficient to realize a desired biologic effect. For example, an effective amount of an inhibitory agent or compound of the invention could be that amount necessary to do one or more of (i) slowing or halting progression of the autoimmune disease and (ii) reversing one or more symptoms of the autoimmune disease. According to some aspects of the invention, an effective amount is that amount of an inhibitory agent or compound of the invention alone or in combination with another medicament or treatment, which when combined or co-administered or administered alone, results in a desired therapeutic response in the subject, either in the prevention or the treatment of the autoimmune disease. In some aspects of the invention, a desired biological effect may be one or more of: a decrease one or more of a level, size, molecular weight, or other physical characteristic of an oligomerized MAVS polypeptide complex; the amelioration and or absolute elimination of symptoms resulting from the autoimmune disease; the complete abrogation of the autoimmune disease, as evidenced for example, by a diagnostic test that indicates the subject is free of the autoimmune disease, or that one or more of the presence, level, and severity of the autoimmune disease is reduced.

Typically an effective amount of an inhibitory agent or compound will be determined in clinical trials, establishing an effective dose for a test population versus a control population in a blind study. In some embodiments, an effective amount will be that results in a desired response, e.g., an amount that diminishes an autoimmune disease; decrease one or more of a level, size, molecular weight, or other physical characteristic of an oligomerized MAVS polypeptide complex in a cell and/or subject; maintains an autoimmune disease in remission in cells and/or a subject with the autoimmune disease. Thus, an effective amount to treat an autoimmune disease may be the amount that when administered decreases one or more of a level, size, molecular weight, or other physical characteristic of an oligomerized MAVS polypeptide complex in a cell to an amount that is below the amount that would occur in the subject or tissue without the administration of the inhibitory agent or compound. In the case of treating an autoimmune disease a desired response to a treatment of the invention may be reducing or eliminating one or more symptoms or physiological characteristics of the autoimmune disease in cell, tissue, and/or subject. The reduction or elimination may be temporary or may be permanent. The status of the autoimmune disease can be monitored using art-known methods. In some aspects of the invention, a desired response to treatment of an autoimmune disease may comprise delaying or preventing onset of the autoimmune disease, slowing, delaying, or stopping the autoimmune disease's progression, maintaining remission of an autoimmune disease, etc.

An effective amount of an inhibitory agent or compound of the invention may also be determined by assessing physiological effects of administration of the inhibitory agent or compound on a cell or subject. As herein the term "administrating" when used in reference to treating one or more cells means contacting the one or more cells with the inhibitory agent or compound of the invention. Similarly, in some embodiments of treatment methods of the invention, administrating an inhibitory agent or compound to a subject comprises contacting one or more cells of the subject with the administered inhibitory agent or compound. In certain embodiments of the invention, an inhibitory agent or compound is part of a pharmaceutical composition. An inhibitory agent or compound of the invention may be administered as part of a pharmaceutical composition, wherein the manner of administration is suitable to contact one or more cells with the inhibitory agent or compound. A pharmaceutical composition of the invention that includes an inhibitory agent or compound may also include a pharmaceutically acceptable carrier.

Assays suitable to determine efficacy of an inhibitory agent or compound of the invention will be known to those skilled in the art and can be employed for measuring the level of the response to a treatment and an amount of an inhibitory agent or compound administered to a subject can be modified based, at least in part, on such measurements. Non-limiting examples of measurements of response to an autoimmune disease treatment of the invention include autoimmune disease diagnostic testing, symptom assessment, etc. The amount of a treatment may be varied for example by one or more of: increasing or decreasing the amount of a pharmaceutical composition administered, changing the pharmaceutical composition administered, changing the route of administration, changing the dosage timing, changing administration of another therapeutic agent or therapy, and so on. The effective amount will vary with the particular autoimmune disease being treated, the age and physical condition of the subject being treated; the stage and severity of the autoimmune disease, the duration of the treatment, the nature of a prior, concurrent, or impending therapy (if any), the specific route of administration, and additional factors within the knowledge and expertise of the health practitioner. For example, an effective amount may depend upon the degree to which an individual has oligomerized MAVS polypeptide complexes present in one or more cells; the level, size, molecular weight, or other physical characteristic of oligomerized MAVS polypeptide complexes that are present in the subject, or other factors.

An effective amount of one or more of an inhibitory agents or compound, an antibody, a small molecule, a MAVS polypeptide or its encoding polynucleotide for treatment of an autoimmune disease may vary depending upon the specific compound or molecule, the mode of delivery of the compound or molecule, and whether it is used alone or in combination with another therapy, therapeutic agent or compound. The effective amount for any particular application can also vary depending on such factors as the autoimmune disease being treated, the particular compound being administered, the size of the subject, or the severity of the autoimmune disease. A skilled artisan can empirically determine the effective amount of a particular compound of the invention without necessitating undue experimentation. Combined with the teachings provided herein, by choosing among the various active inhibitory agents or compounds of the invention and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat an autoimmune disease in a particular subject.

A pharmaceutical composition dosage and/or dosage of an inhibitory agent may be adjusted by an individual health care provider or veterinarian, particularly in the event of any complication. A therapeutically effective amount typically varies from 0.01 mg/kg to about 1000 mg/kg, from about 0.1 mg/kg to about 200 mg/kg, or from about 0.2 mg/kg to about 20 mg/kg, in one or more dose administrations daily, for one or more days. The absolute amount will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Multiple doses of compounds of the invention are also contemplated. In some instances, an inhibitory agent or compound of the invention can be administered at least daily, every other day, weekly, every other week, monthly, etc. Doses may be administered once per day or more than once per day, for example, 2, 3, 4, 5, or more times in one 24 hour period.

Pharmaceutical compositions of the invention may be administered alone, in combination with each other, and/or in combination with other drug therapies, or other treatment regimens that are administered to subjects with an autoimmune disease. Pharmaceutical compositions used in the embodiments of the invention preferably are sterile and contain an effective amount of an inhibitory agent to do one or more of (1) decrease one or more of a level, size, molecular weight, or other physical characteristic of an oligomerized MAVS polypeptide complex in a contacted cell and (2) produce a desired therapeutic response in a unit of weight or volume suitable for administration to a subject.

The doses of a pharmaceutical composition and/or an inhibitory agent or compound to treat an autoimmune disease that are administered to a subject can be chosen in accordance with different parameters, in particular in accordance with the mode of administration used and the state of the subject. Other factors may include the desired period of treatment. In the event that a response in a subject is insufficient at the initial doses applied, higher doses (or effectively higher doses by a different, more localized delivery route) may be employed to the extent that patient tolerance permits.

If two or more therapeutic agents are administered in a treatment method of the invention, they can be administered in succession, simultaneously, or with any timing protocol that results in an effective treatment. For example, a treatment may begin with administration of an antioxidant such as MitoQ, followed by administration of SS-031, or the reverse order. In some embodiments of the invention two or more therapeutic agents are administered in a single treatment session, which may be simultaneous administration, or administration within in a period of minutes or hours. Routine dosing practices and methods can be used to determine appropriate administration timing for single agents and combination treatments of the invention.

Administration Routes

A variety of administration routes for an inhibitory agent or compound of the invention are available. The particular delivery mode selected will depend upon the particular condition being treated and the dosage required for therapeutic efficacy. Methods of this invention, generally speaking, may be practiced using any mode of administration that is medically acceptable, meaning any mode that produces effective levels of treatment without causing clinically unacceptable adverse effects. In some embodiments of the invention, an inhibitory agent or compound of the invention may be administered via an oral, enteral, mucosal, percutaneous, and/or parenteral route. The term "parenteral" includes subcutaneous, intravenous, intramuscular, intraperitoneal, and intrasternal injection, or infusion techniques. Other routes include but are not limited to nasal (e.g., via a gastro-nasal tube), dermal, vaginal, rectal, and sublingual. Delivery routes of the invention may include intrathecal, intraventricular, or intracranial. In some embodiments of the invention, an inhibitory agent or compound of the invention may be placed within a slow release matrix and administered by placement of the matrix in the subject. In some aspects of the invention, an inhibitory agent or compound may be administered to a cell and/or subject using nanoparticles coated with a delivery agent that targets a specific cell or organelle.

An inhibitory agent or compound of the invention may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. According to methods of the invention, the compound may be administered in a pharmaceutical composition. In general, a pharmaceutical composition comprises the compound of the invention and a pharmaceutically-acceptable carrier. Pharmaceutically acceptable carriers are well known to the skilled artisan and may be selected and utilized using routine methods. As used herein, a pharmaceutically-acceptable carrier means a nontoxic material that does not interfere with the effectiveness of the biological activity of the active ingredients, e.g., the ability of the inhibitory agent to decrease one or more of a level, size, molecular weight, or other physical characteristic of an oligomerized MAVS polypeptide complex in a cell and/or subject.

Pharmaceutically acceptable carriers may include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

In some embodiments of the invention, an inhibitory agent or compound maybe administered directly to a tissue. In some embodiments, the tissue to which the compound is administered is a tissue in which a feature of an autoimmune disease including, but not limited to, abnormal oligomerization of MAVS polypeptides may be present or are likely to be present or to arise. Direct tissue administration may be achieved by direct injection, or other art-known means. An inhibitory agent or compound may be administered once, or alternatively may be administered in a plurality of administrations. If administered multiple times, an inhibitory agent or compound may be administered via different routes. For example, the first (or the first few) administrations may be made directly into the affected tissue while later administrations may be systemic.

An inhibitory agent or compound of the invention, when it is desirable to have it administered systemically, may be formulated for parenteral administration by injection, e.g., by bolus injection or continuous infusion. Formulations for injection may be presented in unit dosage form, e.g., in ampoules or in multi-dose containers, with or without an added preservative. The pharmaceutical compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of one or more inhibitory agents or compounds of the invention.

In yet other embodiments, a delivery vehicle is a biocompatible microparticle or implant that is suitable for implantation into the mammalian recipient. Exemplary bioerodible implants that are useful in accordance with this method are known in the art and may include a biocompatible, biodegradable polymeric matrix for containing a biological macromolecule. Such delivery means are well known in the art and can be used to achieve sustained release of a compound of the invention in a subject, and may be selected not to degrade, but rather, to release by diffusion over an extended period of time.

Both non-biodegradable and biodegradable polymeric matrices can be used to deliver one or more inhibitory agents or compounds of the invention to a cell and/or subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In certain embodiments of the invention, an inhibitory agent or compound of the invention may be delivered using the bioerodible implant by way of diffusion, or by degradation of the polymeric matrix. Exemplary synthetic polymers for such use are well known in the art. Biodegradable polymers and non-biodegradable polymers can be used for delivery of one or more inhibitory agents or compounds of the invention using art-known methods. Bioadhesive polymers such as bioerodible hydrogels (see H. S. Sawhney, C. P. Pathak and J. A. Hubell in Macromolecules, 1993, 26, 581-587, the teachings of which are incorporated herein) may also be used to deliver one or more inhibitory agents or compounds of the invention for treatment. Additional suitable delivery systems can include time-release, delayed release or sustained-release delivery systems. Such systems can avoid repeated administrations of an inhibitory agent or compound, increasing convenience to the subject and the physician. Many types of release delivery systems are available and known to those of ordinary skill in the art. (See for example: U.S. Pat. Nos. 5,075,109; 4,452,775; 4,675,189; 5,736,152; 3,854,480; 5,133,974; and 5,407,686 (the teaching of each of which is incorporated herein by reference). In addition, pump-based hardware delivery systems can be used, some of which are adapted for implantation.

Use of a long-term sustained release implant may be particularly suitable for prophylactic treatment of subjects and for subjects at risk of developing a recurrent symptoms or exacerbations of an autoimmune disease. Long-term release, as used herein, means that the implant is constructed and arranged to delivery therapeutic levels of the active ingredient for at least 30 days, 60 days, 90 days or longer. Long-term sustained release implants are well-known to those of ordinary skill in the art and include some of the release systems described above.

Therapeutic formulations of one or more inhibitory agents or compounds of the invention may be prepared for storage by mixing the inhibitory agent or compound having the desired degree of purity with optional pharmaceutically acceptable carriers, excipients or stabilizers [Remington's Pharmaceutical Sciences $22^{nd}$ edition, (2012)], in the form of lyophilized formulations or aqueous solutions. Acceptable carriers, excipients, or stabilizers are nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Efficacy Determination and Assays

Certain aspects of the invention include methods to assess the efficacy of an inhibitory agent or compound of the invention for treatment of an autoimmune disease. Such methods may include comparing the effect on an autoimmune disease model cell or test cell contacted with an inhibitory agent or compound to the status of a substantially similar autoimmune disease control cell that is not contacted with the inhibitory agent or compound. A change in one or more of desirable effects such as, but not limited to: a decrease in one or more of a level, size, molecular weight, and other physical characteristic of an oligomerized MAVS polypeptide complex, in the contacted test cell compared to the control cell indicates effectiveness of the inhibitory agent or compound for treatment of an autoimmune disease. In some embodiments of the invention, assay methods may include obtaining a sample from a subject, contacting at least a portion of the sample with an inhibitory agent or compound of the invention and assessing the response of one or more cells in the portion of the sample. The test cell's response may be compared to a control autoimmune disease cell. As used herein a sample may be an in vitro sample, or may a sample that is detected (e.g., obtained) in vivo. As used herein, a sample may be a cell sample, tissue sample, blood sample, serum sample, bodily fluid sample, subcellular sample, etc. A sample may include cells, tissues, or organelles.

Assays to assess the status of an autoimmune disease include but are not limited to (1) characterizing the efficacy of an inhibitory agent or compound in treating an autoimmune disease in a subject; (2) evaluating a combination treatment comprising administering one or more inhibitory agents or compounds of the invention and administering one or more additional therapeutic actions such as administering a therapeutic agent, a physical therapy, a dietetic therapy, or other therapeutic treatment, (3) selecting a treatment for an autoimmune disease based at least in part on the determined efficacy of the inhibitory agent or compound alone or in combination; and (4) administering an inhibitory agent or compound of the invention as at least a portion of a treatment of an autoimmune disease in a subject. Thus, subjects can be characterized, treatment regimens can be monitored, treatments can be selected and diseases status can be better understood using embodiments of methods of the present invention.

The invention, in some aspects, includes various assays to determine the efficacy of an inhibitory agent or compound administered to an autoimmune disease in a cell and/or subject. Methods of the invention that are useful to determine inhibitory agent or compound efficacy in cells, tissues, subjects, and samples (e.g., from subjects, in culture, etc.), include, but are not limited to: diagnostic assays to determine status of an autoimmune disease, a level, size, molecular weight and/or other characteristic of an oligomerized MAVS polypeptide complex in a cell and/or subject cells, etc. Assessments of efficacy of an inhibitory agent or compound of the invention to treat an autoimmune disease can be done in vitro, for example in cell culture, cell samples, cell suspensions, etc. or can be done in vivo, for example in a living subject using art-known autoimmune disease diagnostic assessments and tracking methods. Assessment of efficacy of candidate inhibitory agents and compounds to treat an autoimmune disease may also be done using assays of the invention in cells from culture—e.g., as screening assays to assess the ability of candidate inhibitory agents and compounds to do decrease one or more of a level, size, molecular weight, or other physical characteristic of activity characteristic of an oligomerized MAVS polypeptide complex in a cell, tissue, or subject and therefore may be used in a treatment method of the invention. As will be appreciated by those of ordinary skill in the art, the evaluation of a treatment also may be based upon an evaluation of the symptoms or clinical end-points of an autoimmune disease and such evaluations can be used in conjunction with methods of the invention to assess the status of an autoimmune disease and/or the efficacy of a treatment of the invention for an autoimmune disease.

Assessing Compounds for Treatment

Assessment of efficacy of compounds and agents to treat an autoimmune disease in a subject that have an abnormal oligomerized MAVS polypeptide complex size, level, molecular weight, or other physical characteristic, may also be done according to some embodiments of the invention, such as, in a non-limiting example, screening assays to assess candidate therapeutic agents or compounds to reduce or eliminate an oligomerized MAVS polypeptide complex (or undesirable characteristic thereof) from a subject. It will be understood that a therapeutic regimen may be either prophylactic or a treatment of an existing autoimmune disease in a subject. The invention in some aspects provides methods that may be used to monitor a subject's response to prophylactic treatment provided to a subject. Some embodiments of the invention may include methods to assess treatments intended to reduce, prevent, or eliminate an autoimmune disease and/or to provide an indicator of a status of an autoimmune disease. Methods of the invention can in certain aspects be used to select one or more therapies for the subject, for example, to select a drug therapy, a physical therapy, a surgical therapy, a dietetic therapy, etc. In some aspects, methods of the invention may include one or more of selecting a treatment for a subject and treating a subject for an autoimmune disease associated with an oligomerized MAVS polypeptide complex based at least in part on the results of an assay or assessment of the invention.

As used herein a "subject" refers to a mammal, including but not limited to a human, a non-human primate, a rodent, a dog, a cat, a horse, a cow, or other mammal. Thus, in addition to human medical application, some aspects of the invention include veterinary application of methods described herein. A subject may be suspected of having an autoimmune disease and/or be suspected of having an abnormal level, size, molecular weight, or other physical characteristic of an oligomerized MAVS polypeptide complex and methods of the invention can be used to determine, assess, and/or measure a level, size, molecular weight or other physical characteristic of an oligomerized MAVS polypeptide complex in a sample obtained from the subject, thus the subject may be diagnosed with the autoimmune disease. In some embodiments of the invention, a subject may not have been previously or be currently diagnosed with an autoimmune disease associated with an oligomerized MAVS polypeptide complex, but may be considered at risk of having the autoimmune disease, for example, a subject who may be free of symptoms, but who may have a family history, genetic background indicative of potential for an autoimmune disease associated with an abnormal level, size, molecular weight or other physical characteristic of an oligomerized MAVS polypeptide complex.

An autoimmune disease that may be detected, assessed, and/or treated with embodiments of methods of the invention may be autoimmune disease that are associated with an abnormal a level, size, molecular weight or other physical characteristic of an oligomerized MAVS polypeptide complex. Non-limiting examples of autoimmune diseases that may be detected, assessed, and/or treated using methods and compounds of the invention are Systemic Lupus Erythematosus (SLE), atherosclerosis, rheumatoid arthritis, and Sjögren's syndrome, asthma that is positive for type I IFN signature, dilated cardiomyopathy, cardiomyopathy, systemic sclerosis, Aicardi-Goutieres syndrome, type I diabetes, autoimmune thyroid disease, and neuromyelitis optica.

As used herein a "sample" may be a biological sample that may be obtained from a cell culture, cell suspension, cell, tissue, and/or subject. A sample obtained from a subject may comprise a blood sample, a tissue sample, a serum sample, a lymph sample, a mucus sample, or a stool sample. In certain embodiments of the invention, the sample is a serum sample. As used herein a serum sample comprises part of the blood that does not contain red or white blood cells.

The term "labeled or labelable", with regard to a MAVS-binding agent is intended to encompass direct labeling of the agent by coupling (i.e., physically linking) a detectable molecule to the agent, as well as indirect labeling of the agent by reactivity with another reagent that is directly labeled. Some non-limiting examples of indirect labeling include detection of a primary antibody using a fluorescently labeled secondary antibody and other means that will be known to the skilled artisan.

Certain methods of the invention include determining a level, size, molecular weight, or other physical characteristic of an oligoimerized MAVS polypeptide complex in order to aid in selecting an autoimmune disease treatment for a subject. In some aspects methods of the invention may include identifying a subject believed to be at risk for an autoimmune disease and then testing a sample that has been obtained from the subject. In some aspects the invention includes obtaining a sample from the subject for testing. In certain aspects of the invention the sample is a serum sample. For assessment of an oligomerized MAVS polypeptide complex in the sample, the sample is contacted with a MAVS-binding agent under suitable conditions for the MAVS-binding agent binds to the oligomerized MAVS polypeptide thereby forming what is referred to herein as a "bound complex", which comprises the MAVS-binding agent and the oligomerized MAVS polypeptide complex. After contacting the binding agent and a sample that might contain an oligomerized MAVS polypeptide complex, an assessment of a level, size, molecular weight, or other physical characteristic of an oligoimerized MAVS polypeptide complex can be determined, in part, by determining a characteristic of the bound complex. Characteristics of the bound complex that can be determined using methods of the invention include one or more physical properties of an oligomerized MAVS polypeptide complex that is part of the bound complex. Physical properties of the oligomerized MAVS polypeptide complex may be its level, size, molecular weight, or other physical characteristic of the oligomerized MAVS polypeptide complex. As described elsewhere herein, a physical characteristic may be the presence of another molecule, for example a phospholipid that is a component of the oligomerized MAVS polypeptide complex. A non-limiting example of a phospholipid that may be part of an oligomerized MAVS polypeptide complex is CL. In some aspects of the invention, determining the presence or absence and/or level of an oligomerized MAVS polypeptide complex in a sample comprises detecting the presence or absence and/or level of CL in the sample.

Methods of the invention, in some aspects may be used to assess one or more characteristics or physical property of a bound complex and/or an oligomerized MAVS polypeptide complex that makes up part of the bound complex. Art-known of detecting and assessing characteristic polypeptide complexes such as a bound complex of the invention, and non-limiting examples of methods that may be used are set forth elsewhere herein.

A MAVS-binding agent is an agent that selectively binds (also referred to as specifically binds) an oligomerized MAVS polypeptide complex. A non-limiting example of a MAVS-binding agent that may be used in methods of the invention is an antibody or functional fragment thereof that specifically binds the oligomerized MAVS polypeptide complex. Non-limiting examples of MAVS-binding agents are: an antibody or functional fragment thereof or a small molecule, etc. that specifically binds a MAVS oligomer, an antibody or functional fragment thereof or small molecule, etc. that specifically binds a CL phospholipid, etc. As used herein a "functional fragment" of an antibody is a portion of the antibody that retains a function of specific binding of the antibody to the oligomerized MAVS polypeptide complex. Those skilled in the art will understand how to prepare and use functional fragments of antibodies in methods of the invention.

An oligomerized MAVS polypeptide complex that is associated with an autoimmune disease includes aggregates of the N-terminal caspase activation and recruitment domain (CARD) of a MAVS polypeptide. In certain aspects a binding agent specifically binds an oligomerized MAVS polypeptide complex is a MAVS-binding agent that specifically binds an N-terminal caspase activation and recruitment domain (CARD) of a MAVS polypeptide.

In certain aspects of the invention, detecting specific binding of the MAVS-binding agent to the oligomerized MAVS polypeptide complex aids in selecting a treatment for a subject from whom the sample was obtained. In certain aspects of the invention, detecting specific binding of the MAVS-binding agent to the N-terminal caspase activation and recruitment domain (CARD) of a MAVS polypeptide aids in selecting administration of an anti-oxidative agent as a treatment for the subject. Examples, though not intended to be limiting, of anti-oxidative agents that may be used in methods of the invention are: Pan-antioxidant N-acetyl-L-cysteine (NAC), vitamin C and mitochondrion-permeable antioxidants: edaravone, idebenone, α-Lipoic acid, carotenoids, a non-limiting example of which is astaxanthin, vitamin E, coenzyme Q10, and mitochondria-targeted antioxidants MitoQ and SkQ. Mitochondrial antioxidants are known in the art, see for example: Zhong-Wei Zhang, et al. "Mitochondrion-Permeable Antioxidants to Treat ROS-Burst-Mediated Acute Diseases," in Oxidative Medicine and Cellular Longevity, vol. 2016, Article ID 6859523, 10 pages, 2016. doi:10.1155/2016/6859523, the content of which is incorporated herein by reference. Additional agents that may be used in methods of the invention include, but are not limited to: Szeto-Schiller (SS) peptide antioxidant agents, non-limiting examples of which are: mitochondria-targeted tetra peptide (MTP) also known as SS-31; SS-01; SS-02; and SS-20.

Methods of Preparing a Bound Complex

Methods of the invention, in some aspects, include making a bound complex that includes a MAVS-binding agent and an oligomerized MAVS polypeptide complex. Preparing a bound complex of the invention may include contacting a MAVS-binding agent with a sample that is believed to contain an oligomerized MAVS polypeptide complex. The contacting is done under conditions suitable to permit binding of the MAV-binding agent to an oligomerized MAVS polypeptide complex that is present in the sample. Non-limiting examples of suitable binding conditions are provided herein and others can be readily determined by the skilled artisan.

A bound complex prepared using methods of the invention can be assessed according to methods of the invention to determine one or more characteristic of the bound complex; one or more physical properties of an oligomerized MAVS polypeptide complex that is part of the bound complex, wherein non-limiting examples of the physical properties of the oligomerized MAVS polypeptide complex include: its level, size, molecular weight, or other physical characteristic Kits The invention also encompasses kits for detecting characteristics and properties of bound complexes and oligomerized MAVS polypeptide complexes in a sample. For example, a kit can comprise a labeled or labelable MAVS-binding agent capable of aiding in detecting and assessing an oligomerized MAVS polypeptide complex in a sample and a means for determining a status (e.g., at least one of the presence/absence, level, size, molecular weight, or other physical characteristic) of an oligomerized MAVS polypeptide complex in the sample. The MAVs-binding agent can be packaged in a suitable container. The kit can further comprise a means for comparing the presence/absence, level, size, molecular weight, or other physical characteristic) of an oligomerized MAVS polypeptide complex in the sample with a standard or control and/or can further comprise instructions for using the kit to detect the presence/absence, level, size, molecular weight, or other physical characteristic of the oligomerized MAVS polypeptide complex. A kit may also include a detectably labeled MAVS-binding agent. Thus, some embodiments of the invention provide kits that can be used to detect and assess the presence/absence, level, size, molecular weight, or other physical characteristic of an oligomerized MAVS polypeptide complex, and may be used to identify an autoimmune disease in a cell and/or subject. Kits of the invention may, in some embodiments, include one or more MAVS-binding agent (e.g., an antibody or antibody fragment, or other MAVS-binding agent, etc.) that selectively binds an oligomerized MAVS polypeptide complex and one or more detectable labels. Kits of the invention may also include buffers, containers, and other items for use in carrying out methods of the invention.

Also within the scope of the invention are kits that comprise compounds and pharmaceutical compositions (e.g., therapeutic compounds) of the invention and instructions for use. Kits of the invention may include one or more of an inhibitory agent of the invention or variant thereof that may be used to treat an autoimmune disease. Kits containing one or more agents that inhibit oligomerization of a MAVS polypeptide can be prepared for treatment methods of the invention. Components of kits of the invention may be packaged either in aqueous medium or in lyophilized form. A kit of the invention may comprise a carrier or delivery agent being compartmentalized to receive in close confinement therein one or more container means or series of container means such as test tubes, vials, flasks, bottles, syringes, or the like. A first container means or series of container means may contain one or more components such as one or more inhibitory agents or compounds, one or more MAVS polypeptides, one or more MAVS polypeptide-encoding polynucleotides, one or more targeting agents, one or more detectable labels, etc.

A kit of the invention may also include instructions. Instructions typically will be in written form and will provide guidance for carrying out the preparation of an inhibitory agent or compound of the invention, and/or use of an inhibitory agent or compound of the invention in an autoimmune disease treatment or assay.

Detection Assays and Methods:

The invention in some aspects includes methods of homo-FRET detection. Homo-FRET assay methods of the invention can be used to identify one or more characteristics of a molecule of interest in assay formats including but not limited to: plate-based assays and high-throughput plate-based assays. An embodiment of a homo-FRET assay method of the invention may be utilized in other art-known assay formats, configurations, and procedures. Certain embodiments of homo-FRET assay methods of the invention can be used to identify one or more characteristics of a polypeptide or peptide complex in a test sample.

In some embodiments of the invention, a homo-FRET assay method includes a multi-step procedure with which to assess characteristic of a molecule of interest. In certain aspects of the invention, the method includes (a) determining a level of a detectable label in an assay sample that includes a first binding compound. What is referred to herein as the "first" binding compound may include at least one of each of a binding agent that specifically binds a molecule of interest, a bead, and a detectable label. In certain aspects of the invention, the binding agent is attached to the bead and to the detectable label. Means and procedures for attaching binding agents, beads, and/or detectable labels to each other, are well known in the assay arts and can be performed using procedures described herein and using standard procedures practiced in the art.

After the level of the detectable label in the assay sample is determined, the assay sample is contacted with a test sample. As used herein, the term "test sample" used in relation to a homo-FRET assay of the invention means a sample that is known to include, or to possibly include, the molecule of interest. The test sample is added to the assay sample under conditions suitable for the first binding compound and the molecule of interest to form a bound complex. A level of the detectable label in the mixture of the test sample and the assay sample is determined and the mixture of the test sample and the assay sample (also referred to as the "contacted assay sample") are contacted with a second binding compound. A second binding compound of the invention comprises a binding agent that specifically binds the molecule of interest and the same type of detectable label (e.g. same fluorophore) as is attached to the first binding compound, but the second binding compound is not attached to the surface to which the first binding compound is attached. The second binding agent, which may be the same as the first binding agent, may be a different binding agent, or may be a functional variant of first binding agent, is attached to the same type of detectable label that is part of the first binding compound. The level of the detectable label in the contacted mixed assay sample and test sample is detected. One of more characteristics of the molecule of interest can be determined by comparing two or more levels of the detectable label that were determined in the initial assay sample, the mixed assay/test sample, and the contacted mixed assay/test sample.

In certain aspects of the invention the first binding compound in the assay sample is attached to a surfaced the second binding compound is not attached to the surface prior to its addition to the mixture that includes the assay sample and the test sample. Non-limiting examples of types of surfaces include: a glass surface, a plastic surface, a microscope slides, a culture dish, an assay plate, an ELISA plate, an assay dish etc. Methods of attaching beads, assay components etc. for use in assay methods are routinely practiced in the art. Non-limiting examples of beads that may be used in aspects of the invention include a metal bead, a magnetic bead, a bead comprising gold, a bead comprising silver, and a bead comprising a metal other than gold or silver. A non-limiting example of method for attachment that may be used in homo-FRET assay methods of the invention is as follows: solutions containing 1% $HAuCl_4$ or 0.83% of $AgNO_3$ may be used in the presence of reducing agents to achieve chemical plating of plate surfaces. Alternative means of attachment can be utilized in assay methods of the invention, for example, a homogeneous layer of colloidal gold or silver nanoparticles in individual wells of ELISA plates can be prepare and other suitable means for attaching the first binding compound to a surface are described in the art, for example: Bai et al., (2009) Langmuir, 25(17), pp 10402-10407; Li J, et al., (2010) Anal Bioanal Chem. November; 398(5):1993-2001; and Aslan K, et al., (2005)

Curr Opin Biotechnol. February; 16(1):55-62, each of which is incorporated by reference herein in its entirety.

In some aspects of the invention a molecule of interest that an assay of the invention is used to identify is a polypeptide, and may be an oligomerized polypeptide. Characteristics of a molecule of interest may include, but are not limited to one or more of: presence/absence, level or amount, level of oligomerization, size, molecular weight, or another physical characteristic of the molecule. A binding agent that may be used in an embodiment of an assay of the invention is an antibody or functional fragment thereof that specifically binds the molecule of interest. For example, in certain aspects of the invention a binding agent is an antibody, or functional fragment thereof that selectively binds an oligomerized MAVS polypeptide complex.

In some embodiments of assay methods of the invention, levels of fluorescence of the detectable label used in the assay are determined at different steps in the assay. Differences in the level of fluorescence determined at different steps in the assay methods indicate characteristics of the molecule of interest. For example, though not intended to be limiting, a level of oligomerization of a MAVS polypeptide complex can be determined based on a finding that the level of fluorescence decreases following addition of the second binding compound to the assay sample/test sample mixture. The quenching of fluorescence is dependent on spectral overlap of absorbance and emission of the same fluorophore and the distance of the fluorophore to the metal bead. The more the quenching the closer the same dye is and the smaller the oligomer size is.

In previous FRET assay methods, it was expected that addition of fluorophores to any solution to lead to a fluorescence signal increases. However, the assay methods of the invention utilizes the finding that the increase in fluorescence signal is non-linear and that with increasing numbers of fluorophores attached to the molecule of interest bound to a binding agent, results in a decrease of fluorescence signal is decreasing due to excitation energy homo-transfer that is controlled by the Förster mechanism. Controlled excessive labeling may result in a significant decrease in both the total fluorescence signal and the average fluorescence lifetime. Self-quenching of fluorescence is an effect of non-fluorescent traps in the process of homo resonance energy transfer (RET) that act as a non-radiative "sink" for the excited state energy. Embodiments of assays of the invention are based, in part, on selective labeling of binding agents, which when coupled by the molecule of interest lead to decrease of fluorescence that correlated with the size of the molecule of interest. In certain aspect of assays of the invention, the assay includes use of selective labeling of antibodies that bind an oligomerized polypeptide complex, which when coupled by (bound to) the oligomerized polypeptide complex leads to decrease of fluorescence that correlates with the size of the oligomer.

Previous approaches to homo-FRET have included qualitative readouts of homo-FRET performed primarily using measurements of the steady state anisotropy where continuous wave excitation and detection provides the time average for imaging channels with the polarization resolved parallel and perpendicular to the incident polarization. However, although steady-state fluorescence anisotropy imaging experiments provide an effective approach to detect homo-FRET, they cannot be utilized in plate-based assays. Homo-FRET assays of the invention may be utilized in plate-based assays and also in high-throughput plate based assays.

Non-limiting examples of procedures that may be used in h-FRET assays of the invention include placing two or more identical dyes on a single antibody, which improves overall brightness and photostability of the assay system. In certain aspects of the invention, the labeling amount does not exceed more than 2 or 3 of fluorescence dye per antibody in order to exclude the possibility of self-quenching within the one not coupled antibody. Dyes useful in h-FRET methods may be dyes that are photostable, exhibit minimal blinking and are characterized by overlap integral between each one's absorption and emission spectra, which would lead to Förster energy resonance. The pair of dyes for use in an assay of the invention may be selected based on the size of oligomer to be detected. Various fluorescent dyes known in the art can be used in h-FRET assay methods of the invention, although suitable dyes are not limited to any particular commercially available dye.

To enhance detection or modulate the distance required for Förster energy resonance certain aspects of the invention may include coupling the antibodies to a plate that is monolayered with the metallic particles fabricated from Silver, Gold, Copper, Aluminum, Zinc, Nickel, Palladium, Tungsten, Platinum, Germanium, Indium, Iron, Tin, Rhodium or combinations thereof. Metal or carbon nanoparticles may be used in aspects of h-FRET of the invention to enhance the FRET efficiency through metal-fluorophore interaction, leading to an increase in quantum yield and emission intensity of the fluorophore and spectral overlap between the absorption and emission spectra. Some embodiments of h-FRET methods of the invention include tethering the metal bead with antibody either with standard linker peptides or with a novel idea of using DNA oligomers as the linker molecules. DNA oligomers based on their composition either wire or inhibit electron transport, which promotes fluorescence. Therefore the composition of DNA oligomer used in h-FRET methods depends on the desired enhancement or inhibition of fluorescence. A DNA oligomer used in embodiments of h-FRET methods of the invention may include either guanosine-cysteine base pairs, which enhance wiring of electrons from the metal to the peptide labeled with fluorophore or inosinse-cysteine or adenosine-thymidine, which have the opposite property and lead to inhibition of photo-induced electron transfer. DNA oligomer or peptide linkers used in some embodiments of h-FRET methods and assays of the invention may be varied in length to enhance or inhibit the electron transport based on the exhaustion of the electron transport with distance.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Materials/Methods
Cell Culture, Mice and Human Subjects.

MAVS-deficient and matching WT MEFs, gift of Z. J. Chen (Z. J. Chen et al. (2005) Cell 122, 669-682), were maintained in Dulbecco's modified Eagle's medium (DMEM) (Hyclone), supplemented with 10% heat-inactivated fetal calf serum (FCS) (Hyclone), 100 mM L-glutamine (Cellgro Mediatech), and 10,000 units/mL penicillin/10 mg/mL streptomycin sulfate (Life Technologies). C57BL6 or B6; 129-Mavstm1Zjc/J mice (The Jackson Laboratory, Bar Harbor, Me.) were maintained at the University of Vermont under a protocol approved by the Institutional Animal Care and Use Committee. Murine BMDCs were prepared as described by Inaba et al. (K. Inaba et al., (1992) Journal of Experimental Medicine 176, 1693-1702). In brief, cells derived from femur bone marrow were cultured at a density of $5 \times 10^5$/mL in 10-cm plates in RPMI 1640 (HyClone), supplemented with 5% heat-inactivated FCS, 100 mmol L-glutamine, 100 mmol sodium pyruvate, 10,000 units/mL penicillin/10 mg/mL streptomycin sulfate, $5 \times 10^{-5}$ mol 2-mercaptoethanol (Sigma, St. Louis, Mo.), and 10 µg/mL GM-CSF (Life Technologies). Human subjects were enrolled under a protocol approved by the University of Vermont Institutional Review Board. Samples from 17 SLE patients fulfilling the American College of Rheumatology diagnostic criteria were studied (E. M. Tan et al., (1982) Arthritis and Rheumatism 25, 1271-1277). 16 out of 17 patients were female, and the age of study participants was 47±3. The disease activity was assessed by the SLE disease activity index (SLEDAI) scores, ranging from 0 to 10 (C. Bombardier et al., (1992) Arthritis and Rheumatism 35, 630-640). Upon informed consent, primary human PBMCs were obtained from heparinized whole-blood samples from SLE patients. Control PBMCs were generated from age-, sex-, and ethnicity-matched healthy subjects. PBMCs were isolated using standard Ficoll gradient centrifugation as previously described (R. Mallone et al., (2011) Clin. and Exp. Immunol. 163, 33-49). Cells were either used immediately to prepare lysates for immunoblotting or cultured at a density of $5 \times 10^5$/mL in a 12-well culture plate with RPMI 1640 (HyClone), supplemented with 5% heat-inactivated FCS, 100 mmol L-glutamine, 100 mmol sodium pyruvate, and 10,000 units/mL penicillin/10 mg/mL streptomycin sulfate. Enriched monocytes from PBMCs were used to prepare hDCs using negative magnetic bead selection (Miltenyi), and were subsequently cultivated for 6 d in 10 µg/mL GM-CSF and 500 U/mL IL-4. All cells were maintained in a humidified chamber at 37° C. and 5% $CO_2$. Genotype information on the human subjects is provided in FIG. 11.

Virus Stocks.

The CVB3 H3 strain was derived from an infectious cDNA clone as previously described (K. U. Knowlton et al., (1996) J Virol 70, 7811-7818). SINV strain S.A.A.R.86, gift from R. E. Johnston, was derived from a genomic cDNA clone (D. L. Russell et al., (1989) Journal of Virology 63, 1619-1629). Viral titers were determined by plaque assay (0. W. Schmidt et al., (1979) Journal of clinical microbiology 9, 722-728). Infected MEFs were prepared by inoculating cells with CVB3 or SINV in DMEM at a multiplicity of infection (MOI) of 1. Cells remained in contact with the virus for 45 minutes to allow absorption then washed with phosphate buffered saline, resuspended in fresh medium, and incubated for the indicated time periods before assays were performed.

Reagents.

5' triphosphate double-stranded RNA (5'-ppp-dsRNA), a synthetic ligand for RIG-I, was purchased from InVivoGen and used at a concentration of 1 µg/mL. Mitochondria-targeted antioxidant MitoQ and the mitochondria-targeted superoxide generator MitoPQ, were gifts of M. Murphy (G. F. Kelso et al., (2001) The Journal of biological chemistry 276, 4588-4596). The control reagent TPP was purchased from Sigma. Reagents were added to cells at concentrations as indicated. GOx was purchased from Sigma and added to cultured cells at a final concentration of 0.1 U/mL. Iodoacetamide was from Thermo Fisher, and used at a final concentration of 100 µM.

Flow Cytometry.

ROS generation was measured using oxidized, green-fluorescent dihydrocalcein acetoxymethylester (DHC-AM) (Life Technologies) and flow cytometry. Single-cell suspensions of MEFs were prepared and ROS was assessed with 5 µM DHC-AM staining in culture medium for 30 minutes (A. Rohnstock et al., (2007) Toxicol in Vitro 21, 1552-1562). 25 nM of cationic cell permeant dye tetramethylrhodamine ethylester (TMRE; Life Technologies) (R. C. Scaduto, Jr. et al., (1999), Biophysical journal 76, 469-477) were used to measure $\Delta\Psi_m$. Additionally, MitoSox Red and MitoTracker Deep Red (Life Technologies) were used to measure mitochondrial ROS and mitochondrial mass, respectively. Flow cytometry was carried out on an LSRII (BD Biosciences), and FlowJo software (Tree Star) was used for analysis.

Metabolism Assay.

Real-time analysis of OCR and ECAR was performed with an XF-24 Extracellular Flux Analyzer (Seahorse Bioscience). Metabolic profiles were measured under basal conditions in non-buffered DMEM (Sigma) containing 25 mM glucose, 2 mM L glutamine, and 1 mM sodium pyruvate, in response to 1 µM oligomycin, 0.5 µM FCCP, and 1 µM rotenone/1 µM antimycin A (M. B. de Moura et al., (2014) Methods in molecular biology 1105, 589-602). Total ATP was measured with the ATP Lite Kit (Perkin Elmer), and the ATP/ADP ratio was determined using the bioluminescence ADP/ATP Ratio Assay Kit from Sigma.

Confocal Microscopy Imaging.

WT and MAVS-deficient MEFs were transfected using Neon Transfection System with roGFP-Mito2 (Addgene plasmid #49437). Mito-roGFP is a green fluorescent protein that targets the mitochondrial matrix and displays rapid changes in fluorescence in response to changes in ambient redox potential (G. T. Hanson et al., (2004) The Journal of Biological Chemistry 279, 13044-13053). After transfection, cells were seeded on poly-L-lysine-coated coverslips (Becton Dickinson) and cultivated in DMEM overnight to allow cell recovery and expression of roGFP, before infection with CVB3 or SINV. Mitochondrial localization and morphology were defined by staining cells with 100 nM Mitotracker Deep Red (Life Technologies) for 15 min prior to fixation with 2% formaldehyde. Coverslips were embedded with Aqua-Mount Slide Mounting Media (Polysciences) and analyzed with a Zeiss LSM 510 Meta confocal laser scanning microscopy system (63×N.A.=1.4 objective). Images were processed with Volocity 3D Image Analysis Software (Perkin Elmer).

IFN-I and Proinflammatory Cytokine Measurement.

ELISA was used to measure cytokine concentration in supernatant from cultured MEFs and BMDCs, and in sera of SLE patients and healthy control subjects. For assays, samples were centrifuged and IFN-β and IL-6 levels were measured in triplicate using murine or human ELISA kits according to the manufacturer's instructions. (PBL Biosciences). The fold change in IFN-I or IL-6 cells was calculated by directly comparing mock versus virus or chemical inducer of ROS.

Functional Reconstitution of Human M4 VS in MAVS-Deficient MEFs.

To reconstitute His-tagged human WT or C79F MAVS, 3 µg vector pIRES carrying the respective sequences, were transfected into $1 \times 10^6$ MAVS-deficient MEFs using Neon Transfection System (Life Technologies). To select for stably transfected cells, 2.5 µg/mL puromycin (Life Technologies) was added 24 h post-transfection for up to 5 days.

MAVS Knock-Down in MEF Using siRNA.

Where indicated, siRNA was used to knock-down MAVS in MEF (TRC MAVS shRNA, Thermo Fisher). 3 µg plasmid was transfected into 1×10$^6$ WT MEFs using Neon Transfection System (Life Technologies). To select for stably transfected cells, 2.5 µg/mL puromycin (Life Technologies) was added 24 h post-transfection for up to 5 days.

Anti-His-Tag Immunoprecipitation.

MEF were disrupted in lysis buffer and anti-His-tag antibody (Life Technologies) was used to immunoprecipitate MAVS. Purification of precipitated MAVS was performed on a MagMAX Express Magnetic Particle Processor (Thermo Fisher), and MAVS and co-immunoprecipitated proteins were separated by gel electrophoresis and detected by immunoblotting as indicated below.

Denaturing Gel Electrophoresis.

Cultured MEFs or human PBMCs were lysed in a sample buffer containing 2% SDS and insoluble cell fragments were removed by centrifugation. Plasma samples derived from SLE patients were collected and stored at −20° C. until gel electrophoresis. BCA protein assay (Thermo Scientific) was used to determine protein concentrations in all samples were resolved with SDS-PAGE under denaturing conditions. Gels were transferred to PVDF membranes using a Trans-Blot Turbo Transfer System (BioRad).

Semidenaturing Detergent Agarose Gel Electrophoresis (SDD-AGE).

SDD-AGE was performed according to a published protocol with minor modifications (Alberti et al., (2009) Cell 137, 146-158). In brief, mitochondria were resuspended in sample buffer (0.5×TBE, 10% glycerol, 2% SDS, and 0.0025% bromophenol blue) and loaded onto a vertical 1.5% agarose gel. After electrophoresis in the running buffer (1×TBE and 0.1% SDS) for 35 min with a constant voltage of 75 V at 4° C., proteins were transferred to PVDF membranes using a Trans-Blot Turbo Transfer System (Bio-Rad) for immunoblotting.

Immunoblot Analysis (Western Blotting).

PVDF membranes were blocked in 5% solution of nonfat powdered milk in Tris-buffered saline. Antibodies used were specific for MAVS and Actin (Santa Cruz); RIPK1 and TRAF2 (BD Biosciences); TANK, TRADD, RIG-I, and GAPDH (Cell Signaling); MDAS and COX4 (Abcam), Alexa 488 (Life Technologies), and IRF3 (Thermo Fisher), respectively. Immunoreactive proteins were visualized using HRP-labeled conjugates (Jackson Immuno Research) and developed using Clarity Western ECL substrate (Biorad). Chemiluminescence was detected and recorded using a Biorad Chemidoc instrument. Densitometric measurements were performed in Image Lab image acquisition and analysis software (Biorad).

Purification of MAVS-Oligomers, Mitochondrial Isolation, and Functional Assay.

MAVS antibody was covalently coupled to protein G magnetic beads (Life Technologies) using the bi-functional amine-reactive cross-linker disuccinimidyl suberate (DSS; Thermo Scientific). To avoid a sample contamination with proteins or protein complexes that nonspecifically bind to protein G, plasma samples were pre-incubated with protein G magnetic beads without the cross-linked MAVS antibody. SLE patient plasma were incubated for 6 hours, after which the magnetic beads were loaded onto a column in a magnetic field and extensively washed. After the beads were eluted, MAVS-oligomers were released from MAVS-antibody by way of increasing ionic strength buffer, lower pH and gel filtration. Functionally intact mitochondria from cultured cells were isolated as described earlier (S. Schmitt et al., (2013) Analytical biochemistry 443, 66-74). This method comprises a mechanical cell rupture, followed by a precipitation of mitochondria from cell lysates using magnetically labeled anti-TOM22 (Miltenyi Biotec) antibody. Mitochondria were inoculated with SLE patient or healthy control plasma in a respiration-promoting buffer containing 125 mM KCl, 5.0 mM KH$_2$PO, pH 7.25, 15 mM α-ketoglutarate and 2.0 mM ADP (A. C. Nulton-Persson, (2001) The Journal of biological chemistry 276, 23357-23361; L. A. Callahan et al., (2001) Free radical biology medicine 30, 129-138). The reaction mixtures were centrifuged at 10,000×g for 10 min, and the precipitates then analyzed using SDD-AGE.

Functional Assay of Endogenous MAVS Aggregation and Activation In Vitro.

Prior to enriching and labeling MAVS oligomers from the plasma, total plasma was treated with protein G magnetic beads alone and filtered with 100-kDa cut-off membranes to remove non-specific small-molecular-weight oligomers and cytokines. MAVS oligomers from plasma were then bound with anti-MAVS-protein G magnetic beads and coupled them to Alx546 or Alx488 while the MAVS oligomers were still bound to the MAVS antibody tethered to magnetic beads to remove excess dye without passing the material through another size-exclusion resin. Purified MAVS oligomers from SLE patient plasma were fluorescently labeled using either Alx488- or Alx546-hydrazine (Life Technologies). Labeled MAVS oligomers were cocultivated with either BMDCs derived from WT or MAVS-deficient mice, or hDCs. Both murine BMDCs and human DCs were incubated for 1, 2, or 6 h. Confocal microscopy was used to analyze Alx546 fluorescence and its location. DCs were cultured on poly-L-lysine-coated coverslips and stained with MitoTracker Green (Life Technologies) and Hoechst 33342 prior to fixation with 4% formaldehyde to define mitochondria and nuclei.

Genotyping of SLE Samples.

Genomic DNA was extracted using Qiagen's DNeasy Blood and Tissue Kit per manufacture instructions. Unique genomic primers flanking MAVS Cys79 were designed using Primer-Blast [forward primer (FP) ccctgggggccatat-taatcc (SEQ ID NO:22)/reverse primer (RP) cat-caaatcgcctccgagca (SEQ ID NO:23)] and used both to PCR amplify and sequence exon2.

Analysis of Mitochondrial Morphology by Transmission Electron Microscopy.

For ultrastructural analysis, cells were fixed for 1 h at 65° C. in 2% paraformaldehyde and 2.5% glutaraldehyde (Polysciences) in 100 mM sodium cacodylate buffer, pH 7.2. Samples were washed in cacodylate buffer and then post-fixed for 1 h in 1% osmium tetroxide (Polysciences). Samples were then extensively rinsed in distilled H$_2$O before en bloc staining for 1 h with 1% aqueous uranyl acetate (Ted Pella). After several rinses in distilled H$_2$O, samples were dehydrated in a graded series of ethanol and then embedded in Eponate 12 resin (Ted Pella). Sections (95 nm in thickness) were cut with an Ultracut UC7 ultramicrotome (Leica Microsystems), then stained with uranyl acetate and lead citrate, and viewed on a JEOL 1400 transmission electron microscope (JEOL USA) equipped with an AMT XR611 high resolution 11 megapixel midmount CCD camera (Advanced Microscopy Techniques).

Results

MAVS Oligomerization Decreases ATP Production and Mitochondrial Spare Respiratory Capacity.

Figure 1D:
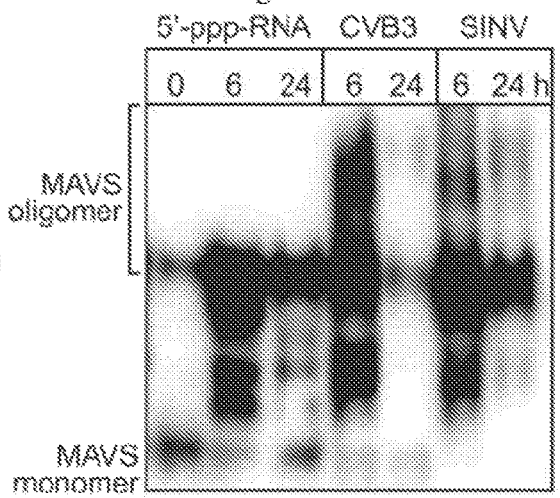
FIG. 1D shows results when MAVS oligomerization in MEFs in response to CVB3 or SINV infection, or 5'-ppp-RNA transfection, was detected at the time points indicated using non-reducing gels and immunoblotting. Results were similar in three independent experiments.
Figure 1E:
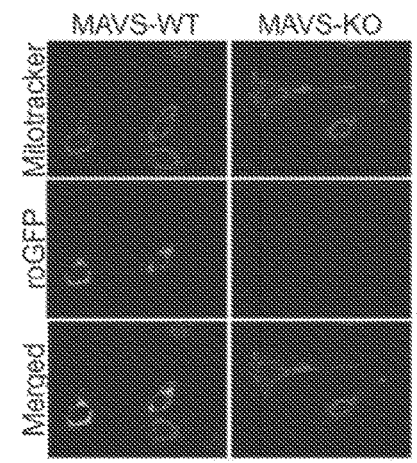
FIG. 1E shows results when the cellular source of ROS in CVB3-infected MEFs, Mito-roGFP-expressing MAVS-WT and MAVS-KO MEFs were analyzed 6 h following infection. MitoTracker Deep Red was used at 1 μM as a counterstain to define mitochondria. Confocal microscopic images are representative of three independent experiments.

Experiments were performed to examine mitochondrial function and metabolism in wild-type (WT) or MAVS-deficient (MAVS-KO) mouse embryonic fibroblasts (MEFs)

during infection with either Coxsackievirus B3 (CVB3), Sindbis virus (SINV), or after transfection with an RNA containing a triphosphate incorporated at the 5' end (5'-ppp) that is a specific ligand for RIG-I. Both CVB3 and SINV are single-stranded, positive-sense RNA viruses with the ability to activate the RIG-I pathway (V. Hornung et al., (2006) Science 314, 994-997). However, unlike SINV, CVB3 has the additional ability to cleave MAVS at Gln148 with its 3$C^{pro}$ protease (A. Mukherjee et al., (2011) PLoS pathogens 7, e1001311). During the initial 12 h following CVB3 and SINV infection, or 5'ppp RNA transfection, it was observed that both ROS and mitochondrial membrane potential ($\Delta\Psi_m$) increased (FIGS. 1, A and B). However, beyond the 12 h time point, in contrast to SINV and 5'ppp-RNA, CVB3-induced cleavage of MAVS paralleled a marked reduction in cellular ROS and $\Delta\Psi_m$ (FIGS. 1, A to C). Changes in $\Delta\Psi_m$ and ROS during viral infection or 5'-ppp-RNA stimulation also correlated positively with MAVS oligomerization (FIG. 1D). Particularly striking was that no increase in ROS or $\Delta\Psi_m$ was observed during viral infection of MAVS-KO cells (FIGS. 1, A and B). This was also true of cells expressing a truncated form of MAVS cleaved at Gln148, which lacks the CARD domain required for MAVS oligomerization (FIG. 8). Using the mitochondria-targeted, redox-sensitive di-cysteine green fluorescent protein (roGFP) as a probe (Hanson, G. T. et al., 2004 J. Biol. Chem 2004 Mar. 26; 279(13):13044-53), it was determined that the increased matrix thiol oxidation during viral infection or stimulation with 5'-ppp-RNA originated primarily in mitochondria (FIG. 1E).

Figure 1F:
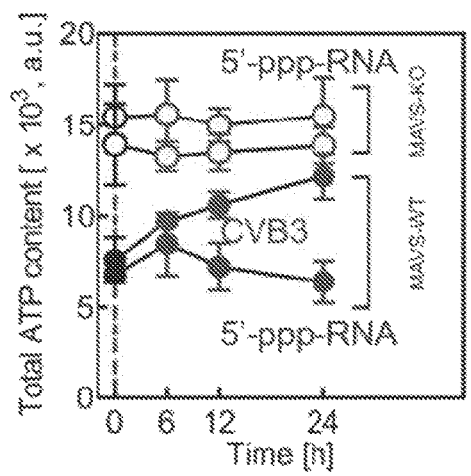
FIG. 1F shows total ATP content of MAVS-WT and MAVS-KO MEFs after infection with CVB3 or transfection with 5'-ppp-RNA over a 24 h period that was measured using a luminescence-based assay. ATP levels across the 24 h period in mock infected WT or MAVS-KO cells are shown as controls.
Figure 1G:
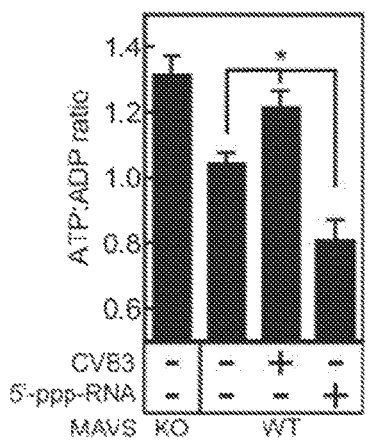
FIG. 1G shows results of ATP/ADP ratio in the same cells that was measured 24 h after infection, or transfection, respectively. ATP and ATP/ADP ratios were determined in two independent experiments.

Elongation and further swelling of mitochondria was observed following viral infection and 5'-ppp-RNA exposure (FIG. 8). To establish whether MAVS influences cellular metabolism during an innate immune response to viral infection, total ATP production (FIG. 1F) and the ATP/ADP ratio (FIG. 1G) in MAVS-WT and MAVS-KO cells were measured before and following infection with CVB3, or transfection with 5'-ppp-RNA. Interestingly, it was observed that prior to infection MAVS-KO cells manifested a nearly 3-fold higher amount of cellular ATP than MAVS-WT cells (FIG. 1F). This high quantity of ATP in MAVS-KO cells correlated with a higher ATP/ADP ratio (FIG. 1G). Following CVB3 infection, the total ATP and ATP/ADP ratio increased 2-fold in MAVS-WT cells but did not increase further in MAVS-KO cells (FIGS. 1, F and G). Increase in ATP production or the ATP/ADP ratio following CVB3 infection in MAVS-WT cells approached the total steady state of ATP in MAVS-KO cells (FIGS. 1, F and G), and corresponded closely with the cleavage pattern of MAVS during CVB3 infection (FIG. 1C) is suggestive of a causative relationship. Interestingly, the same increase was not observed in ATP/ADP in cells transfected with 5'-ppp-RNA, which can continually activate RIG-I and MAVS oligomerization. In this case, following a small spike, the amount of ATP declined over time (FIG. 1F), suggesting that RIG-I and MAVS activation lowered the total quantity of ATP in the cells.

Figure 1H:
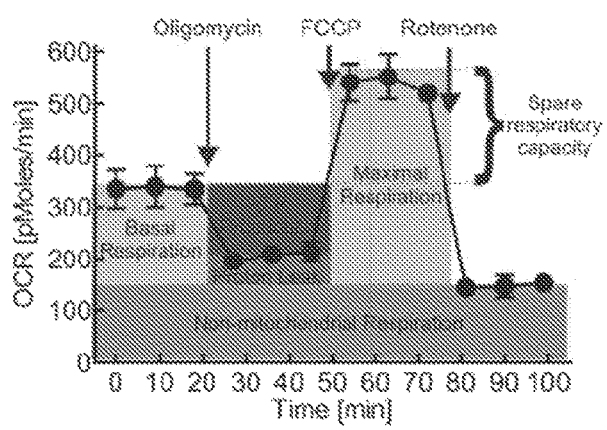
FIG. 1H illustrates a representative scheme, adapted from Seahorse Bioscience, of OCR measurement using a Seahorse XF24 Analyzer. Measurement of OCR in response to the injection of the ATP synthase inhibitor oligomycin, uncoupler FCCP, and complex I and III inhibitors rotenone and antimycin A, allowed for the calculation of the key metabolic parameters of basal mitochondrial respiration, maximal respiration, and spare respiratory capacity.
Figure 1I:
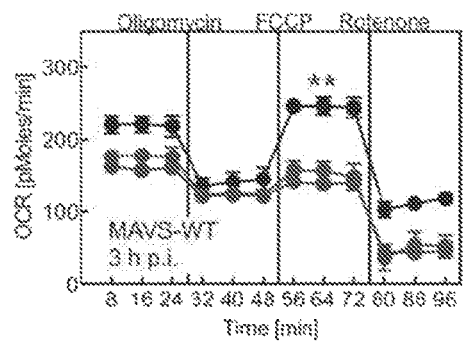
FIG. 1I-N shows OCR measurements of MAVS-WT (FIGS. 1I & J, closed symbols) and MAVS-KO (FIGS. 1K & L, open symbols) MEFs as a function of CVB3 infection or 5'-ppp-RNA transfection. Measurements were made 3 h (FIGS. 1I & K) or 24 h (FIGS. 1J & L) post infection, or transfection. MAVS-WT and MAVS-KO cells were measured simultaneously in the same assay plate, and data represent three experiments shown as mean±SEM.
Figure 1J:
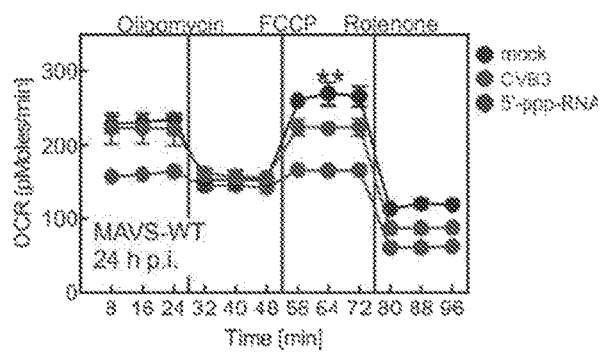
Figure 1K:
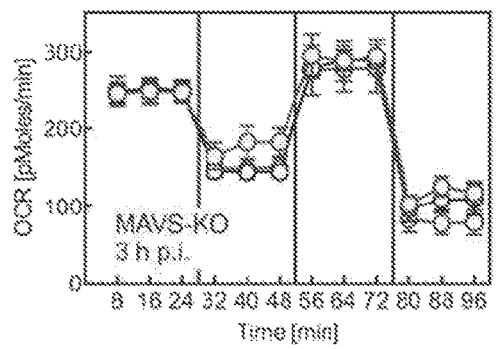
Figure 1L:
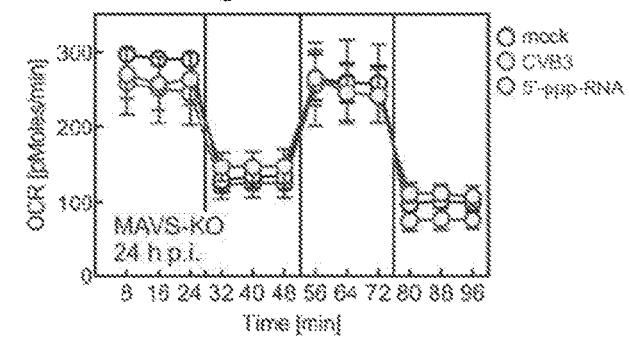
Figure 1M:
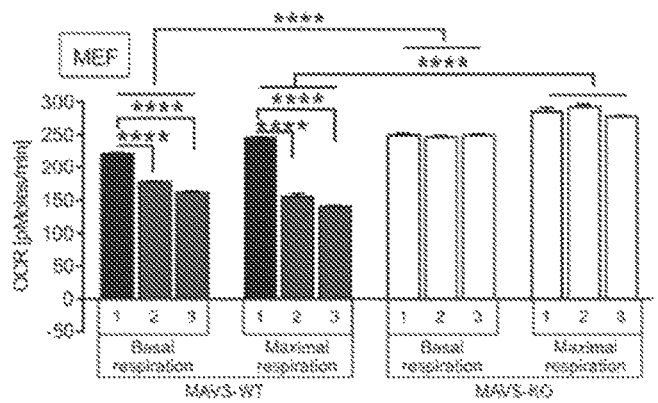
Figure 1N:
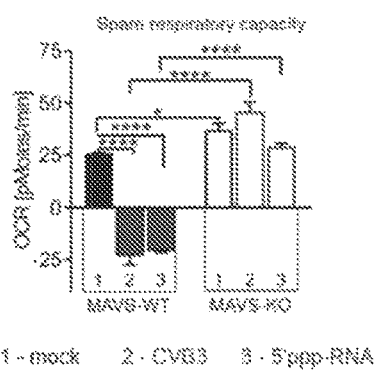
Figure 1O:
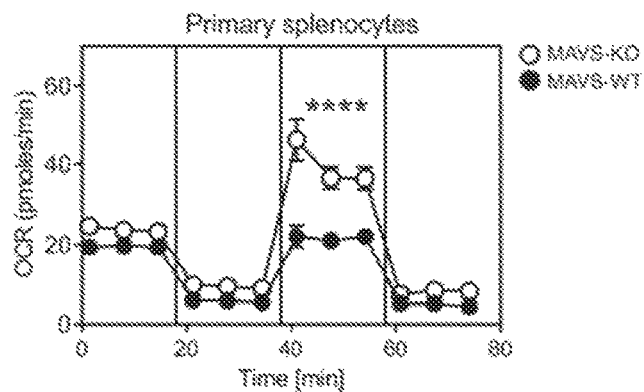
FIGS. 1O & P shows OCR measurements from splenocytes of MAVS-WT (closed symbols) and MAVS-KO (open symbols) mice. Statistical analyses performed were: two-way ANOVA. Statistical analyses performed were one-way ANOVA, followed by Sidak's Multiple Comparison Test to examine pair-wise differences, two-way ANOVA, or Repeated Measures ANOVA, followed by Tukey's Multiple Comparisons Test to examine specific comparisons, as appropriate. (*$p<0.05$, $p<0.005$, *$p<0.0005$, ****$p<0.00005$).
Figure 1P:
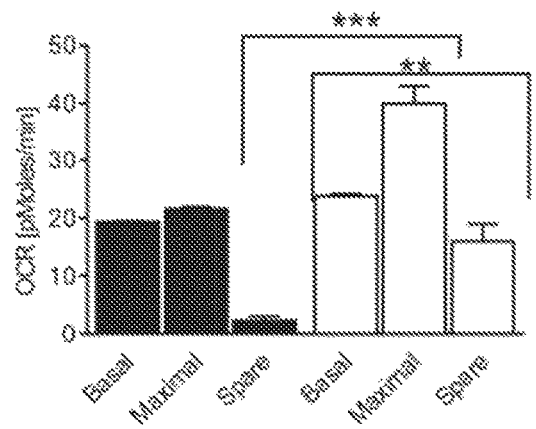

To further assess the bioenergetic profile during viral infection in the presence or absence of MAVS, the oxygen consumption rate (OCR) was examined as an indicator of oxidative phosphorylation using a Seahorse extracellular flux analyzer (M. Wu et al., (2007) American Journal of physiology, Cell Physiology 292, C125-136). To assess mitochondrial respiratory capacity we sequentially treated cells with oligomycin (to block ATP synthesis), the ionophore FCCP (to uncouple mitochondria and thereby maximally stimulate the electron transport chain (ETC)), and rotenone (to block ETC complex I) (FIG. 1H). It was observed that CVB3-infection and 5'-ppp-RNA-treatment of MAVS-WT cells manifested significantly lower basal OCR than mock-treated cells, and a very minimal response to FCCP treatment, suggesting impaired spare respiratory capacity (SRC) (FIGS. 1, I and J). Three hours post-infection, at a time when the CVB3 3$C^{pro}$ protease had produced only a small amount of cleaved MAVS (FIG. 1C), the metabolic profile of CVB3-infected cells did not differ from cells transfected with 5'-ppp-RNA (FIG. 1I). However, the same metabolic profile measured at 24 h when CVB3 3$C^{pro}$ had significantly cleaved MAVS, showed that CVB3-infected cells, but not 5'-ppp-RNA transfected cells, returned to basal capacity of OCR and SRC (FIG. 1J). Under the same conditions, MAVS-KO cells showed higher baseline OCR and SRC than MAVS-WT cells but, unlike MAVS-WT cells, this state did not significantly change with CVB3 infection or 5'-ppp-RNA treatment. (FIGS. 1, K and L). The findings from three separate OCR studies in MAVS-WT vs MAVS-KO MEFs is summarized in FIGS. 1M and N. As prolonged cell culture can impact the phenotype of MEF, we tested whether metabolic differences are indeed due to the differences in genotype using primary splenocytes from MAVS-WT vs MAVS-KO mice and observed the same phenotype as in MEFs (FIGS. 1, O and P). In contrast to the differences in oxygen consumption, the basal extracellular acidification rate (ECAR), a readout of lactate production by glycolysis, was very similar between MAVS-WT and MAVS-KO MEFs (FIG. 8). Collectively, these findings suggest that MAVS oligomerization inhibits mitochondrial respiration and ROS production.

Oxidative Stress Independent of Viral Infection Induces M4 VS Oligomerization.

Figure 2A:
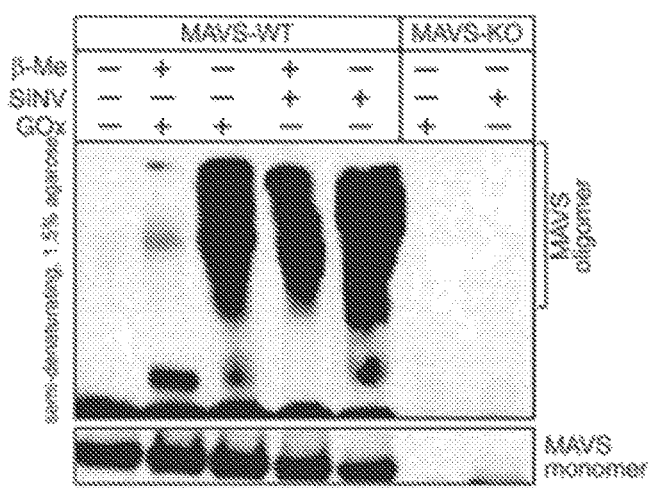
FIG. 2A-K provides graphs, and blots illustrating that virus-independent, oxidative stress induces MAVS oligomerization and IFN-I secretion.
Figure 2B:
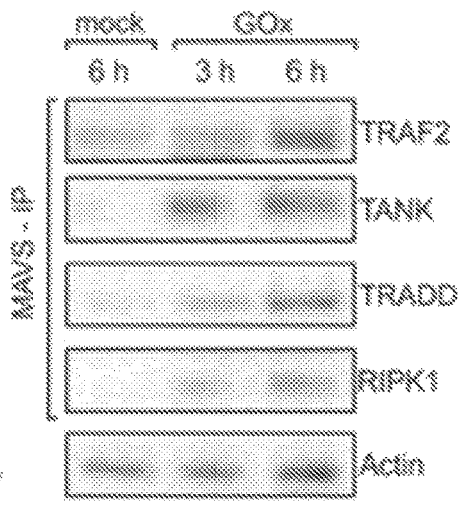
Figure 2C:
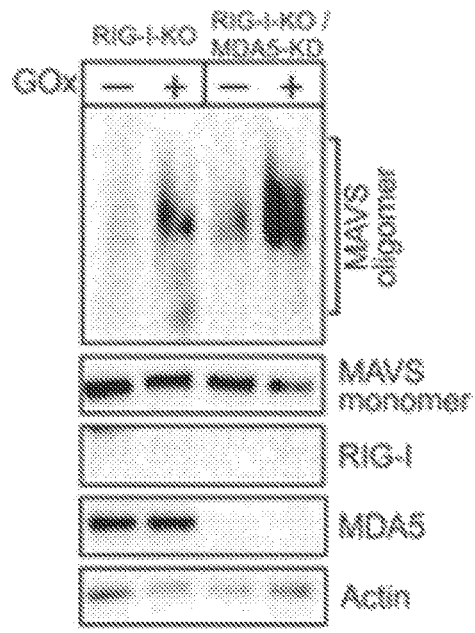
Figure 2D:
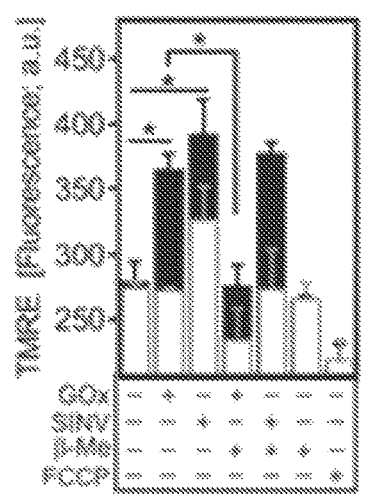
Figure 2E:
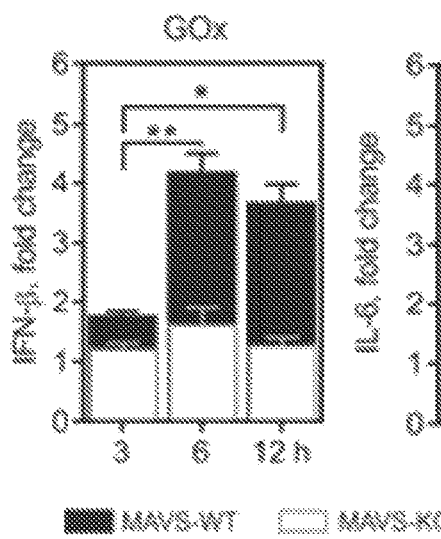
Figure 2F:
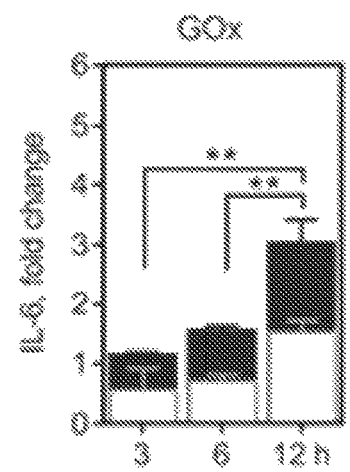
Figure 2G:
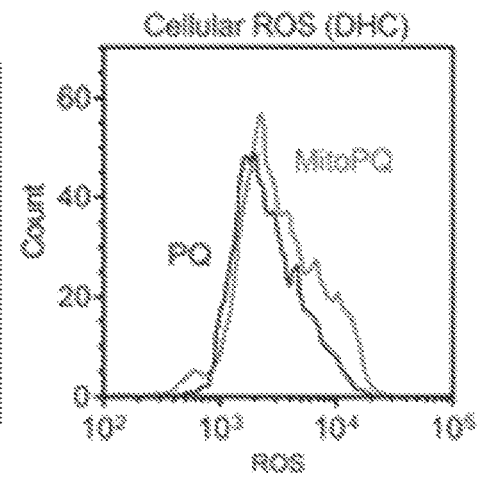
Figure 2H:
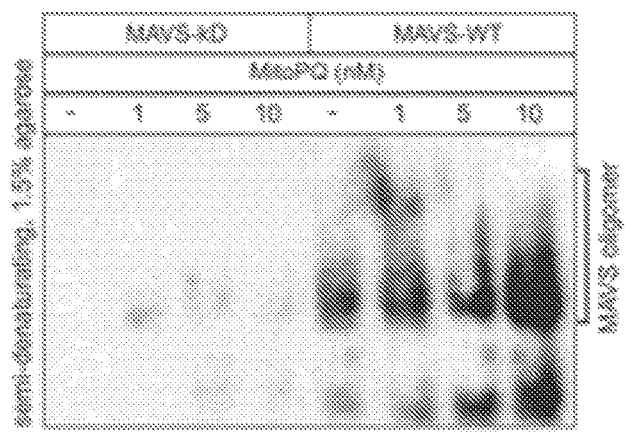
Figure 9A:
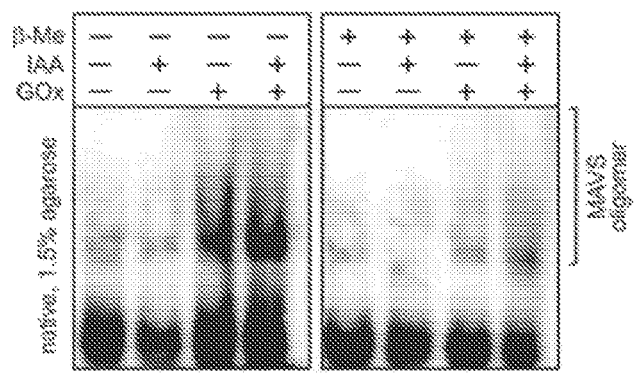
FIG. 9A-B shows blots of results of studies demonstrating that MAVS oligomers are not artificially formed during sample processing, homogenization or lysis.
Figure 9B:
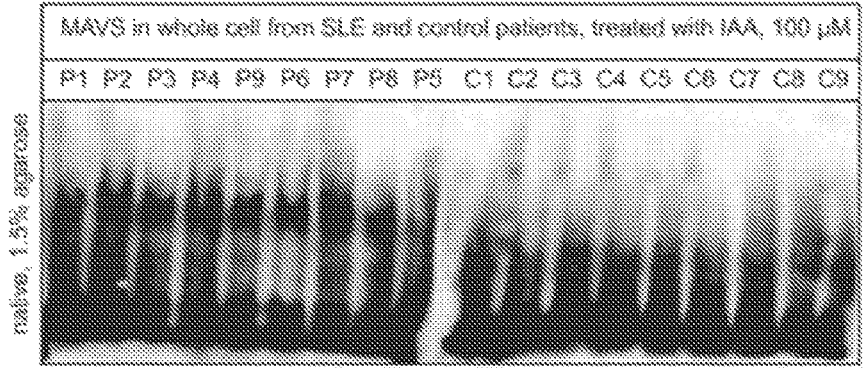
Figure 10A:
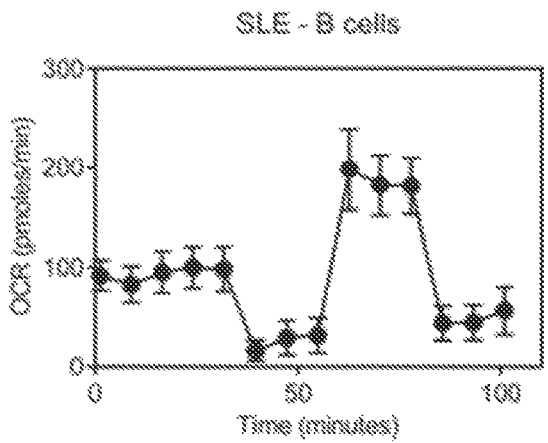
FIG. 10A-F provides graphs of results from analysis of mitochondrial respiration in PBMC subpopulations. OCR in B cells (FIG. 10A), T cells (FIG. 10B) and monocytes (FIG. 10C) isolated from patients with SLE was measured following the sequential addition of oligomycin, FCCP, and a combination of antimycin A and rotenone. B cells, T cells and monocytes (FIGS. 10D, E, and F, respectively) from healthy individuals served as controls. Shown are representative data of three independent experiments.
Figure 10D:
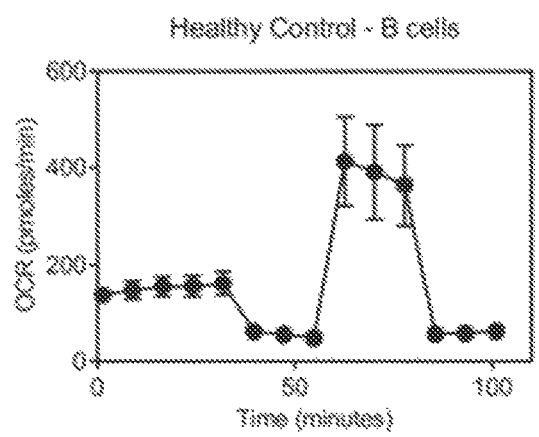
Figure 10B:
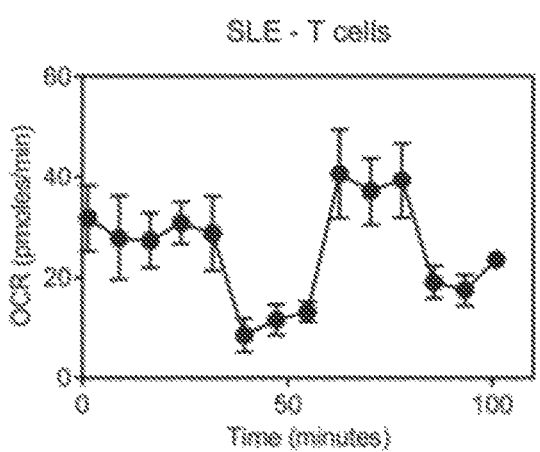
Figure 10E:
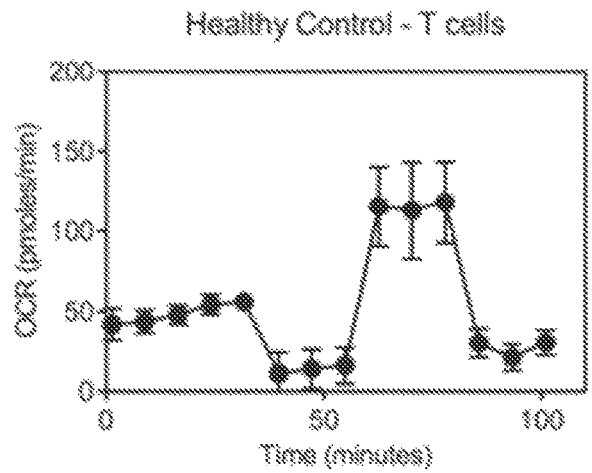
Figure 10C:
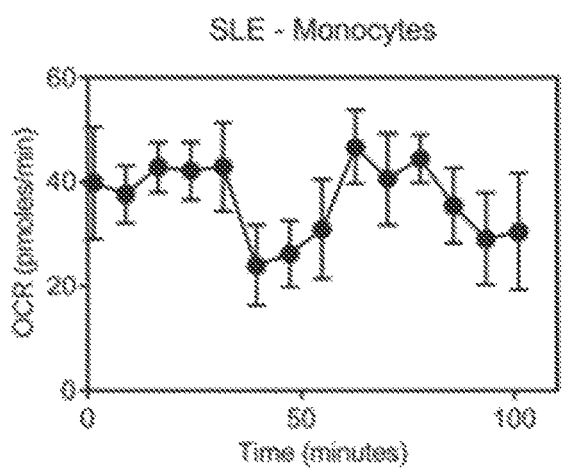
Figure 10F:
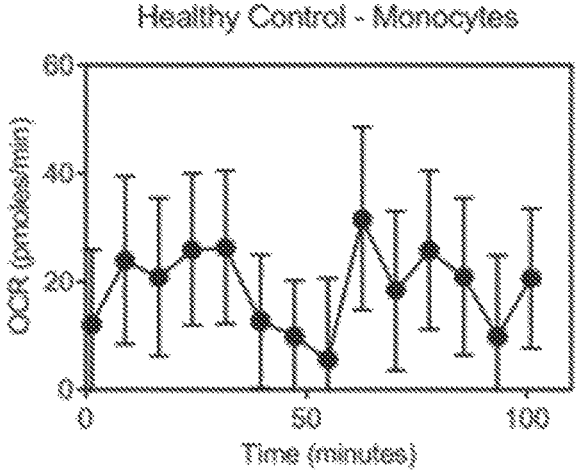

To further evaluate the influence of oxidative stress on MAVS oligomerization in the presence or absence of viral infection, studies were performed using two gel systems. First, a Tris-Glycine-eXtended (TGX) gradient polyacrylamide gel system was adapted to detect with high resolution MAVS aggregates (K. M. Monteiro et al., (2012) PLoS Negl Trop Dis 6, e1551). Second, to better detect the total amount of MAVS oligomers, Tris-Glycine agarose gels were used, which allow improved migration of large molecular weight complexes (F. Hou et al. (2011) Cell 146, 448-461). MAVS oligomerization was assessed during chemically induced oxidative stress using glucose oxidase (GOx), which generates $H_2O_2$ in the process of catalyzing the oxidation of glucose to D-glucono-δ-lactone, and it was compared with SINV infection (Q. H. Gibson et al., (1964) The Journal of biological chemistry 239, 3927-3934). At concentrations of 10-20 μg/mL, GOx increases cytoplasmic ROS at a quantity close to those observed during viral infection (W. S. Chong et al., (2012) Korean J Anesthesiol 62, 166-171). It was observed that GOx-mediated oxidative stress alone was sufficient to induce MAVS oligomerization, in a manner similar to SINV infection (FIG. 2A). Of interest, GOx-induced MAVS oligomerization was reversible when cell media were supplemented with β-mercaptoethanol (β-Me) (FIG. 2A). This was much less apparent during SINV infection, where only a portion of the MAVS oligomers were reducible. This difference could reflect the fact that virus-induced oligomerization of MAVS involves both RIG-I-CARD/MAVS-CARD dimerization as well as ROS-induced MAVS oligomerization, whereas GOx involves only the latter process. To address the possibility that the observed MAVS oligomerization might be an artifact of cysteine dimerization induced during cell lysis and processing for electrophoresis, freshly prepared cells were homogenized in buffer containing iodoacetamide, which covalently binds to free thiol groups of cysteines to prevent further disulfide bond formation. The presence of 100 µM iodoacetamide did not result in a decrease in MAVS oligomers either following GOx treatment or SINV infection (FIG. 9). MAVS oligomerization induced by GOx also led to the formation of the MAVS signaling complex as detected by co-precipitation of MAVS via its N-terminal His-tag. Within 3 h post ROS induction, we observed the association of TRAF2, TANK, TRADD, and RIPK1 with MAVS, suggesting that both interferon regulatory factors and the NF-κB branch of the MAVS signaling complex had occurred (FIG. 2B). GOx-induced MAVS oligomerization also occurred in the absence of RIG-I or MDA5 (FIG. 2C), and correlated with increased $\Delta\Psi_m$ (FIG. 2D), and increased secretion of IFN-I and IL-6 (FIGS. 2, E and F). The changes were not observed in cells lacking MAVS (FIG. 2, D to F). In agreement with the ability of β-Me to reverse MAVS oligomerization, supplementation of media with β-Me also prevented mitochondrial hyperpolarization in cells treated with GOx, but not following SINV infection (FIG. 2D).

Figure 2I:
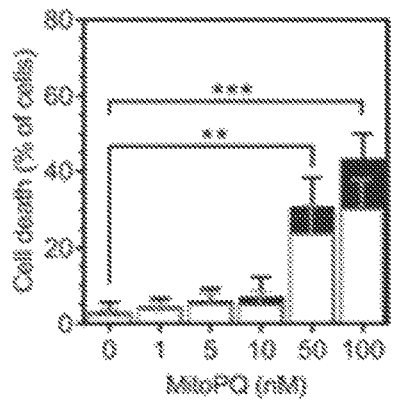
Figure 2J:
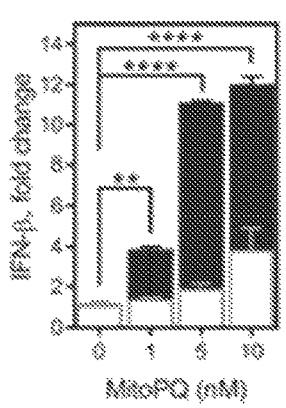
Figure 2K:
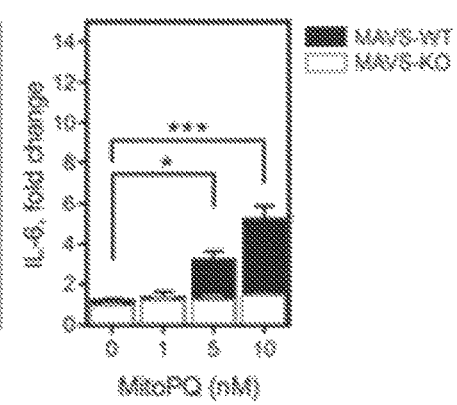

To determine whether ROS derived specifically from mitochondrial respiration could also induce MAVS oligomerization, experiments were performed that used the compound MitoParaquat (MitoPQ), a mitochondria-targeted superoxide generator that contains a paraquat moiety tethered to a positively charged lipophilic triphenylphosphonium (TTP) cation that drives MitoPQ accumulation within negatively charged mitochondria (E. L. Robb et al., (2015) Free radical biology and medicine 89, 883-894). Treatment of MEFs with moderate concentrations of MitoPQ (1 to 10 nM) led to an increased amount of superoxide within mitochondria (FIG. 2G), and MAVS oligomerization (FIG. 2H), without causing significant cell death at the doses used (FIG. 2I). Treatment of cells with MitoPQ also led to significant increase of IFN-I and IL-6 secretion that was not observed in MAVS-KO cells treated with MitoPQ (FIGS. 2, J and K). These findings support the view that mROS alone in the absence of viral infection is sufficient to induce MAVS oligomerization and downstream cytokine signaling.

Mitochondria-Targeted Antioxidant MitoQ Reduces MAVS Oligomerization and IFN-I Secretion.

Figure 3A:
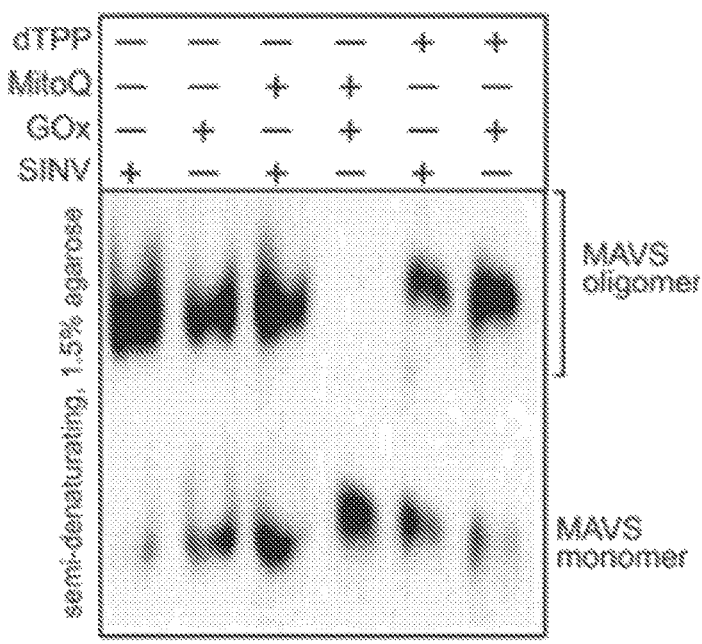
FIG. 3A-D shows a blot and graphs indicating that the mitochondria-targeted antioxidant MitoQ prevents MAVS-oligomerization.
Figure 3B:
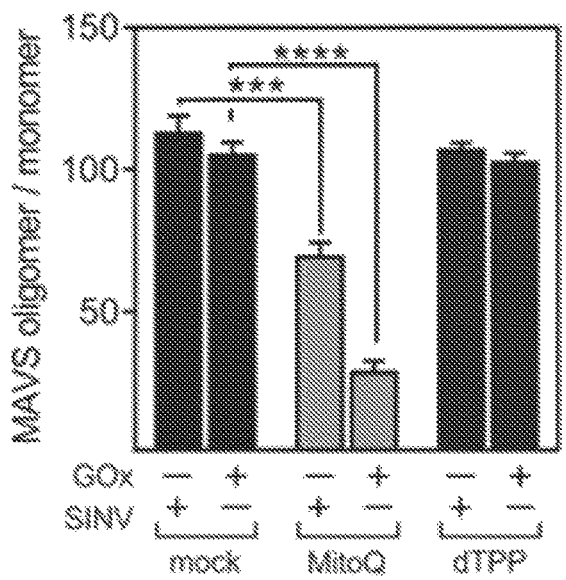
Figure 3C:
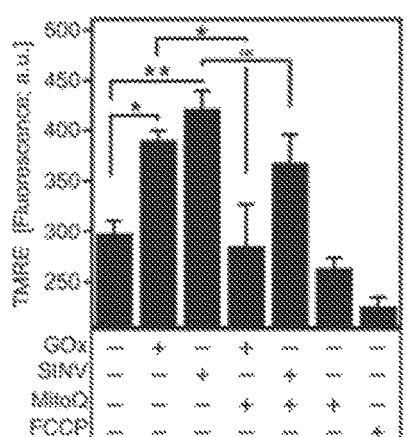
Figure 3D:
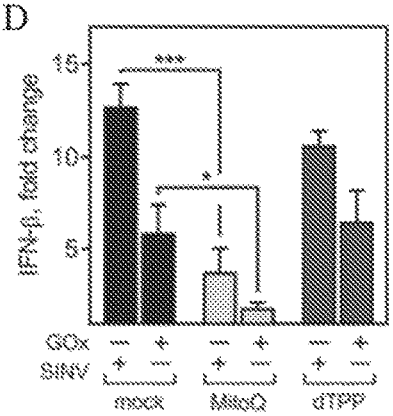

MitoQ ([10-(4,5-Dimethoxy-2-methyl-3,6-dioxo-1,4-cyclohexadien-1-yl)decyl](triphenyl)phosphonium methanesulfonate) is a mitochondria-targeted antioxidant comprised of ubiquinol/ubiquinone bound to TTP (G. F. Kelso et al. (2001) J. Biol. Chem 276, 4588-4596). In mitochondria, MitoQ is continually recycled to the active ubiquinol antioxidant by complex II in the respiratory chain (G. F. Kelso et al. (2001) J. Biol. Chem 276, 4588-4596 and A. M. James et al., (2005) The J of Biol Chem 280, 21295-21312). In experiments, cells pretreated with MitoQ prior to oxidative stress showed reduced MAVS oligomerization, which was more pronounced in cells treated with GOx than with SINV infection (FIG. 3A). MitoQ treatment led to at least an 80% decrease in MAVS oligomers in cells treated with GOx, whereas in cells infected with SINV MitoQ resulted in about a 40% decrease in MAVS oligomerization (FIG. 3B). As a control, cells pretreated with dTPP, which has the same mitochondria-targeting motif as MitoQ but lacks its antioxidant properties, did not demonstrate reversal of MAVS oligomerization due to SINV or ROS induction (FIG. 3A). Similar to the findings with β-Me treatment, the results with MitoQ again suggest that the nature or intensity of MAVS oligomerization induced by direct oxidative stress might differ from that stimulated by viral infection in which there is the additional heterodimerization of RIG-I-CARD with MAVS-CARD. Decreased MAVS oligomerization in the presence of MitoQ correlated with decreased mitochondrial hyperpolarization (FIG. 3C) and reduced IFN-I secretion (FIG. 3D).

MAVS Oligomerizes in Human PBMCs Under Oxidative Stress and Spontaneously in SLE Patients.

Figure 4A:
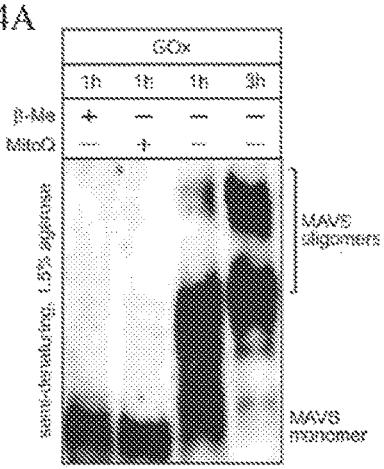
FIG. 4A-N shows blots and graphs demonstrating that virus-independent oxidative stress induces MAVS-oligomerization in human PBMC, and SLE patients manifest spontaneous MAVS oligomerization.
Figure 4B:
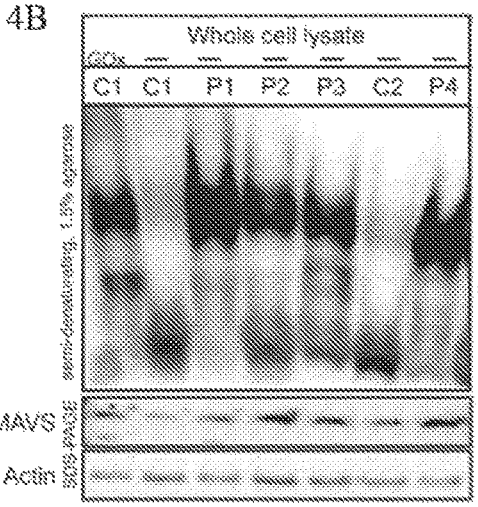
FIGS. 4B & C shows results when whole cell lysates (FIG. 4B) and plasma (FIG. 4C) of SLE patients (n=8, P1-P8) were detected by semi-denaturing agarose gel electrophoresis. Healthy, sex-, age-, and ethnicity-matched subjects served as controls (n=8, C1-C8).
Figure 4C:
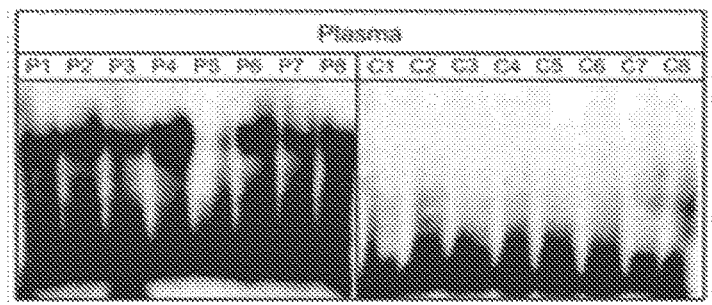
Figure 4D:
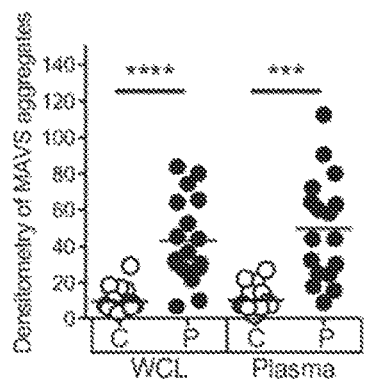
FIG. 4D shows MAVS oligomerization in whole cell lysates (left panel) and plasma (right panel) of SLE patients (black circles) and healthy control subjects (white circles) that was quantified by densitometric measurement of immunoblots. In WCL a ratio of MAVS monomer and oligomer was measured and in plasma MAVS oligomers were normalized to the level of albumin. Each point represents MAVS oligomerization of one individual, which was determined in at least three independent experiments.
Figure 4E:
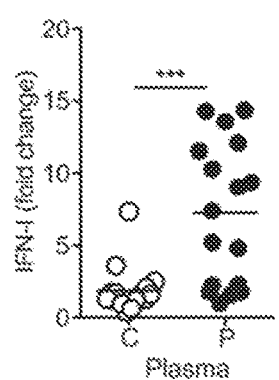
FIG. 4E shows results when IFN-I secretion expression was measured by ELISA and compared to a commercially available standard plasma from healthy individual.

The experimental finding in MEFs were extended to human PBMCs from healthy donors and it was observed that GOx induced pronounced MAVS oligomerization that appeared to be progressive, as distinct MAVS bands of ~750 and >1200 kDa (FIG. 4A) were identified. As observed in MEFs, MAVS oligomerization did not occur in PBMCs pretreated with MitoQ or grown in the presence of β-Me (FIG. 4A).

Figure 4F:
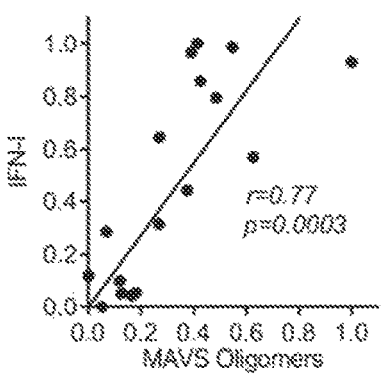
FIG. 4F provides a comparison of plasma IFN-I and degree of MAVS oligomerization in SLE patients.
Figure 4G:
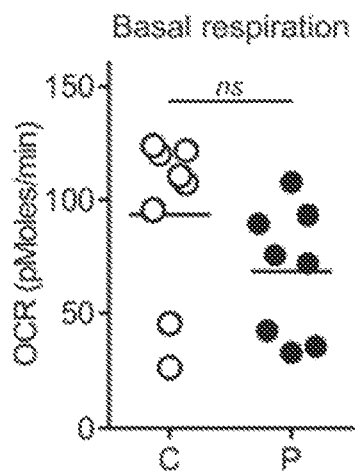
FIG. 4G-J shows results of OCR determinations of basal respiration (FIG. 4G), maximal respiration (FIG. 4H), spare respiratory capacity (FIG. 4I), and ATP synthesis (FIG. 4J) from SLE patients (P) and healthy controls (C).
Figure 4H:
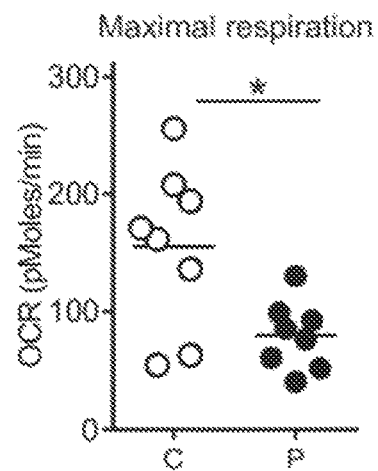
Figure 4I:
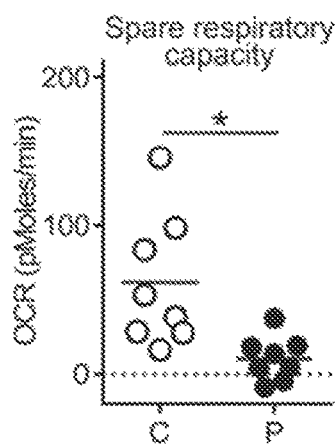
Figure 4J:
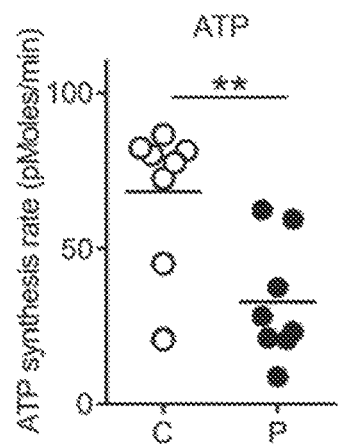

Experiments were performed to test whether MAVS is spontaneously oligomerized in PBMCs from SLE patients compared to age- and sex-matched healthy controls. Spontaneous MAVS oligomerization was assessed by agarose gel separation and was identified in the PBMCs of 14 of 17 SLE patients, whereas weak oligomerization was observed in 4 of the 17 healthy controls (FIGS. 4, B and D). MAVS oligomers were also detected in the plasma of 12 of 17 SLE patients but not in healthy controls (FIGS. 4, C and D). To exclude the possibility that the observed MAVS oligomerization spontaneously occurred during cell isolation from blood samples we added iodoacetamide, which did not decrease the detection of MAVS oligomers in cells or plasma (FIG. 9). Iodoacetamide reduced the total thiol concentration of both PBMCs and plasma homogenates by 80% and 94%, respectively (FIG. 9). These data demonstrate that MAVS oligomers are not artificially formed during tissue homogenization and processing, and further indicate that MAVS oligomers are stable in plasma. SLE plasma contained higher IFN-I than healthy controls (FIG. 4E) and the amount of IFN-I closely paralleled the degree of plasma MAVS oligomerization (FIG. 4F). Metabolic analysis of PBMCs of SLE and healthy controls identified no difference in basal respiration (FIG. 4G), but showed statistically reduced maximal respiration, spare respiratory capacity, and the rate of ATP synthesis in the SLE patients (FIG. 4, H to J). These findings are similar to changes in respiratory capacity observed during MAVS oligomerization induced by viral infection (FIG. 1, I to N).

Figure 4K:
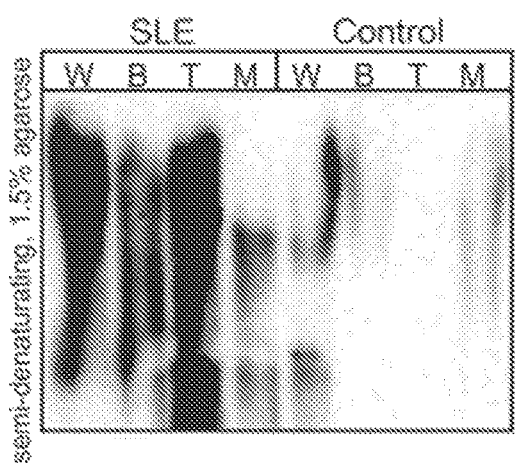
FIG. 4K shows MAVS oligomer measurements in unfractionated whole PBMC (W), or B cell (B), T cell (T), and monocyte (M) fractions. Findings are representative of three patients and controls examined.
Figure 4L:
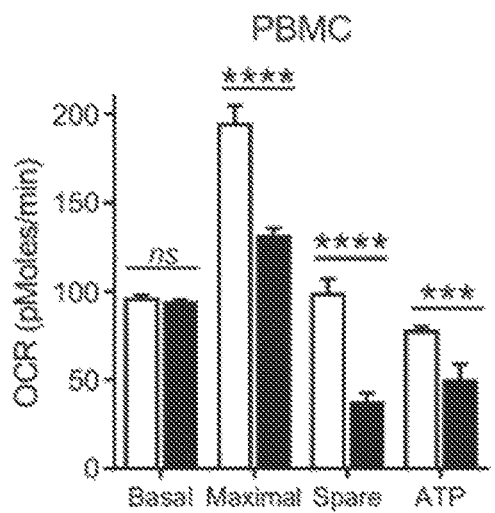
Figure 4M:
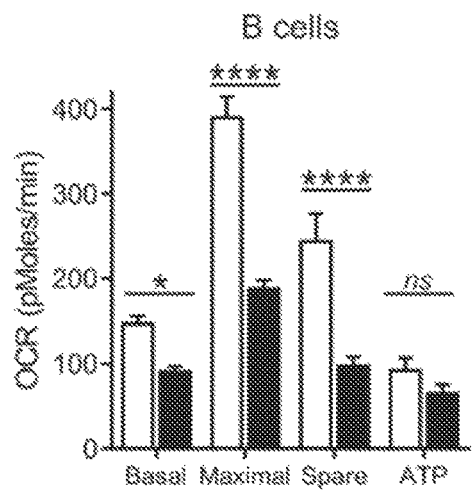
Figure 4N:
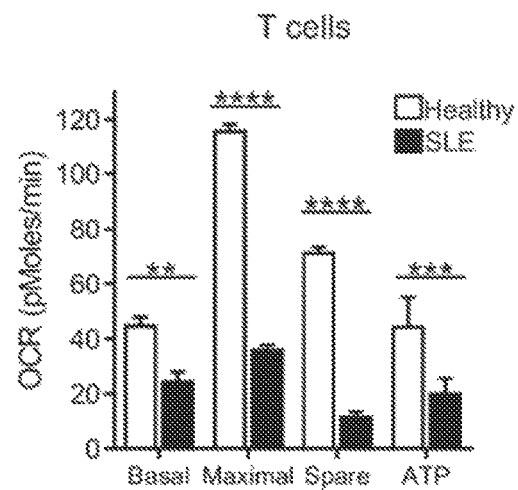

To further explore which subsets of cells within the PBMC population contributed to MAVS oligomerization in SLE patients, PBMC were fractionated into T cell, B cell, and monocyte pools, and each was analyzed for the presence of MAVS aggregates. As shown in FIG. 4K, for equivalent amounts of protein, T cells manifested the greatest amount of MAVS oligomers, followed by B cells with relatively little detected in monocytes. MAVS oligomers were not observed in the same cell subsets of healthy controls. Metabolic analysis of PBMC subsets showed that monocytes, unlike B and T cells, did not show strong oxidative phosphorylation (FIG. 10). Although basal, maximal and spare respiratory capacity were significantly reduced in both B cells and T cells of SLE patients, the reduction of these parameters in T cells was at least two-fold greater (FIG. 4, L to N). Noteworthy, the rate of ATP synthesis was decreased only in T cells, not significantly in B cells, of SLE patients (FIG. 4N). Information on the genotype of the human subjects is provided in FIG. 11.

MAVS Oligomerization is Reduced in the MAVS-C79F Variant Associated with Milder SLE Activity.

Figure 5A:
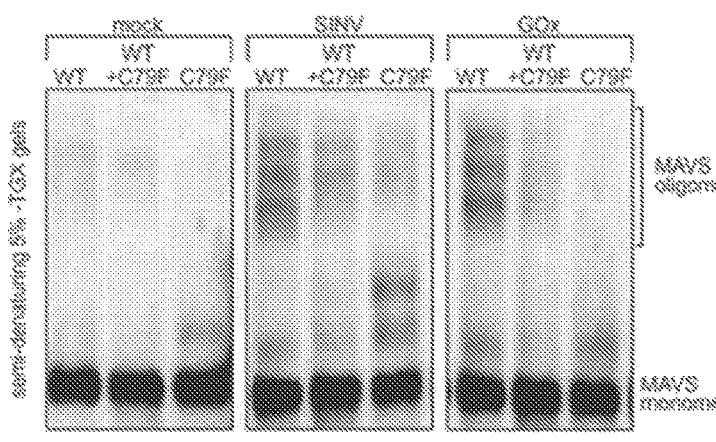
FIG. 5A-G provides blots and graphs of results demonstrating that SLE MAVS-C79F SNP reduces MAVS oligomerization.
Figure 5B:
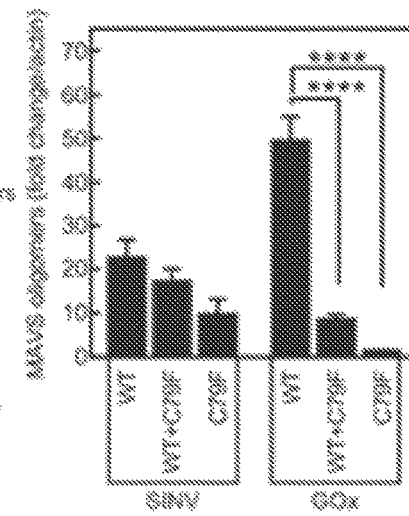
Figure 5C:
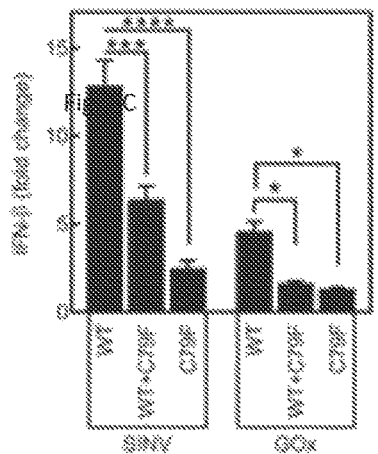
Figure 5D:
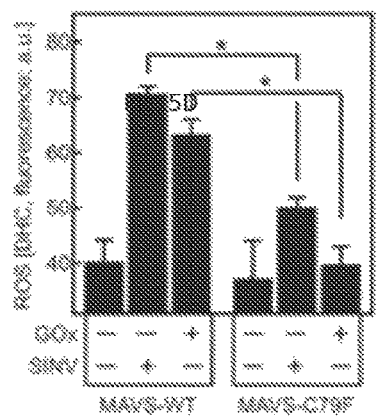
Figure 5E:
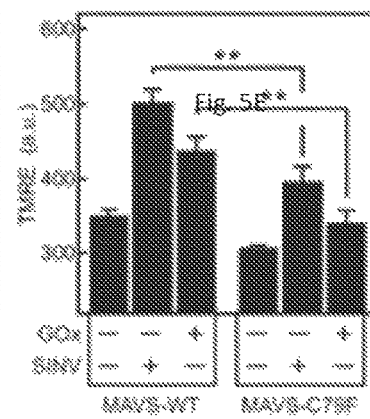
Figure 5F:
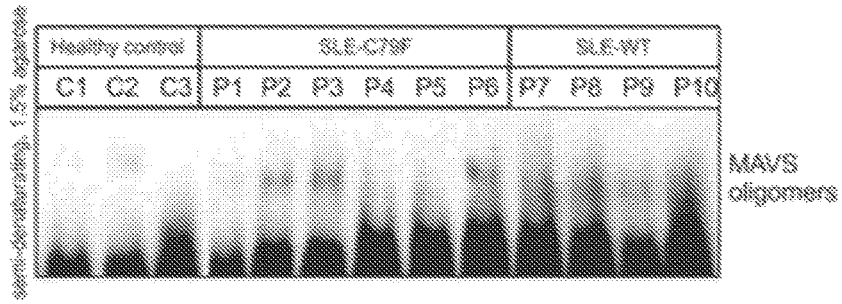
Figure 5G:
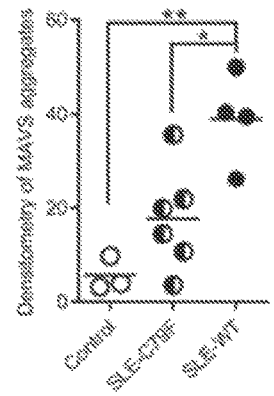

SLE patients bearing a MAVS-C79F SNP have milder disease, lower production of IFN-I, and lack autoantibodies to RNA-binding proteins (J. Pothlichet et al., (2011) EMBO molecular medicine 3, 142-152). In addition, cells expressing MAVS-C79F secrete a lesser amount of inflammatory mediators such as IL-8, RANTES, and IFN-β (J. Pothlichet et al., (2011) EMBO molecular medicine 3, 142-152). The SNP modifies a cysteine residue. Experiments were performed to evaluate whether the SNP modification might alter the ability of MAVS-C79F to form oligomers under oxidative stress. MAVS-KO MEFs were reconstituted with human MAVS-WT, the C79F variant, or a combination of the two (FIG. 5A). It was observed that cells reconstituted with the MAVS-C79F variant manifested lower amounts of MAVS oligomerization following treatment with GOx. The same C79F cells following SINV infection did not show significant decrease in high molecular weight MAVS oligomers as compared to GOx treatment but presence of moderate size oligomers was detected whose size might reflect trimer or tetramer formation (FIGS. 5, A and B). Interestingly, although differences were observed in the level of MAVS oligomerization between SINV and GOx, IFN-I secretion was affected following both treatments (FIG. 5C). Further, under oxidative stress, cells expressing MAVS-C79F exhibited less mROS and $\Delta\Psi_m$, suggesting that this variant had little capacity to promote mitochondrial hyperpolarization (FIGS. 5 D and E).

Based on these observations in MEFs, MAVS oligomerization was examined in 6 SLE MAVS-C79F patients, 4 SLE MAVS-WT patients, and 3 healthy controls, all from the original C79F SNP study (J. Pothlichet et al., (2011) EMBO molecular medicine 3, 142-152), and whose plasma was frozen at the same time. It was observed that MAVS oligomerization was significantly lower in the plasma of the MAVS-C79F patients, compared to SLE patients bearing wild-type MAVS (FIGS. 5 F and G).

MAVS Oligomers from SLE Patients can Induce Prion-Like MAVS Aggregates.

Figure 6A:
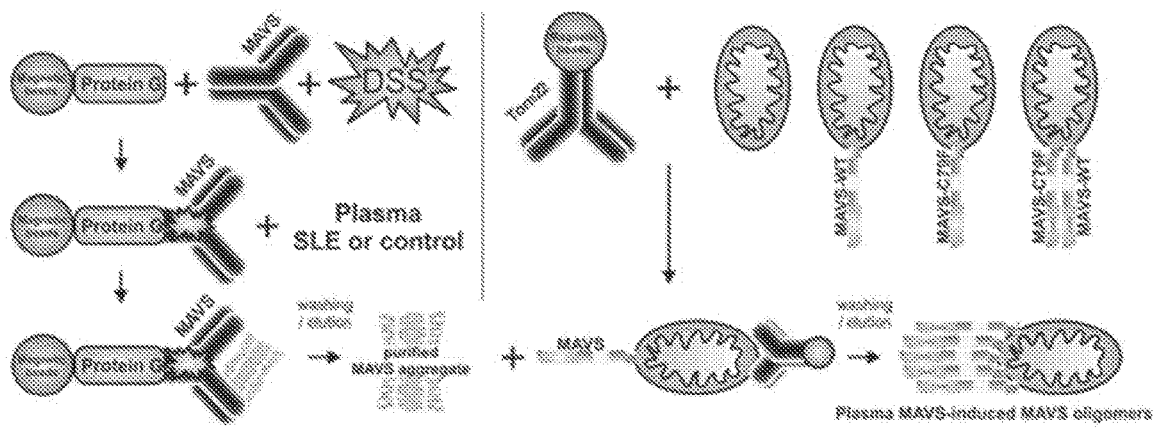
FIG. 6A-D provides a schematic diagram and blots demonstrating MAVS oligomers from SLE patients manifest prion-like activity.
Figure 6B:
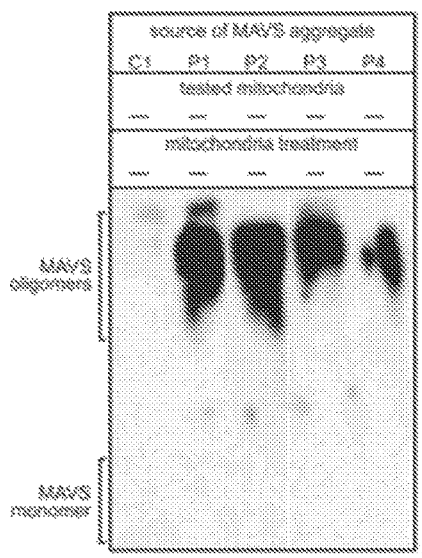
Figure 6C:
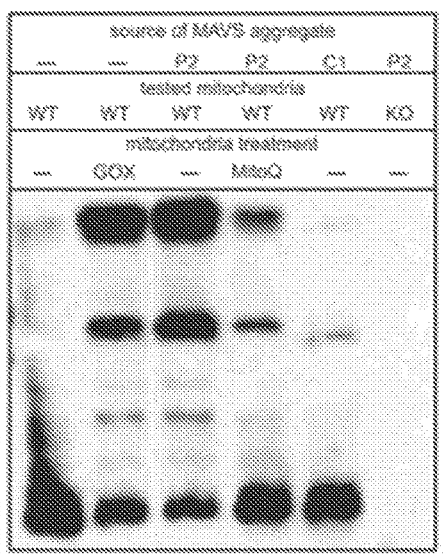

Studies were performed to examine whether MAVS oligomers detected in the plasma of SLE patients have the ability to induce MAVS oligomerization in purified mitochondria from wild-type MEFs that were not exposed to oxidative stress. The plasma MAVS oligomer fraction was purified by immunoprecipitation using an anti-MAVS antibody cross-linked to protein G magnetic beads (FIGS. 6 A and B). Plasma samples were initially pre-incubated with protein G magnetic beads alone to remove nonspecifically bound proteins, followed by incubation with anti-MAVS protein G beads. Following purification and elution, it was observed that MAVS oligomers purified from different patients' plasma had a fairly uniform molecular weight of ~1500 kDa (FIG. 6C). Purified MAVS-oligomers from patients or healthy age- and sex-matched healthy control plasma were incubated with freshly purified mitochondria from normal MEFs for 30 min in a respiration-promoting buffer. Unbound donor MAVS oligomers were then removed by re-purification of the mitochondria using anti-Tom22 magnetic beads, as illustrated in FIG. 6A. As a positive control, it was observed that GOx treatment of purified mitochondria induced MAVS oligomerization (FIG. 6C, lane 2), similar to treatment of intact cells (FIG. 2A). Significantly, it was observed that MAVS oligomers isolated from SLE patient plasma induced MAVS oligomerization of isolated mitochondria (FIG. 6C, lane 3), and that this was significantly decreased in mitochondria pretreated with MitoQ (FIG. 6C, lane 4). Treatment of purified mitochondria with the plasma from a healthy control (C1) did not induce detectable high-molecular-weight MAVS oligomers (FIG. 6C, lane 5). As a negative control, purified MAVS oligomers from SLE patient plasma did not associate with mitochondria isolated from MAVS-KO cells (FIG. 6C, lane 6).

Figure 6D:

To further distinguish induced oligomers of endogenous MAVS from pre-existing SLE-donor MAVS oligomers, the same experiments were performed with mitochondria from MAVS-KO MEFs that expressed His-tagged human MAVS-WT, MAVS-C79F, or a combination of the two. Following treatment with SLE MAVS-WT oligomers, high-molecular-weight bands detected by the anti-His antibody were observed, again demonstrating that donor SLE MAVS oligomers could induce aggregation of endogenous MAVS (FIG. 6D). Additionally, reduced MAVS aggregation was observed when mitochondria contained MAVS-C79F or a combination of MAVS-WT and MAVS-C79F (FIG. 6D, lanes 3 and 4). Taken together, these data show that the MAVS oligomers in the plasma of SLE patients have the ability to induce prion-like oligomerization of endogenous MAVS.

Dendritic Cells Take Up Prion-Like MAVS Aggregates.

Figure 7A:
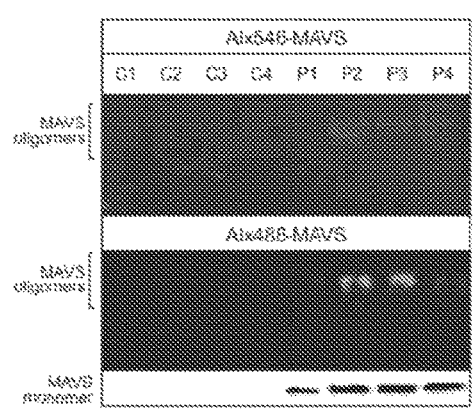
FIG. 7A-H provides blots, graphs and photomicrographic images of results demonstrating that SLE-derived MAVS oligomers are internalized by DCs and induce mitochondrial MAVS aggregation.

To examine whether human or murine DCs can internalize MAVS oligomers purified from plasma of SLE patients, MAVS were labeled with either Alexa Fluor 546 (Alx546) or Alexa Fluor 488 (Alx488) (FIG. 7A). Prior to enriching and labeling MAVS oligomers from plasma, total plasma was first treated with protein G magnetic beads alone and filtered through 100-kDa cut-off membranes to remove non-specific small-molecular-weight oligomers and cytokines. MAVS oligomers from plasma were bound with anti-MAVS-protein G magnetic beads and coupled to Alx546 or Alx488 while the MAVS oligomers were still bound to the MAVS antibody tethered to magnetic beads. This effectively removed excess dye without passing the material through another size-exclusion resin. As a negative control, plasma from healthy controls that was free of MAVS oligomers was also labeled to exclude the labeling of other plasma proteins. TGX gel analysis confirmed that labeling did not affect the stability of MAVS oligomers in SLE plasma, nor did it induce it in healthy control plasma (FIG. 7A). As MAVS oligomerization was highest in patient samples P2-P4, these samples were used for further studies (FIG. 7A). Quantification of MAVS aggregate fluorescence accounted for more than 85-90% of the total monomer MAVS obtained by treatment with β-Me and detected by luminescence with a CARD domain-specific MAVS antibody.

Figure 7B:
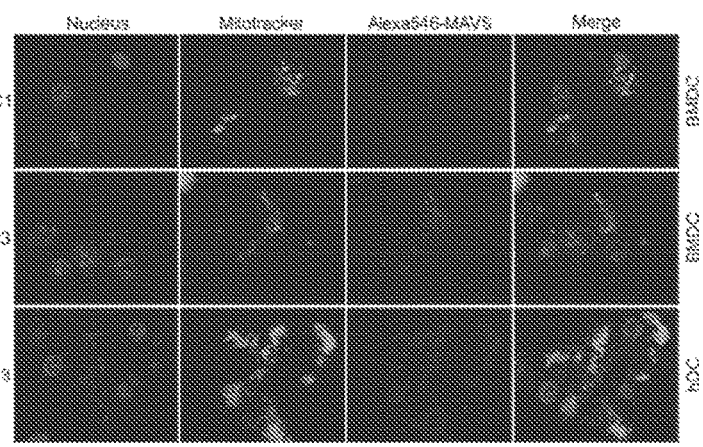
Figure 7C:
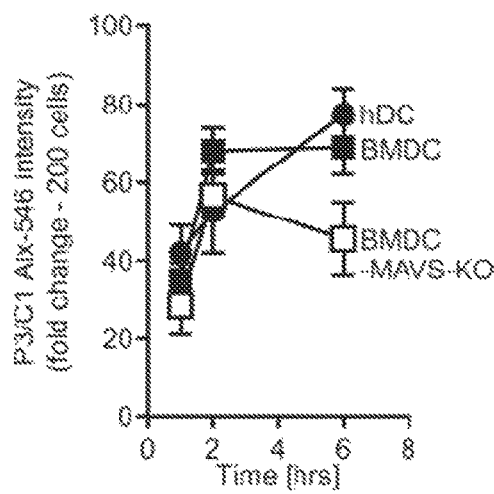
Figure 7D:
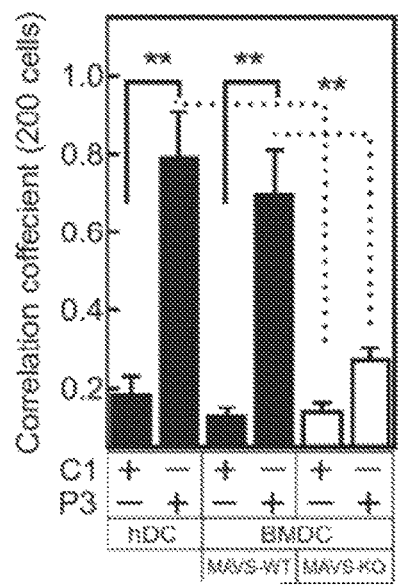

Experiments were performed to examine whether labeled MAVS aggregates could be taken up by DC derived from human peripheral blood monocytes (hDC) or murine bone marrow derived DC (BMDC) (M. Dauer et al., (2003) J. Immunol. 170, 4069-4076; K. Inaba et al., (1992) J. Exp. Med. 176, 1693-1702). As a control, BMDC derived from MAVS-KO mice was also tested. Confocal microscopy was used to verify the rate of MAVS internalization and to note its intracellular location relative to mitochondria using MitoTracker. Alx546-MAVS aggregate uptake and detection in both human hDCs and BMDCs occurred within 1 h (FIGS. 7, B and C). Alx546 cytoplasmic staining was not observed in DCs treated with Alx546-labeled plasma samples from healthy controls, as freely diffusing, non-associated MAVS yield significantly weaker fluorescence. (FIG. 7B). In contrast, exogenous MAVS oligomers required the presence of endogenous MAVS in order to associate with mitochondria, and to induce IFN-I production from host cells. The increase in intracellular MAVS-fluorescence stems from the localization and association of exogenous MAVS with mitochondria, which results in an increase of local fluorescence signal. Calculation of the colocaliztion correlation coefficient of Alx546-MAVS and MitoTracker-green fluorescence demonstrated an association of exogenous MAVS and mitochondria however this was substantially reduced in MAVS-KO BMDC (FIG. 7D). Mitochondrial colocalization of internalized MAVS aggregates also closely paralleled induced amounts of IFN-I secretion in wild-type BMDC, and was not detected in MAVS-KO BMDC. In addition, IFN-I was induced using MAVS aggregates from SLE patients (P2-P4), but not using healthy control plasma (C1, C2) (FIG. 7E).

The association of internalized exogenous MAVS with mitochondria and endogenous MAVS was further confirmed by purifying mitochondria from BMDC. It was observed that labeled MAVS oligomers from the plasma of the SLE patients, but not healthy control plasma, induced endogenous MAVS oligomerization (FIG. 7F, upper panel). The presence of exogenous SLE MAVS aggregates in the mitochondrial fraction was confirmed by direct detection of labeled Alx488-MAVS in the gel. In agreement with the experiments performed using isolated mitochondria, MAVS oligomers could not be observed in the mitochondrial fraction of BMDCs isolated from MAVS-KO mice (FIG. 7F, lower panel). To control whether the fluorophore treatment alone of DCs could promote spontaneous MAVS oligomerization, BMDCs were treated with free Alx488-fluorophore, which did not lead to increased MAVS expression or oligomerization (FIG. 7G). This demonstrated that any increased MAVS oligomerization following treatment with purified MAVs oligomers detected in samples P2-P4 originated from either the association of exogenous MAVS aggregate with endogenous MAVS on mitochondria or prion-like induced oligomerization.

Figure 7E:
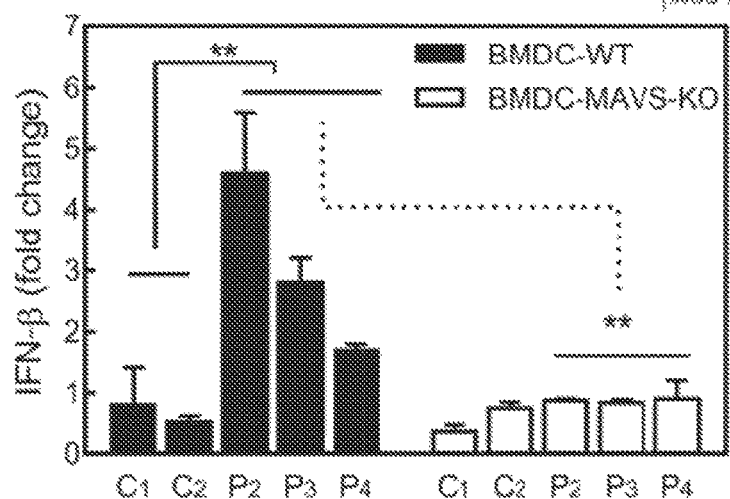
Figure 7F:
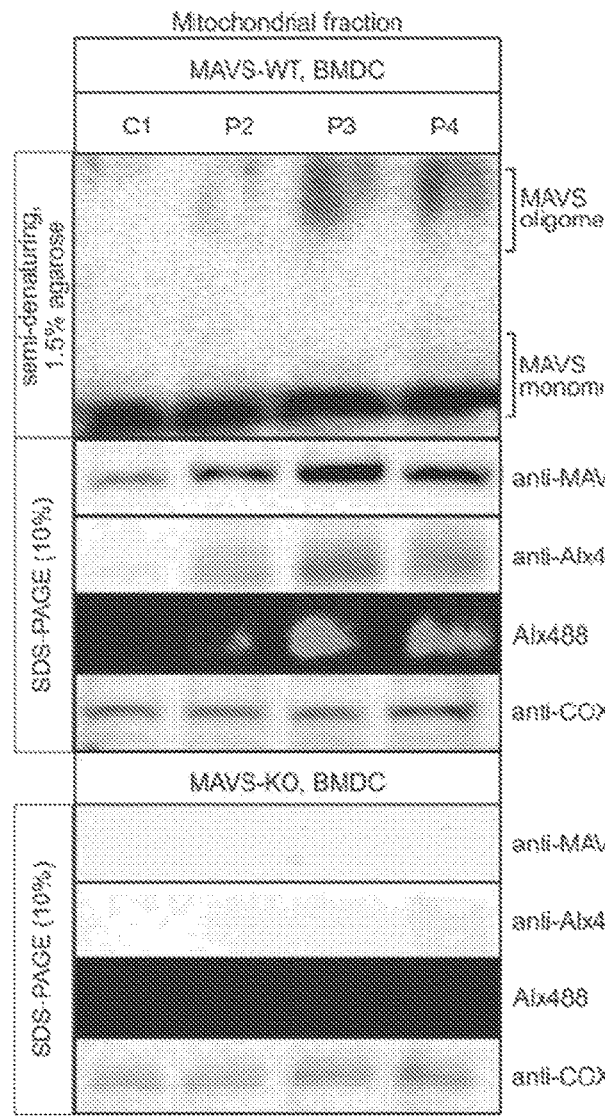
Figure 7G:
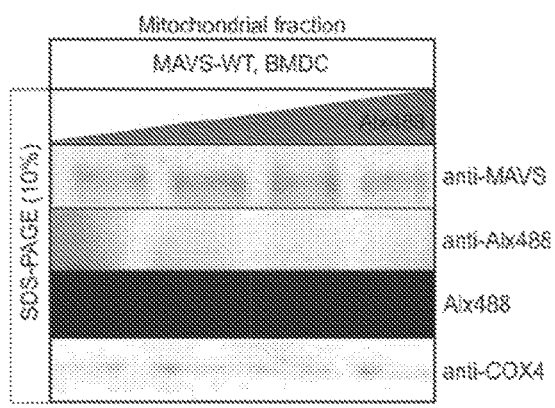
Figure 7H:
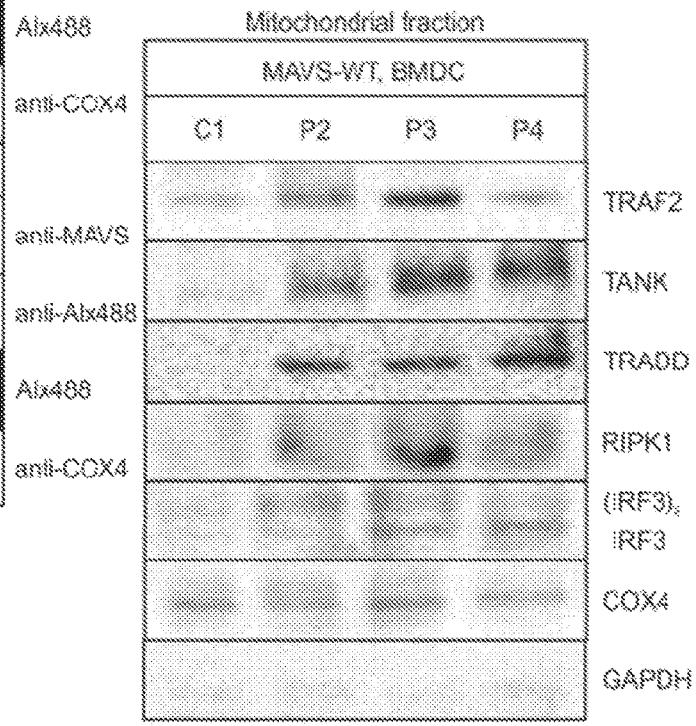
Figure 8A:
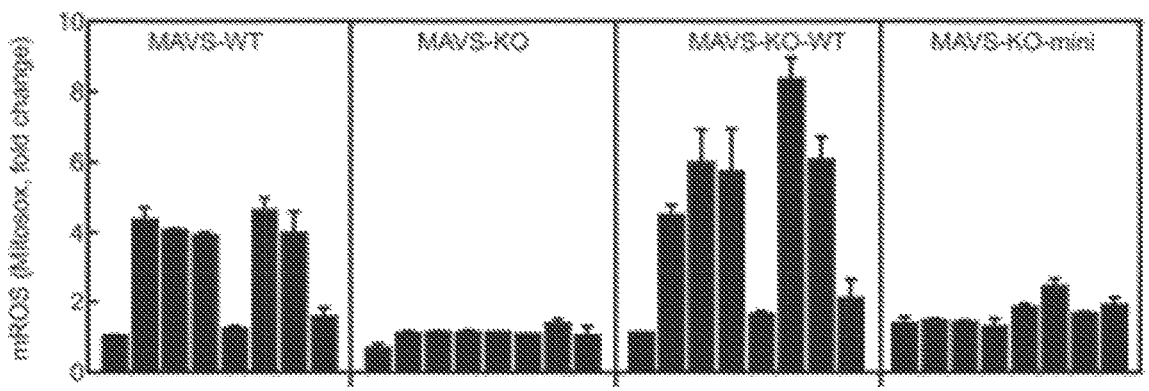
FIG. 8A-E provides graphs and photomicrographic images of results obtained from measurement of mROS, mitochondrial mass and mitochondrial phenotype.
Figure 8B:
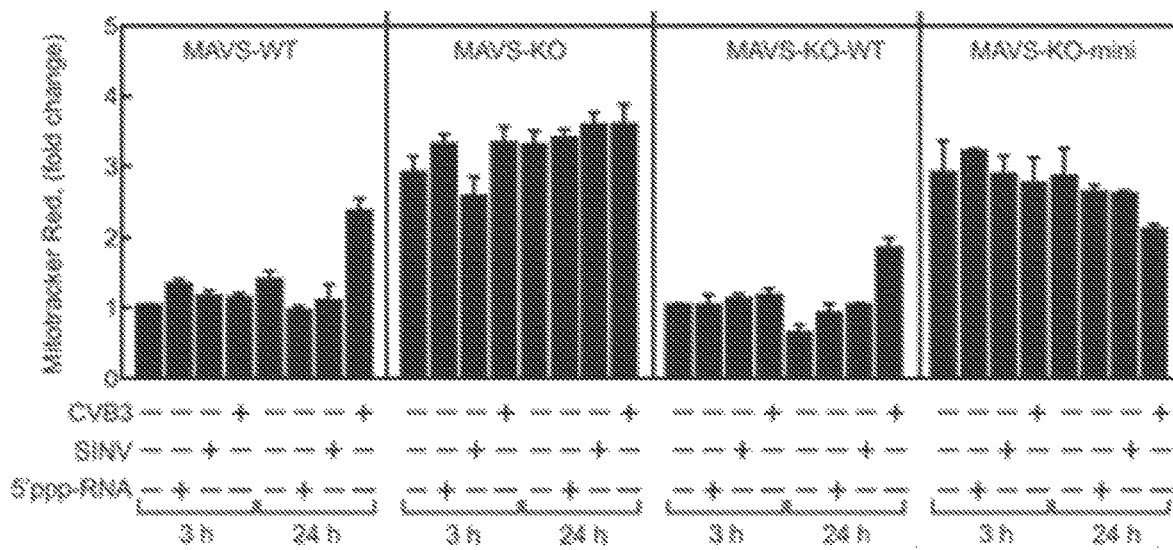
Figure 8C:
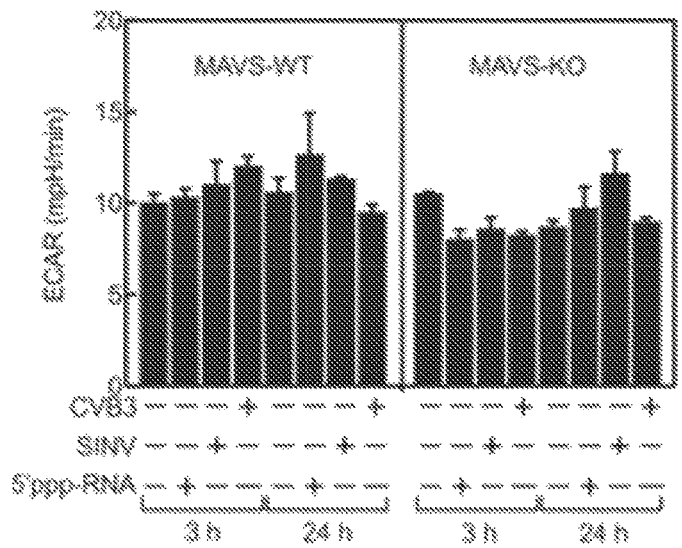
Figure 8D:
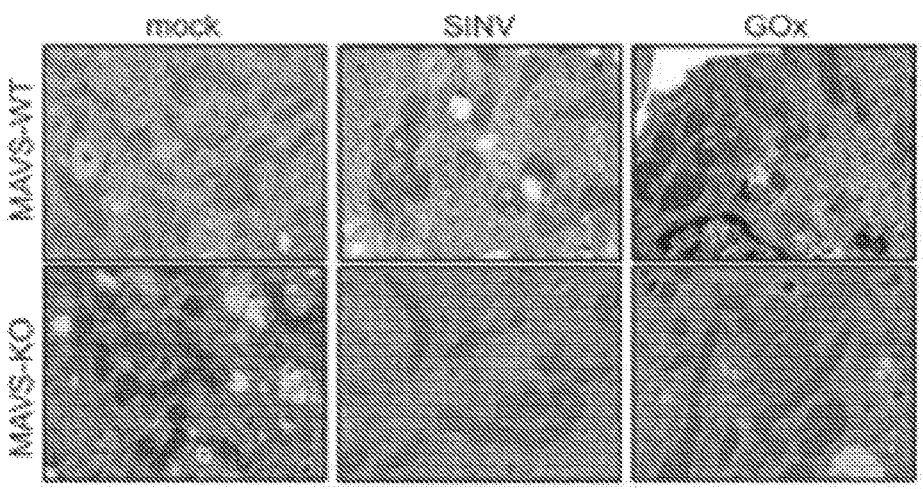
Figure 8E:
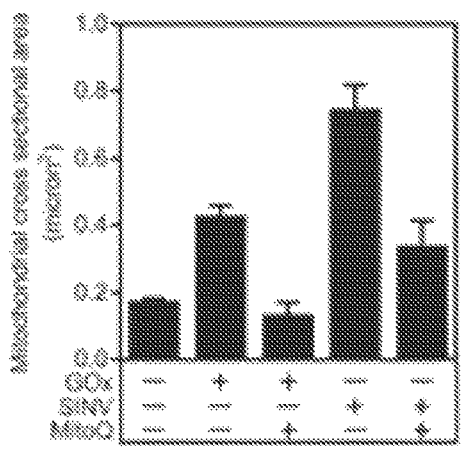

Finally, it was observed that treatment of mitochondria isolated from BMDC with purified MAVS aggregates from SLE plasma (P1-P4), but not healthy controls (C1), resulted in increased mitochondrial colocalization of MAVS signaling complex proteins TRAF2, TANK, TRADD, and RIPK1, and the formation of active IRF3 dimers (FIG. 7H), consistent with the earlier findings for IFN-I secretion from BMDCs (FIG. 7E).

The experimental results obtained support a model in which oxidative stress can induce the oligomerization of MAVS, resulting in activation of IFN-I and NF-κB pathways. The fact that spontaneous MAVS oligomerization was observed in the PBMCs of SLE patients provides an important mechanistic link between the observations of increased oxidative stress and mitochondrial dysfunction in SLE lymphocytes and the IFN-I signature found in many SLE patients (M. Dauer et al (2003) J. Immunol. 170, 4069-4076). The experimental results suggested viral and RNA independent activation of MAVS and IFN-I in SLE and supports the inhibition of MAVS oligomerization as a therapy for autoimmune disorders such as SLE.

Example 2

Protein Assays, Such as an h-FRET Assay

Figure 12:
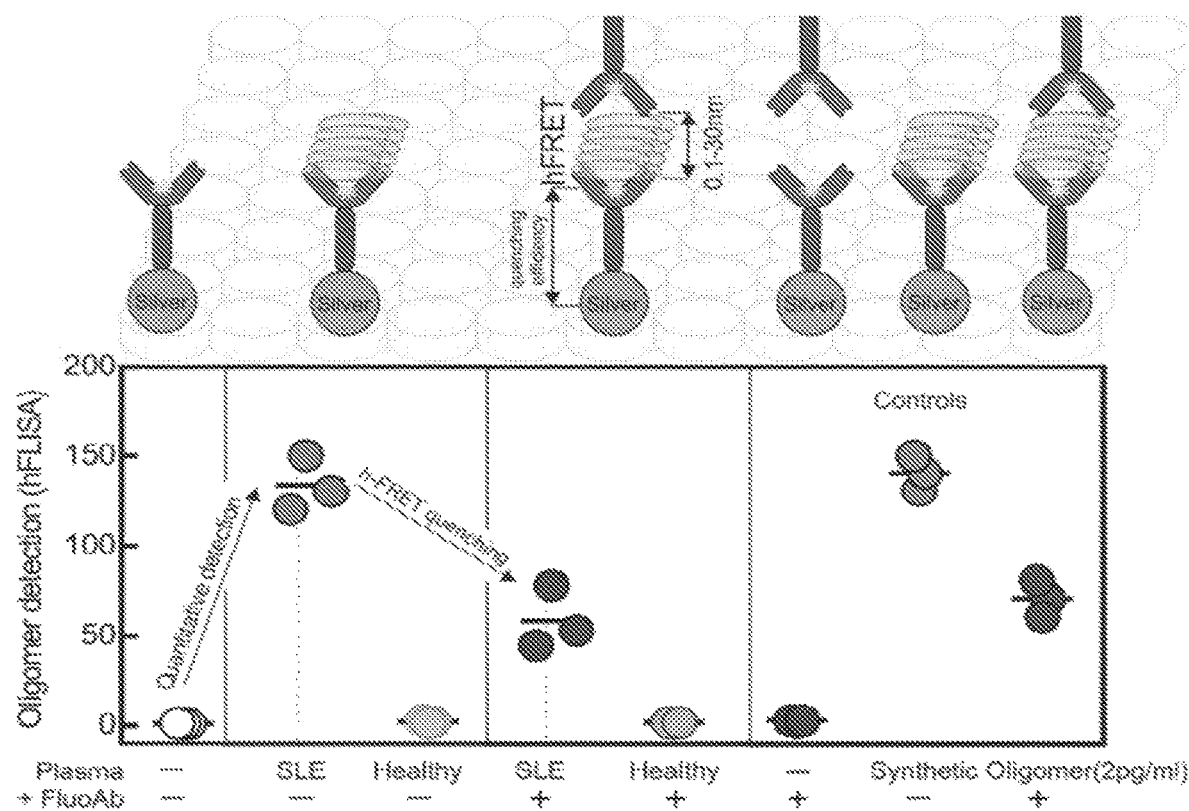
FIG. 12 is a schematic diagram and graph illustrating an h-FRET assay used to assess an amount of MAVS oligomers. The figure shows the presence of mitochondrial oligomers in plasma as monitored by h-ELISA. The labeled antibody was tethered to a bead immobilized to the bottom of a place and fluorescence was read before and after the addition of the patent plasma. Experiments were performed that established specific labeling of antibody for the SLE oligomer to increase the fluorescence by a factor of 100-150. The third reading was performed upon addition of the same labeled antibody but without any bead attached. This step leads to quenching of fluorescence and depends on the space that separates the immobilized and free antibody.

An assay was designed and performed that combined immunoprecipitation and ELISA methods. An embodiment of the assay included use of homo fluorescent resonance energy transfer (FRET) between identical fluorophores tethered to the same antibody specific to (specifically bound) the oligomerized protein. This assay is referred to as homo-FRET-linked immunosorbent assay or h-FLISA) and is based on self-quenching of fluorescence, which is an effect of non-fluorescent traps in the process of homo resonance energy transfer (RET) that act as a non-radiative "sink" for the excited state energy. Characteristics of the homo-FRET approach coupled with metal or carbon particles for ELISA type detection have not been previously utilized. One such characteristic is that it requires only one type of antibody labeled with one and the same dye. In addition, the assay in some aspects was used in a no-wash assay, which required only triple reading of the plate exposed to the plasma of patient and two rows of 6 point control samples. The assay provided not only quantitative but also qualitative determination of the oligomer size, based on use of FRET. In some embodiments of the assay, metal beads were utilized, which increased the sensitivity of the oligomer size detection. Assays were performed using silver beads and assays were performed using gold beads and both were shown to increase fluorescence sensitivity. In addition, it was found that by altering the distance between the metal bead and the detectable label (for example a fluorophore dye) allowed manipulation of the homo-FRET quenching. Therefore the method could be extended to monitor oligomers of different sizes. FIG. 12 shows a schematic of an embodiment of an assay.

Procedures that may be used in the h-FRET assays are placing multiple identical dyes on a single antibody, which improves overall brightness and photostability of the system. The labeling however does not exceed more than 2 or 3 of fluorescence dye per antibody to exclude the possibility of self-quenching within the one not coupled antibody. Dyes are selected that are photostable, exhibit minimal blinking and are characterized by overlap integral between each one's absorption and emission spectra, which would lead to Förster energy resonance. The pair of dyes is selected based on the size of oligomer to be detected and is not limited to any commercially available dye. To enhance detection or modulate the distance required for Förster energy resonance the antibodies are coupled to a plate which is monolayered with the metallic particles fabricated from Silver, Gold, Copper, Aluminum, Zinc, Nickel, Palladium, Tungsten, Platinum, Germanium, Indium, Iron, Tin, Rhodium or combinations thereof.

Metal or carbon nanoparticles enhance the FRET efficiency through metal-fluorophore interaction, leading to an increase in quantum yield and emission intensity of the fluorophore and spectral overlap between the absorption and emission spectra. Although the phenomenon of metal-enhanced FRET efficiency has been reported, there is very limited progress in the development of bioanalytical methods for the detection of proteins using this approach. In h-FRET as described and tested herein, includes tethering the metal bead with antibody either with standard linker peptides or with a novel idea of using DNA oligomers as the linker molecules. DNA oligomers based on their composition either wire or inhibit electron transport, which promotes fluorescence. Therefore the composition of DNA oligomer used in h-FRET methods depends on the desired enhancement or inhibition of fluorescence. A DNA oligomer used as a linker in such assays is composed of either guanosine-cysteine base pairs, which enhance wiring of electrons from the metal to the peptide labeled with fluorophore or inosinse-cysteine or adenosine-thymidine, which have the opposite property and lead to inhibition of photo-induced electron transfer. The DNA oligomer or peptide linker is also varied in its length to enhance or inhibit the electron transport based on the exhaustion of the electron transport with distance.

Example 3

MAVS Oligomers Inhibit DRP1 Binding to Mitochondria and Mitochondrial Fission/MAVS Oligomers Bind to Cardiolipin and Accelerate Cardiolipin Oxidation/MAVS Oligomers are Bound to Cardiolipin in Plasma.

Mitochondrial dysfunction plays a fundamental role in abnormal T-cell function in patients with systemic lupus erythematosus (SLE) [Perl, A., et al., Int Rev Immunol, 2004. 23(3-4): p. 293-313]. Although the mitochondria in T cells of SLE patients have continually elevated mitochondrial transmembrane potential (ΔΨm), they are unable to engage in mitochondrial fission, which is not only needed to create new mitochondria, but also to remove damaged mitochondria from cells during high levels of cellular stress. The mechanism that drives inhibition of fission leading to mitochondrial accumulation and promoting cell death in the T cells of SLE patients is not known. Under healthy conditions, fission is induced by dynamin-related protein 1 (Drp1) upon translocation from the cytoplasm to mitochondria. Drp1 activation and recruitment to mitochondria may be mediated by cardiolipin (CL) [Bustillo-Zabalbeitia, I., et al., PLoS One, 2014. 9(7): p. e102738], a lipid uniquely found in mitochondrial inner and outer membranes [Ardail, D., et al., J Biol Chem, 1990. 265(31): p. 18797-802].

General Methods

Figure 14A:
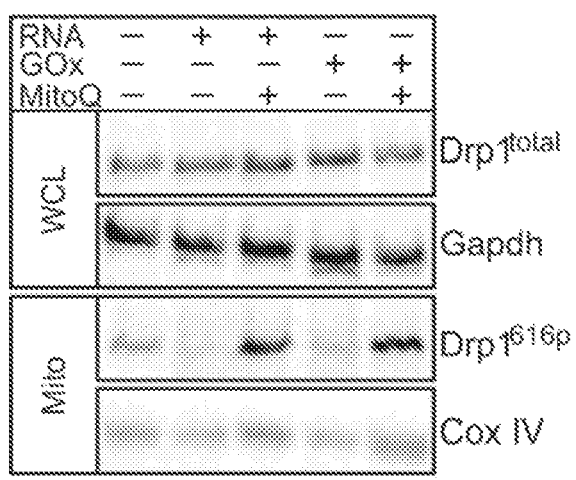
FIG. 14A-B provides a blot and a graph demonstrating the absence of Drp1 at mitochondria isolated from cells with activated MAVS.
Figure 14B:
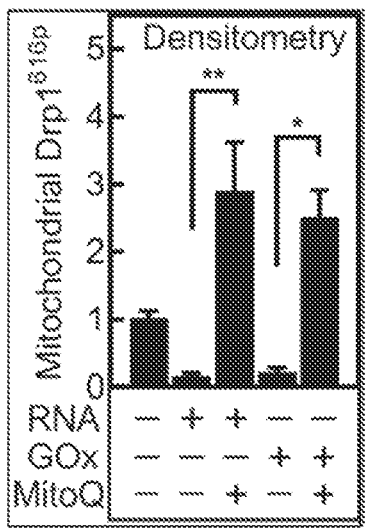

To activate MAVS commercially available 5'-ppp-RNA was used at a concentration of 1 μg/ml, which activates RIG-I helicase. As an alternative GOx was used as previously described [Szeto, H. H., Br J Pharmacol, 2014. 171(8): p. 2029-50]. Mitochondria were purified by anti-Tom22 magnetic beads as previously described [Perl, A., et al., Int Rev Immunol, 2004. 23(3-4): p. 293-313]. Changes in the level of Drp1$^{616p}$ at mitochondria were determined by densitometry, which was normalized to the level of Cox IV (FIG. 14A-B).

Figure 15A:
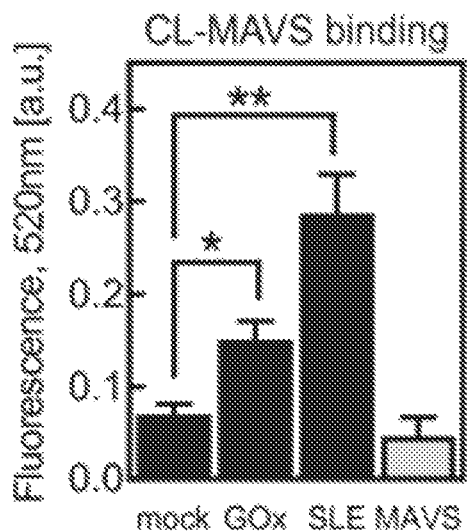
FIG. 15A-B provides a graph and a blot showing CL-MAVS oligomer interaction.
Figure 15B:
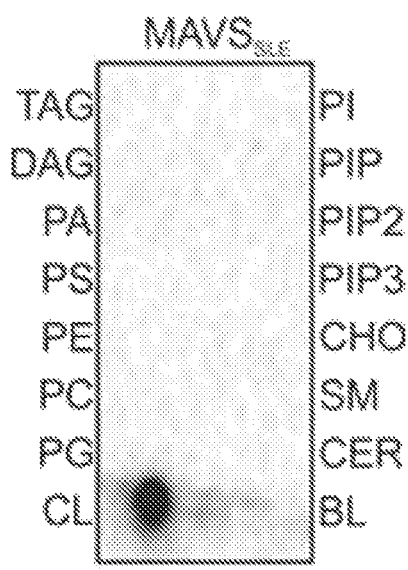

To assess MAVS oligomer interaction a plate coated with anti-phospholipid antibody was prepared and was later was saturated with purified CL. The same plate was exposed to purified and Alx488 labeled MAVS oligomers from mock or GOx treated healthy controls, or from SLE patients as previously published [Szeto, H. H., Br J Pharmacol, 2014. 171(8): p. 2029-50]. Following washing, fluorescence of captured MAVS oligomers was measured. As a control we used recombinant, purified and Alx488 labeled MAVS monomers. Results are shown in FIG. 15A with data shown as mean±SEM, with results representative of two experiments. FIG. 15B shows results of studies of interaction between MAVS oligomers and various peptides. The results demonstrated the presence of MAVS oligomer interaction with CL. Tests were performed on membrane lipid-strips (Echelon Biosciences). The strips were exposed to 1 μg/ml of MAVS oligomer isolated from SLE patients. The strips were washed with mild detergent and treated with phospholipase A2 (PLA2).

Results and Discussion

Figure 13:
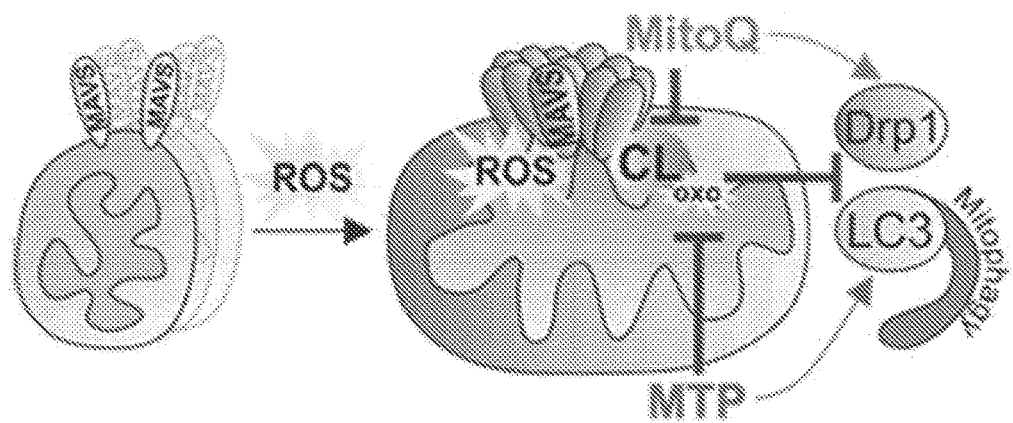
FIG. 13 is a schematic drawing demonstrating role of MAVS oligomer in inhibition of mitochondrial fission and mitophagy in SLE subjects.

Studies were performed to assess association between oligomerized MAVS and cardiolipin (CL). Results indicated that oligomerized MAVS associated with CL. The results also showed that MAVS oligomerization inhibited Drp1 from binding to mitochondria, which suggested that MAVS oligomers occluded CL from binding to Drp1, thereby inhibiting the induction of fission and leading to an accumulation of dysfunctional mitochondria. (see FIG. 13)

Results indicated that MAVS oligomerization resulted in DRP1 depletion and/or inhibition. Subjects with autoimmune diseases, such as: SLE, atherosclerosis, Sjorgen syndrome, rheumatoid arthritis, asthma that is positive for type I IFN signature, dilated cardiomyopathy, cardiomyopathy, systemic sclerosis, Aicardi-Goutieres syndrome, type I diabetes, autoimmune thyroid disease, and neuromyelitis optica may be monitored using methods to detect MAVS oligomerization. In addition, results of the studies suggested that blocking CL from the mitochondrial surface by MAVS, prevent CL's interaction with microtubule-associated protein 1A/B light chain 3B (LC3) or Parkin, which targets dysfunctional mitochondria for turnover through autophagy (hereafter referred to as mitophagy). In addition, the study results support a conclusion that a mitochondria-targeted antioxidant, for example: MitoQ or another mitochondrial-targeted antioxidant, could be utilized in treatment methods that also include administration of an agent that binds CL, for example, the mitochondria-targeted tetra peptide (MTP), also known as Szeto-Shiler peptide. MTP binds to CL and protects it from oxidation [Szeto, H. H., Br J Pharmacol, 2014. 171(8): p. 2029-50, Szeto, H. H., AAPS J, 2006. 8(2): p. E277-83].

Results indicated that MAVS oligomers interacted with cardiolipin and support the use of compounds that target CL, such as MTP, to prevent MAVS oligomerization and thereby reduce the ability of MAVS oligomers to interact with CL. Results suggest that the reduction of interaction of MAVS oligomers with CL can restore fission and mitophagy. The results of the studies demonstrated therapeutic value in treatment of SLE with a combination of a mitochondrial-targeted antioxidant an agent that inhibits CL function. Such a treatment combination includes targeting CL in autoimmune diseases such as SLE, and is a treatment that may not only eliminate a characteristically high type I IFN signature and restore mitochondrial function, but may also limit the toxicity of pro-oxidant/immunosuppressant medications currently used in the treatment of SLE. The results support treatment methods that may include a combination of cardiolipin-targeted agents (for example, peptides such as MTP) and mitochondria-targeted antioxidants (for example, MitoQ).

Results of the studies also demonstrated that MAVS oligomers interact with cardiolipin and therefore may be used to in methods to detect MAVS oligomers. The results support use of MAVS oligomer detection as a biomarker of cardiolipin release into plasma. The interaction of MAVS oligomers and cardiolipin may be used as a biomarker for patients, who have anti-phospholipid syndrome and are also positive for type I IFN signature. It was identified that MAVS oligomerization correlates with lack of mitochondrial fission supporting use methods to of identifying and detecting MAVS oligomerization to assess and monitor for patients treated with type I IFN and having heart distress. For example, identifying an increase in MAVS oligomerization may be used to identify early development of dilated cardiomyopathy.

MAVS Oligomerization Inhibits, and MitoQ Restores Binding of Phosphorylated Drp1 to Mitochondria.

Targeting phosphorylated Drp1 to mitochondria, specifically at serine 616, is the first step in inducing Drp1-mediated mitochondrial fission [Otera, H., et al., Biochim Biophys Acta, 2013. 1833(5): p. 1256-68]. The results indicated that MAVS oligomerization induced by 5'-ppp-RNA, which resembles viral RNA, or treatment with GOx resulted in lower levels of phosphorylated Drp1 at mitochondria, in contrast to higher levels in the same cells pre-treated with MitoQ (FIG. 14A-B).

MAVS Oligomers Interact with CL.

It was recently reported that lipids may be involved in MAVS oligomerization [Nobre, L., et al., PLoS One, 2015. 10(8): p. e0136883], but the identity and the mechanism of lipid-MAVS interaction was unknown. A novel plate-based assay was designed and used to detect CL's interaction with MAVS oligomers and monomers (FIG. 15A). Results showed that CL enrichment had occurred in MAVS signaling complexes that were purified after GOx treatment of PBMC isolated from healthy donors, or that had originated from the PBMCs of SLE patients. Using a commercially available blot dot, it was confirmed that of the 18 lipids tested, only CL showed a significant interaction with MAVS oligomers (FIG. 15B).

The results suggested that MAVS oligomers sequester CL, promote CL's oxidation and that MitoQ can prevent it. Redistribution of CL in mitochondria has been shown to serve as a signal for the induction of mitophagy both directly and independently of any other proteins [Buskiewicz, I., et al., Science Signaling, 2016. 12(456)]. The results of the studies described herein support a conclusion that mitochondria with oligomerized MAVS in SLE patients will have a lower level of mitophagy, and MAVS oligomers, by changing the spatial and oxidative status of CL at mitochondria, prevent LC3 from binding to CL on mitochondria and consequently hinder mitophagy. The results suggest that agents such as MitoQ and MTP can be used to restore CL interaction with LC3 and therefore mitophagy in SLE T cells.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. A method of selecting an autoimmune disease treatment for a subject, comprising:
   (a) identifying a subject at risk for a type 1 interferon (IFN) signature autoimmune disease;
   (b) obtaining a serum sample from the subject;
   (c) contacting the serum sample with a mitochondrial antiviral signaling (MAVS)-binding agent under suitable conditions for the MAVS-binding agent to form a bound complex comprising the MAVS-binding agent and an oligomerized MAVS polypeptide complex, wherein the MAVS-binding agent is a MAVS-binding antibody or antigen-binding fragment thereof;
   (d) determining a characteristic of the bound complex, wherein the characteristic of the bound complex comprises one or more of (i) the presence or absence of an oligomerized MAVS polypeptide complex, and (ii) an amount or level of an oligomerized MAVS polypeptide complex in the serum sample, wherein one or more of: the presence of oligomerized MAVS polypeptide complex in the sample and a higher amount or level of the oligomerized MAVS polypeptide complex in the sample compared to a control amount or level, identifies the subject as at risk of the type 1 IFN signature autoimmune disease;
   (e) selecting a treatment for the type 1 IFN signature autoimmune disease based at least in part on the subject's identified risk; and
   (f) administering the selected treatment for the type 1 IFN signature autoimmune disease to the subject.

2. The method of claim 1, further comprising determining one or more of:(iii) a degree or level of oligomerization of MAVS polypeptides in an oligomerized MAVS polypeptide complex; (iv) a molecular weight of an oligomerized MAVS polypeptide complex; (v) a size of an oligomerized MAVS polypeptide complex; and (vi) one or more other identified physical feature of an oligomerized MAVS polypeptide complex in the serum sample.

3. A method of preparing a bound complex comprising a serum mitochondrial antiviral-signalling (MAVS) oligomerized polypeptide complex and a MAVS-binding agent, the method comprising:
   contacting a MAVS-binding agent with a serum sample believed to be at risk of containing an oligomerized MAVS polypeptide complex, wherein the MAVS-binding agent is a MAVS-binding antibody or antigen-binding fragment thereof and the contact is under conditions suitable for the MAV-binding agent to form a bound complex with the oligomerized MAVS polypeptide complex.

4. The method of claim 3, further comprising determining a characteristic of the bound complex in the contacted serum sample, wherein the characteristic of the bound complex is one or more of the level of the bound complex and a physical property of the oligomerized MAVS polypeptide complex in the bound complex.

5. The method of claim 4, wherein the physical property of the oligomerized MAVS polypeptide complex comprises the molecular weight of the oligomerized MAVS polypeptide complex.

6. The method of claim 3, wherein the MAVS-binding agent specifically binds an N-terminal caspase activation and recruitment domain (CARD) of MAVS.

7. The method of claim 3, wherein the oligomerized MAVS polypeptide complex comprises the oligomerized MAVS polypeptide and an additional component that is optionally a phospholipid.

8. The method of claim 7, wherein the phospholipid is cardiolipin.

9. The method of claim 4, further comprising using the determined characteristic to assist in identifying the presence of an autoimmune disease in the subject.

10. The method of claim 4, further comprising using the determined characteristic to assist in one or more of: selecting a treatment for the subject and treating the subject.

11. The method of claim 3, wherein the serum sample is from a subject and the specific binding of the MAVS-binding agent to the N-terminal caspase activation and recruitment domain (CARD) of MAVS aids in selecting administration of at least one anti-oxidative agent as a treatment for the subject.

* * * * *

SEQUENCE LISTING

```
<160> NUMBER OF SEQ ID NOS: 23

<210> SEQ ID NO 1
<211> LENGTH: 540
<212> TYPE: PRT
<213> ORGANISM: Homo sapiens

<400> SEQUENCE: 1

Met Pro Phe Ala Glu Asp Lys Thr Tyr Lys Tyr Ile Cys Arg Asn Phe
1               5                   10                  15

Ser Asn Phe Cys Asn Val Asp Val Val Glu Ile Leu Pro Tyr Leu Pro
            20                  25                  30

Cys Leu Thr Ala Arg Asp Gln Asp Arg Leu Arg Ala Thr Cys Thr Leu
        35                  40                  45

Ser Gly Asn Arg Asp Thr Leu Trp His Leu Phe Asn Thr Leu Gln Arg
    50                  55                  60

Arg Pro Gly Trp Val Glu Tyr Phe Ile Ala Ala Leu Arg Gly Cys Glu
65                  70                  75                  80

Leu Val Asp Leu Ala Asp Glu Val Ala Ser Val Tyr Gln Ser Tyr Gln
                85                  90                  95

Pro Arg Thr Ser Asp Arg Pro Asp Pro Leu Glu Pro Pro Ser Leu
                100                 105                 110

Pro Ala Glu Arg Pro Gly Pro Pro Thr Pro Ala Ala Ala His Ser Ile
            115                 120                 125

Pro Tyr Asn Ser Cys Arg Glu Lys Glu Pro Ser Tyr Pro Met Pro Val
        130                 135                 140
```

Gln Glu Thr Gln Ala Pro Glu Ser Pro Gly Glu Asn Ser Glu Gln Ala
145                 150                 155                 160

Leu Gln Thr Leu Ser Pro Arg Ala Ile Pro Arg Asn Pro Asp Gly Gly
            165                 170                 175

Pro Leu Glu Ser Ser Ser Asp Leu Ala Ala Leu Ser Pro Leu Thr Ser
            180                 185                 190

Ser Gly His Gln Glu Gln Asp Thr Glu Leu Gly Ser Thr His Thr Ala
            195                 200                 205

Gly Ala Thr Ser Ser Leu Thr Pro Ser Arg Gly Pro Val Ser Pro Ser
210                 215                 220

Val Ser Phe Gln Pro Leu Ala Arg Ser Thr Pro Arg Ala Ser Arg Leu
225                 230                 235                 240

Pro Gly Pro Thr Gly Ser Val Val Ser Thr Gly Thr Ser Phe Ser Ser
            245                 250                 255

Ser Ser Pro Gly Leu Ala Ser Ala Gly Ala Ala Glu Gly Lys Gln Gly
            260                 265                 270

Ala Glu Ser Asp Gln Ala Glu Pro Ile Ile Cys Ser Ser Gly Ala Glu
            275                 280                 285

Ala Pro Ala Asn Ser Leu Pro Ser Lys Val Pro Thr Thr Leu Met Pro
290                 295                 300

Val Asn Thr Val Ala Leu Lys Val Pro Ala Asn Pro Ala Ser Val Ser
305                 310                 315                 320

Thr Val Pro Ser Lys Leu Pro Thr Ser Ser Lys Pro Gly Ala Val
            325                 330                 335

Pro Ser Asn Ala Leu Thr Asn Pro Ala Pro Ser Lys Leu Pro Ile Asn
            340                 345                 350

Ser Thr Arg Ala Gly Met Val Pro Ser Lys Val Pro Thr Ser Met Val
            355                 360                 365

Leu Thr Lys Val Ser Ala Ser Thr Val Pro Thr Asp Gly Ser Ser Arg
370                 375                 380

Asn Glu Glu Thr Pro Ala Ala Pro Thr Pro Ala Gly Ala Thr Gly Gly
385                 390                 395                 400

Ser Ser Ala Trp Leu Asp Ser Ser Glu Asn Arg Gly Leu Gly Ser
            405                 410                 415

Glu Leu Ser Lys Pro Gly Val Leu Ala Ser Gln Val Asp Ser Pro Phe
            420                 425                 430

Ser Gly Cys Phe Glu Asp Leu Ala Ile Ser Ala Ser Thr Ser Leu Gly
            435                 440                 445

Met Gly Pro Cys His Gly Pro Glu Glu Asn Glu Tyr Lys Ser Glu Gly
            450                 455                 460

Thr Phe Gly Ile His Val Ala Glu Asn Pro Ser Ile Gln Leu Leu Glu
465                 470                 475                 480

Gly Asn Pro Gly Pro Pro Ala Asp Pro Asp Gly Gly Pro Arg Pro Gln
            485                 490                 495

Ala Asp Arg Lys Phe Gln Glu Arg Glu Val Pro Cys His Arg Pro Ser
            500                 505                 510

Pro Gly Ala Leu Trp Leu Gln Val Ala Val Thr Gly Val Leu Val Val
            515                 520                 525

Thr Leu Leu Val Val Leu Tyr Arg Arg Arg Leu His
            530                 535                 540

<210> SEQ ID NO 2
<211> LENGTH: 91

```
<212> TYPE: PRT
<213> ORGANISM: Homo sapiens

<400> SEQUENCE: 2

Phe Ala Glu Asp Lys Thr Tyr Lys Tyr Ile Cys Arg Asn Phe Ser Asn
1               5                   10                  15

Phe Cys Asn Val Asp Val Val Glu Ile Leu Pro Tyr Leu Pro Cys Leu
                20                  25                  30

Thr Ala Arg Asp Gln Asp Arg Leu Arg Ala Thr Cys Thr Leu Ser Gly
            35                  40                  45

Asn Arg Asp Thr Leu Trp His Leu Phe Asn Thr Leu Gln Arg Arg Pro
        50                  55                  60

Gly Trp Val Glu Tyr Phe Ile Ala Ala Leu Arg Gly Cys Glu Leu Val
65              70                  75                  80

Asp Leu Ala Asp Glu Val Ala Ser Val Tyr Gln
                85                  90

<210> SEQ ID NO 3
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 3

Cys Arg Ile Asp Val Val Asp Ile Ile Pro Tyr Leu Ser Glu Cys Leu
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 4

Cys Leu Ile Asn Gln Asp Gln Asp Cys Asp Glu Ile Arg Gln Ile
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Cys Arg Asn Phe Ser Asn Phe
1               5

<210> SEQ ID NO 6
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 6

Ile Cys Arg Asn Phe Lys Ala Phe Ser Cys Asp Leu Ala Val Arg Ile
1               5                   10                  15

Ser Ile Leu Pro
                20
```

```
<210> SEQ ID NO 7
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 7

Arg Asn Phe Ser Asn Asn Val Asp Val Ile Ile Val Gln Leu Asn Glu
1               5                   10                  15

Ser Val Glu Ile
            20

<210> SEQ ID NO 8
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 8

Asn Val Glu Val Val Asp Glu Ile Leu Pro Tyr
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 9

Val Glu Ile Leu Pro Tyr Leu Pro Cys
1               5

<210> SEQ ID NO 10
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 10

Asp Val Leu Ile Glu Val Asp Ile Leu Pro Phe Leu Pro Cys
1               5                   10

<210> SEQ ID NO 11
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 11

Ala Arg Asp Gln Asp Arg Leu Arg Ala Thr Cys Thr Leu Ser Gly Asn
1               5                   10                  15

Arg Asp Thr

<210> SEQ ID NO 12
<211> LENGTH: 16
<212> TYPE: PRT
<213> ORGANISM: Artificial Sequence
<220> FEATURE:
<223> OTHER INFORMATION: Synthetic Polypeptide conjugated to a TAT
      sequence

<400> SEQUENCE: 12
```

```
Cys Arg Ile Asp Val Val Asp Ile Ile Pro Tyr Leu Ser Glu Cys Leu
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Polypeptide conjugated to a TAT
      sequence

<400> SEQUENCE: 13

Cys Leu Ile Asn Gln Asp Gln Asp Cys Asp Glu Ile Arg Gln Ile
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Synthetic Polypeptide conjugated to a TAT
      sequence

<400> SEQUENCE: 14

Cys Arg Asn Phe Ser Asn Phe
1               5

<210> SEQ ID NO 15
<211> LENGTH: 20
<212> TYPE: PRT
<213> ORGANISM: Artificial Sequence
<220> FEATURE:
<223> OTHER INFORMATION: Synthetic Polypeptide conjugated to a TAT
      sequence

<400> SEQUENCE: 15

Ile Cys Arg Asn Phe Lys Ala Phe Ser Cys Asp Leu Ala Val Arg Ile
1               5                   10                  15

Ser Ile Leu Pro
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic Polypeptide conjugated to a TAT
      sequence

<400> SEQUENCE: 16

Arg Asn Phe Ser Asn Val Asp Val Ile Ile Val Gln Leu Asn Glu
1               5                   10                  15

Ser Val Glu Ile
            20

<210> SEQ ID NO 17
<211> LENGTH: 11
<212> TYPE: PRT
<213> ORGANISM: Artificial Sequence
<220> FEATURE:
<223> OTHER INFORMATION: Synthetic Polypeptide conjugated to a TAT
      sequence

<400> SEQUENCE: 17

Asn Val Glu Val Val Asp Glu Ile Leu Pro Tyr
1               5                   10
```

```
<210> SEQ ID NO 18
<211> LENGTH: 9
<212> TYPE: PRT
<213> ORGANISM: Artificial Sequence
<220> FEATURE:
<223> OTHER INFORMATION: Synthetic Polypeptide conjugated to a TAT
      sequence

<400> SEQUENCE: 18

Val Glu Ile Leu Pro Tyr Leu Pro Cys
1               5

<210> SEQ ID NO 19
<211> LENGTH: 14
<212> TYPE: PRT
<213> ORGANISM: Artificial Sequence
<220> FEATURE:
<223> OTHER INFORMATION: Synthetic Polypeptide conjugated to a TAT
      sequence

<400> SEQUENCE: 19

Asp Val Leu Ile Glu Val Asp Ile Leu Pro Phe Leu Pro Cys
1               5                  10

<210> SEQ ID NO 20
<211> LENGTH: 19
<212> TYPE: PRT
<213> ORGANISM: Artificial Sequence
<220> FEATURE:
<223> OTHER INFORMATION: Synthetic Polypeptide conjugated to a TAT
      sequence

<400> SEQUENCE: 20

Ala Arg Asp Gln Asp Arg Leu Arg Ala Thr Cys Thr Leu Ser Gly Asn
1               5                   10                  15

Arg Asp Thr

<210> SEQ ID NO 21
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 21

Gly Arg Lys Lys Arg Arg Gln Arg Arg Arg Pro Gln
1               5                   10

<210> SEQ ID NO 22
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 22
ccctgggggc catattaatc c                                              21

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 23
catcaaatcg cctccgagca                                                   20
```